United States Patent [19]
Landscheidt et al.

[11] Patent Number: 5,543,548
[45] Date of Patent: Aug. 6, 1996

[54] PROCESS FOR THE PREPARATION OF DIMETHYL CARBONATE

[75] Inventors: Heinz Landscheidt, Duisburg; Erich Wolters, Köln; Paul Wagner, Düsseldorf; Alexander Klausener, Köln, all of Germany

[73] Assignee: Bayer Aktiengesellschaft, Leverkusen, Germany

[21] Appl. No.: 273,548

[22] Filed: Jul. 11, 1994

[30] Foreign Application Priority Data

Jul. 15, 1993 [DE] Germany .......................... 43 23 675.8
Jul. 15, 1993 [DE] Germany .......................... 43 23 682.0

[51] Int. Cl.$^6$ .................................................. C07C 69/96
[52] U.S. Cl. ........................................... 558/277; 558/260
[58] Field of Search ............................................. 558/277

[56] References Cited

FOREIGN PATENT DOCUMENTS 0523728  1/1993  European Pat. Off. .
1470160  4/1977  United Kingdom .

OTHER PUBLICATIONS

WPI/Derwent, Week 9422, AN94–183383, Ube Ind. Ltd.; "Production of carbonated diester from nitrous ester and carbon monoxide . . .", T. Kurafuji et al. 1994.

Chemical Abstract, vol. 113, 61719q, p. 138, abstract for DE 3,834,065, 1990.

Derwent Abstract for Japanese Patent 033445, 1990.

*Primary Examiner*—Gary Geist
*Assistant Examiner*—Dwayne C. Jones
*Attorney, Agent, or Firm*—Sprung Horn Kramer & Woods

[57] ABSTRACT

Dimethyl carbonate (DMC) is prepared by continuous gas reaction of carbon monoxide and methyl nitrite a heterogeneous catalyst comprising a platinum at 50° to 170° C. under 1 to 5 bar.

21 Claims, 13 Drawing Sheets

PROCESS FOR THE PREPARATION OF DIMETHYL CARBONATE

BACKGROUND OF THE INVENTION

1. Field of the Invention

The invention relates to a new process for the continuous preparation of dimethyl carbonate (DMC), characterized in that carbon monoxide and methyl nitrite are reacted with one another in the gas phase in the presence of a heterogeneous catalyst and the dimethyl carbonate thereby formed is isolated in subsequent process steps. The process according to the invention is particularly suitable for the industrial preparation of dimethyl carbonate.

Dimethyl carbonate is an important starting material for the preparation of aromatic polycarbonates. It is used furthermore as a starting material for the synthesis of aliphatic and aromatic mono- and diisocyanates, as a methylating agent, as a substitute for toxic phosgene in the preparation of pharmaceutical and agrochemical products, as a solvent and an agent for improving the octane rating of carburettor fuels, and as an intermediate product in the preparation of synthetic lubricants.

2. Description of the Related Art

The reaction between carbon monoxide and methyl nitrite, which is based on the formation of dimethyl carbonate, can be described by reaction equation (1).

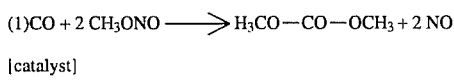

[catalyst]

Methyl nitrite itself can be produced for this in a manner known per se in a prior reaction in accordance with one of reaction equations (2) to (5).

$$4\ NO+O_2+4\ CH_3OH \rightarrow 4\ CH_3ONO+2\ H_2O \quad (2)$$

$$NO+NO_2+2\ CH_3OH \rightarrow 2\ CH_3ONO+H_2O \quad (3)$$

$$N_2O_4+CH_3OH \rightarrow CH_3ONO+HNO_3 \quad (4)$$

$$2\ NaNO_2+H_2SO_4+2\ CH_3OH \rightarrow 2\ CH_3ONO+Na_2SO_4+2\ H_2O \quad (5)$$

The preparation of dimethyl carbonate by reaction of carbon monoxide and methyl nitrite in the gas phase in the presence of a heterogeneous catalyst, which is preferably a platinum metal catalyst fixed to a support, has been described in various instances, for example in the following scientific publications, Offenlegungsschriften and patent specifications:

JP 60 181 051, X.-Z. Jiang et al.; Cuihua Xeubao 10 (1) 75–78 (March 1989), EP 425 197, X.-Z. Jiang; Platinum Metals Rev. 34 (4), 178–180 (1990), EP 464 460, EP 503 091, EP 501 507, EP 503 618, EP 523 508, EP 523 728 and EP 538 676, EP 559 001, EP 558 996, EP 559 212, EP 565 076 and EP 581 240.

Apart from the European Patent Application EP 523 728 cited, none of the publications listed describes a route which would be suitable for continuous industrial preparation of dimethyl carbonate. Thus, the reaction products obtained are in general mixtures in which, in addition to dimethyl carbonate, the desired target compound, other substances are present, such as, for example, dimethyl oxalate, which is formed in the course of a side reaction which proceeds according to reaction equation (6), methyl formate, formaldehyde dimethyl acetal, water and, in particular, methanol.

However, such mixtures are completely unsuitable for many of the possible intended uses of dimethyl carbonate.

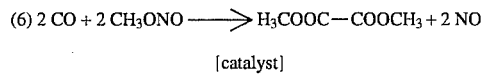

[catalyst]

A continuous process procedure, which is to be aimed for from industrial aspects, must basically correspond to the principle illustrated in FIG. 1, and hence a circulatory process. It must be designed such that the nitrogen oxides obtained in the course of the formation of dimethyl carbonate in accordance with reaction equation (1) and all the other gaseous and condensed products, by-products and auxiliaries either are recycled completely or for the most part into the process, if they can be used or do not adversely impair the economics or the industrial safety of the overall process, or, if these components adversely impair the economics or the industrial safety of the overall process, or are removed from the circulation completely or to the extent necessary for unimpaired continuous operation of the overall process.

EP 523 728 describes a process, the principle of which is illustrated in FIG. 2 and which comprises the continuous preparation of dimethyl carbonate by reaction of methyl nitrite with carbon monoxide in the gas phase over a heterogeneous catalyst, which is preferably a platinum metal contact catalyst fixed to a support, and subsequent isolation of the dimethyl carbonate, obtained as a mixture with methanol, dimethyl oxalate and other impurities, in the course of an extractive distillation in which dimethyl oxalate is used as the extraction agent. EP 523 728 furthermore comprises recycling of the nitrogen oxides liberated in the course of the reaction of methyl nitrite with carbon monoxide, together with the unreacted gaseous reaction partners and the additional gas necessary for rendering the system inert, preferably nitrogen, into a process step which precedes the actual preparation process of dimethyl carbonate and corresponds to reaction equation (2), and in which the methyl nitrite required for the reaction is formed again by feeding in methanol and oxygen and removing to the greatest extent the water thereby liberated. This is thus a circulatory process with respect to the gaseous components participating, that is to say with respect to the inert gases and auxiliaries, the unreacted gaseous reactants, such as, for example, the unreacted methyl nitrite and carbon monoxide, and the nitrogen oxides participating.

The following points are disadvantages of the process described in EP 523 728 which jeopardize its industrial applicability from the economic and ecological aspect:

Large amounts of auxiliaries must be circulated for the preparation, isolation and purification of the dimethyl carbonate. For example, taking the information from Example 1 of the patent application cited as a basis, the following amounts to be circulated per kg of DMC result:

4.8 kg of methanol, 6.0 kg of dimethyl oxalate, 2.8 kg of methyl nitrite, 1.6 kg of carbon monoxide, 1.2 kg of nitrogen monoxide and 7.8 kg of nitrogen In particular, because of the large excess of methanol which is fed into the methyl nitrite reactor 3 of FIG. 2 and is about 500% of the amount required stoichiometrically, a quite considerable distillation expenditure is necessary, which leads to high energy costs if the unreacted content of methanol is to be recovered from the bottom discharge of the reactor.

Since recycling of these auxiliaries and secondary components (water, nitric acid, methyl formate, formaldehyde dimethyl acetal) requires removal by distillation from the dimethyl carbonate, the desired reaction product, above all in respect of methanol and dimethyl oxalate, this process is extremely energy-intensive and is therefore unattractive not only from economic aspects but also from ecological aspects.

In principle, dimethyl oxalate forms oxalic acid half-esters or oxalic acid, in accordance with reaction equations (7) and (3), by reaction with water present in traces, which originates from the preparation of methyl nitrite in the methyl nitrite reactor 3 of FIG. 2 and, because the separation there never takes place completely, is typically contained in reactant gas mixtures and therefore also in product gas mixtures of dimethyl carbonate preparation. Because of their acidity in extraction column 2, and in particular because of the higher temperature in methanol column 4 of FIG. 2, these products can convert the methanol present there into dimethyl ether in accordance with reaction equation (9). This process is autocatalytic, since a further equivalent of water is liberated with each reaction event, and in turn can react again with dimethyl oxalate.

$$H_3COOC-COOCH_3 + H_2O \rightarrow H_3COOC-COOH + CH_3OH \quad (7)$$

$$H_3COOC-COOH + H_2O \rightarrow HOOC-COOH + CH_3OH \quad (8)$$

$$(9) \; 2\,CH_3OH \xrightarrow{[H^+]} H_3C-O-CH_3 + H_2O$$

Furthermore, the oxalic acid half-ester formed in accordance with reaction equation (7) can decarboxylate to form methyl formate in accordance with reaction equation (10).

$$H_3COOC-COOH \rightarrow HCOOCH_3 + CO_2 \quad (10)$$

Industrially available carbon monoxide moreover contains small amounts of gaseous impurities which are inert under the dimethyl carbonate preparation conditions, such as, for example, hydrogen, methane and carbon dioxide, even after extensive purification.

The inevitable accumulation of volatile secondary components in the recycled circulating gas, whether they are those formed in the course of undesirable side reactions or those which the raw materials employed contain as impurities, requires removal of a corresponding content of the circulating gas from the circulation (purging). Although this is mentioned in principle in the process description of the Patent Application EP 523 728 cited, no information is given on the extent and treatment of the amounts of gas removed from the circulation. At all events, it is to be expected that both the economics and the ecology of the process will be impaired by this operation.

Beyond these considerations, the description of the process is inconsistent or defective, for example, at the following places:

A tube-bundle reactor comprising 6 tubes, the tubes of which have a diameter of 26.1 mm each and a length of 500 mm each, is thus described in column 11, lines 40 to 42 of Patent Application EP 523 728. Such a reactor has a maximum volume of 1.6 l. According to line 43 of Patent Application EP 523 728, however, this reactor is filled with 1.73 l of catalyst.

According to column 12, line 15 of Patent Application EP 523 728, 2.8 kg/hour of an absorption solution are removed at the bottom of the dimethyl carbonate extraction column (compare number 2 in FIG. 2 in this application, corresponding to number 2 in FIG. 1 of Patent Application EP 523 728) and are fed to the distillation column (compare number 4 in FIG. 2 in this application, corresponding to number 4 in FIG. 1 of Patent Application EP 523 728). According to column 12, lines 51 to 52 of Patent Application EP 523 728, however, this amount is 3.5 kg/hour.

According to column 13, lines 2 to 4 of Patent Application EP 523 728, a mixture which comprises dimethyl carbonate to the extent of 14.3% and dimethyl oxalate to the extent of 87.5% is removed from the bottom of the first distillation column (methanol distillation, compare number 4 in FIG. 2 in this application, corresponding to number 4 in FIG. 1 of Patent Application EP 523 728). However, in purely mathematical terms, this is not possible.

According to column 13, line 21 of Patent Application EP 523 728, 4.69 kg/hour of dimethyl oxalate are removed from the bottom of the second distillation column (dimethyl carbonate distillation, compare number 5 in FIG. 2 in this application, corresponding to number 5 in FIG. 1 of Patent Application EP 523 728). However, this amount is at least 0.6 kg greater than it can be according to the information in column 12, lines 15 to 16 or in column 12, lines 51 and 55 of Patent Application EP 523 728.

The methanol content of the gas which leaves the methyl nitrite synthesis reactor (number 3 in FIG. 2 in this application, corresponding to number 3 in FIG. 1 of Patent Application EP 523 728) and which, after carbon monoxide has been admixed, is fed into the dimethyl carbonate synthesis reactor (number 1 in FIG. 2 in this application, corresponding to number 1 in FIG. 1 of Patent Application EP 523 728) is determined by the exit temperature of the condenser at the top of the methyl nitrite synthesis reactor for a given pressure and given contents of the other gaseous components present in the total gas mixture. It is not a freely selectable parameter, but corresponds to the partial vapour pressure which is established under these conditions and, for Example 1 of the Patent Application EP 523 728 cited, is between 5.5 and 5.8% by volume. However, 1.8% by volume is mentioned in Example 1, column 11, lines 51 to 52 of the said patent application.

Finally, the data for the amount of water which is formed and removed from the circulation and results from the preparation of methyl nitrite (0.07 kg/hour) do not correspond to the amount which would be expected on the basis of the reaction yields of dimethyl carbonate and dimethyl oxalate described in Example 1 of the EP 523 728 cited, that is to say 0.14 kg/hour.

There was thus the object of discovering a process which is characterized by a lower expenditure of raw materials and energy, by a lower amount of by-products obtained and by a more effective and as far as possible simpler isolation and purification of the desired dimethyl carbonate than is described by the prior art. This object is achieved by the process according to the invention.

Various catalysts and catalyst types are described in the literature for the preparation of dimethyl carbonate carried out in accordance with reaction equation (1) by reaction of carbon monoxide with methyl nitrite over heterogeneous platinum metal supported contact catalysts in the gas phase.

Thus, for example, according to the scientific publication Cuihua Xuebao 10 (1), pages 75 to 78 (March 1989), catalysts which can be used are, for example, palladium(II) halides, preferably palladium(II) chloride, and in particular palladium(II) chloride which is fixed on active charcoal supports and is doped or modified with compounds of iron, lithium and/or copper, high selectivities and space/time yields of the desired dimethyl carbonate being obtained. Similar catalyst systems are described in the Patent Applications EP 425 197, EP 464 460, EP 503 091, EP 503 618 and EP 523 728. Catalysts of this type in general produce the desired dimethyl carbonate in a selectivity which is not completely satisfactory. Undesirable dimethyl oxalate is formed as a by-product in accordance with reaction equation (6). On the one hand, this is detrimental to the highest possible utilization of the raw materials employed, which is to be aimed for, and on the other hand it necessitates an additional separation expenditure in the course of the isolation and purification of the desired dimethyl carbonate. Furthermore, many catalysts of the type mentioned undergo a discharge of halide ions, specifically chloride ions, in general in the form of hydrogen halide formation, specifically hydrogen chloride formation, in the course of relatively long operating times.

This is associated, where appropriate, with a decrease in selectivity with respect to dimethyl carbonate formation and a drop in catalyst activity, although this can be avoided by addition of even small amounts of, for example, hydrogen halide, specifically hydrogen chloride, to the reactant gas mixture, as is described, for example, in the Patent Application EP 425 197 cited. Introduction of the small amounts of hydrogen halide, specifically hydrogen chloride, mentioned results in increased requirements on the materials from which the plant components which come into contact with the compound are to be produced. The formation of characteristic by-products, such as, for example, methyl chloride, which is formed in accordance with reaction equation (11) by the reaction, which runs in parallel with the conditioning of the catalyst, of hydrogen chloride with the methanol which is always present in small amounts in the reactant gas mixture is furthermore to be taken into account. Patent Application EP 565 076 demonstrates by way of example the severe deactivation phenomena (only 50 to 500 hours until the activity has disappeared virtually completely) which catalysts based on active charcoal supports undergo. A process is described there for batchwise regeneration of contact catalysts deactivated to this extent, which comprises sequential treatment of these catalysts with hydrogen and hydrogen halide at elevated temperatures. When realized industrially, such a process would require a constant starting up and running down of the production plant at intervals of a few hundred operating hours in the most favourable case, in order to allow regeneration campaigns. Alternatively, a double reaction procedure could also be conceived, which is operated in alternation between production and regeneration cycles. Another possibility would be to remove portions of the catalyst from the reaction zone batchwise or continuously, to regenerate them externally and to recycle them again to the reactor. In any event, the industrial solution to the deactivation problem would cause high additional costs and would be extremely unfavourable from economic aspects. It may thus be advantageous to resort to catalysts which show no deactivation or only an acceptably lower deactivation on the basis of the discharge of halide ions, specifically chloride ions, mentioned, even if such contact catalysts, such as are described, for example, in the Patent Applications EP 503 091, EP 503 618 and EP 523 728, show a rather more unfavourable selectivity due to the formation of dimethyl oxalate.

$$CH_3OH+HCl \rightarrow CH_3Cl+H_2O \quad (11)$$

To prevent the accumulation of by-products within an industrial circulatory process, portions to be specified of the circulating gas and the condensed reaction products, where these are not dimethyl carbonate itself, must be removed from the circulation (purged) continuously or discontinuously, preferably continuously.

New perspectives result for industrial realization with the discovery of new catalysts which allow the preparation of dimethyl carbonate by heterogeneously catalyzed reaction of methyl nitrite and carbon monoxide in the gas phase with considerably increased selectivities. Contact catalysts of this type, such as are described, for example, in Patent Applications EP 523 508, EP 438 676, EP 559 001, EP 558 996 and EP 581 240 have allowed only very little dimethyl oxalate as a by-product. For example, their activity and their DMC selectivity can be kept at a practically unchanged high level for a long time by continuous addition of very small amounts of hydrogen chloride to the reactant gas mixture.

SUMMARY OF THE INVENTION

The invention relates to a process for the continuous preparation of dimethyl carbonate from carbon monoxide and methyl nitrite and for the recycling of the nitric oxide thereby formed for renewed formation of methyl nitrite, which is characterized in that (a) carbon monoxide and methyl nitrite are reacted in the gas phase in the presence of a heterogeneous catalyst comprising a platinum metal, preferably a supported catalyst comprising palladium, and an inert gas in the temperature range from 50° to 170° C., preferably from 70° to 150° C., and in the pressure range from 1 to 5 bar, preferably 2–4 bar, whereby, as an activator, hydrogen halide, halogen, methyl chloroform and/or other substances which contain halogen acting activating under the reaction conditions in a concentration of 0 to 3,000 ppm, preferably 10 to 1,000 ppm, is added to the gas mixture.

(b) the mixture obtained in (a) is separated into gaseous and liquid reaction products, a part of the gaseous stream of from 0 to 7% by weight, preferably 0.1 to 5% by weight is removed, the therein contained low-boiling constituents are separated off and directed to a further work-up, the therein contained nitrogen monoxide is converted with oxygen and methanol to yield methyl nitrite, which methyl nitrite is separated off and recycled to the process, and the remaining accumulated inert gases are excluded from the process, (c) the gaseous products are reacted with methanol, oxygen and if appropriate freshly added nitric oxide or nitric oxide equivalents for renewed formation of the methyl nitrite, the gas mixture which contains the newly formed methyl nitrite being led off and recycled to the preparation of dimethyl carbonate, and water and any other liquid by-products formed also being led off and removed from the circulation, preferably after subsequent recovery of the useful substances contained therein, and (d) the liquid products from (b) are subjected to separation by distillation, in which the entire product mixture is initially subjected to a first distillation, which is carried out under a pressure of 1 to 25 bar, preferably 1 to 12 bar, and then either (e1) the top product from the first distillation is fed to another distillation carried out under normal pressure or reduced pressure, preferably under 200 to 1500 mbar, in which a methanol-rich discharge is obtained as the bottom product, which is recycled to the preparation of dimethyl carbonate, preferably to the component step for renewed formation of the methyl nitrite, and in which a top product is obtained which is recycled again to the first distillation, if appropriate together with other return streams, or (e2) the top product from the first distillation is fed to a pervaporation or a vapour permeation, which is operated on the retained material side at a temperature of 20° to 150° C. under a pressure of 0.5 to 10 bar and on the permeate side at a temperature of −30° to +30° C. under a pressure of 0.5 to 500 mbar, in which a methanol-rich outflow is obtained as the permeate, which is recycled to the preparation of dimethyl carbonate, preferably to the component step for regeneration of the methyl nitrite, and in which a retained material is obtained which is recycled to the first distillation, if appropriate together with other return streams, and (f) pure dimethyl carbonate is obtained by distillation of the mixture obtained as the bottom runnings of the first distillation carried out under increased pressure.

BRIEF DESCRIPTION OF THE DRAWINGS

The attached drawings.

FIG. 1 shows a continuous circulatory process which is to be aimed for with methyl nitrite synthesis, DMC synthesis, isolation and purification of dimethyl carbonate and recycling of the nitrogen monoxide formed.

FIG. 2 shows the continuous process for the preparation of dimethyl carbonate according to EP 523 728.

FIG. 3 shows the process according to the invention in the variant according to (e1).

FIG. 4 shows the diagram for the experimental procedure of Example 1 (variant e1)).

FIG. 5 shows the process according to the invention in the variant according to (e2).

FIG. 6 shows the diagram for the experimental procedure of Example 2 (variant e2)).

FIG. 7 shows the process according to the invention in the variant according to (e1) as a detailed representation.

FIG. 8 shows a block diagram of apparatus arrangement 8 (within the broken line) for working up of waste gas/recycling of useful substances/removal of by-products from the circulation, which is not shown in more detail in FIGS. 7, 10, 12 and 13.

FIG. 9 shows further details of apparatus arrangement 8 (compare the explanation of FIG. 8).

FIG. 10 shows the diagram for the experimental procedure of Example 3 (variant (e1)).

FIG. 11 shows apparatus arrangement 8, as explained in Examples 3 and 4.

FIG. 12 shows the process according to the invention in the variant according to (e2) in a detailed diagram.

FIG. 13 shows the diagram for the experimental procedure of Example 4 (variant (e2)).

The reference symbols for the apparatuses in FIGS. 1 to 6 have the following meaning: 1=DMC synthesis, 2=scrubber/condenser for the mixture obtained in 1, 2'=DMC extraction (only in FIG. 2), 3=methyl nitrite synthesis, 4=pressure distillation, 4'=methanol distillation I (only in FIG. 2), 5=DMC distillation, 6=waste water distillation, 6'=methanol distillation II (only FIG. 2), 7=methanol removal by further distillation (variant (e1) in FIGS. 3, 4, 7 and 10) or by pervaporation or vapour permeation (variant (e2) in FIGS. 5, 6, 12 and 13), 8=waste gas treatment with 8a= methyl nitrite desorber, 8b=methyl nitrite after-reactor/methanol waste gas scrubber and 8c=low-boiling constituents scrubber, 9,10= storage tank.

The reference symbols for the educts and products in FIGS. 1 to 6 have the following meaning: I=CO, II=CH$_3$OH, III=O$_2$, IV=NaOH (aqueous), V=N$_2$, VI=NO, VII=waste gas (removal from the circulation), VIII=DMC, IX=waste water (removal from the circulation), X=dimethyl oxalate and other by-products (removal from the circulation); additionally only in FIG. 1: XI=gaseous products (chiefly NO), XII=condensed products (chiefly DMC), XIII=secondary components, which are partly removed from the circulation (for example X) and partly recycled, XIV=activator, XV=CO$_2$, XVI=further working up, where appropriate. The other reference symbols are dealt with below.

DETAILED DESCRIPTION OF THE INVENTION

Platinum metals for the catalyst are, for example, Ru, Rh, Pd, Ir or Pt, preferably Pd.

Catalyst supports are known to the expert, for example aluminium oxides, active charcoals, metal phosphates, zeolites, alumosilicates and hetero polyacids, preferably aluminium oxide and A charcoals, particularly preferably aluminium oxides.

Inert gases are, for example, carbon dioxide, nitrogen or argon, preferably nitrogen and carbon dioxide, particularly preferably carbon dioxide.

Figure 1:
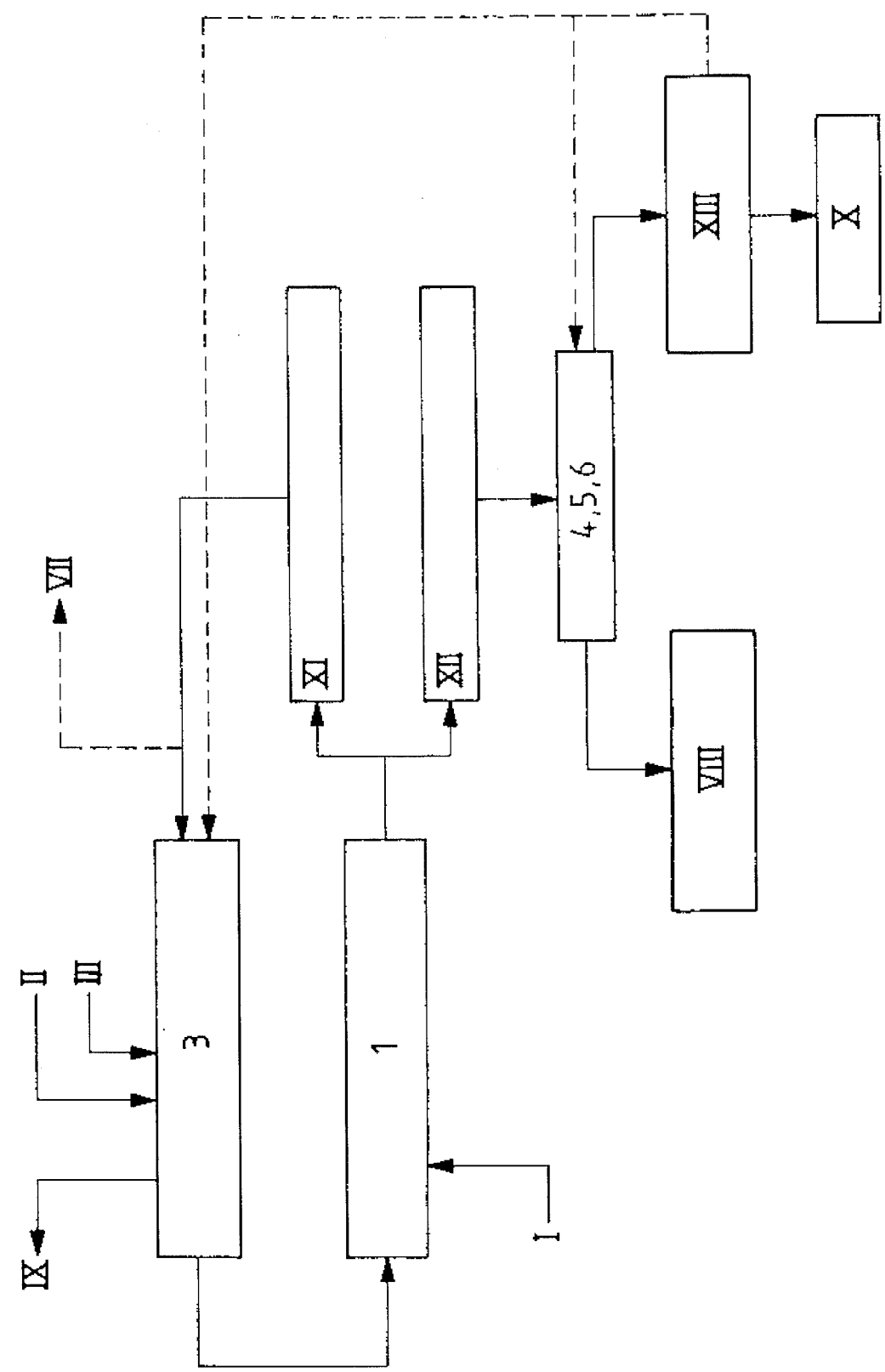
FIGS. 1 to 13, are defined as follows.
Figure 2:
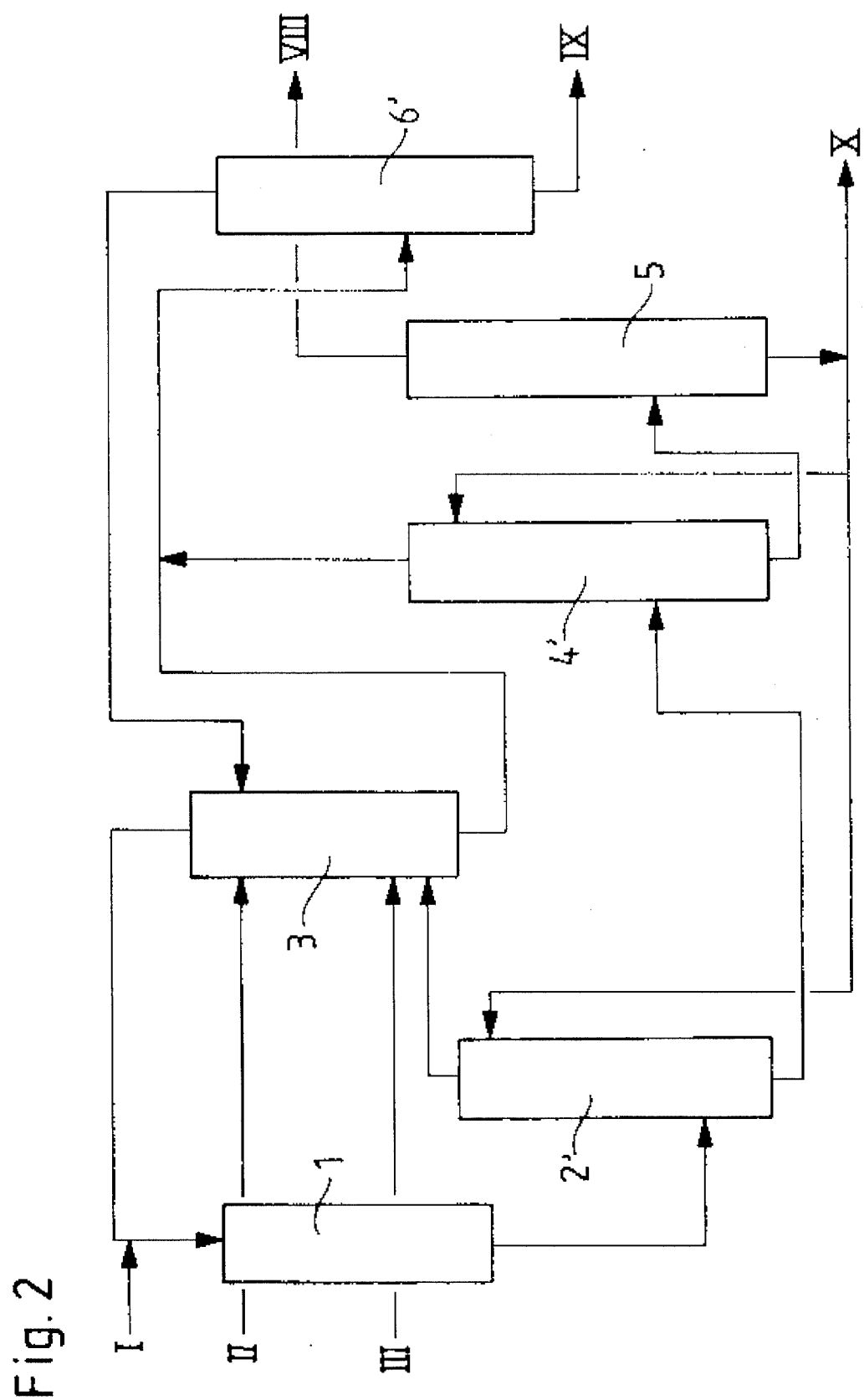
Figure 3:
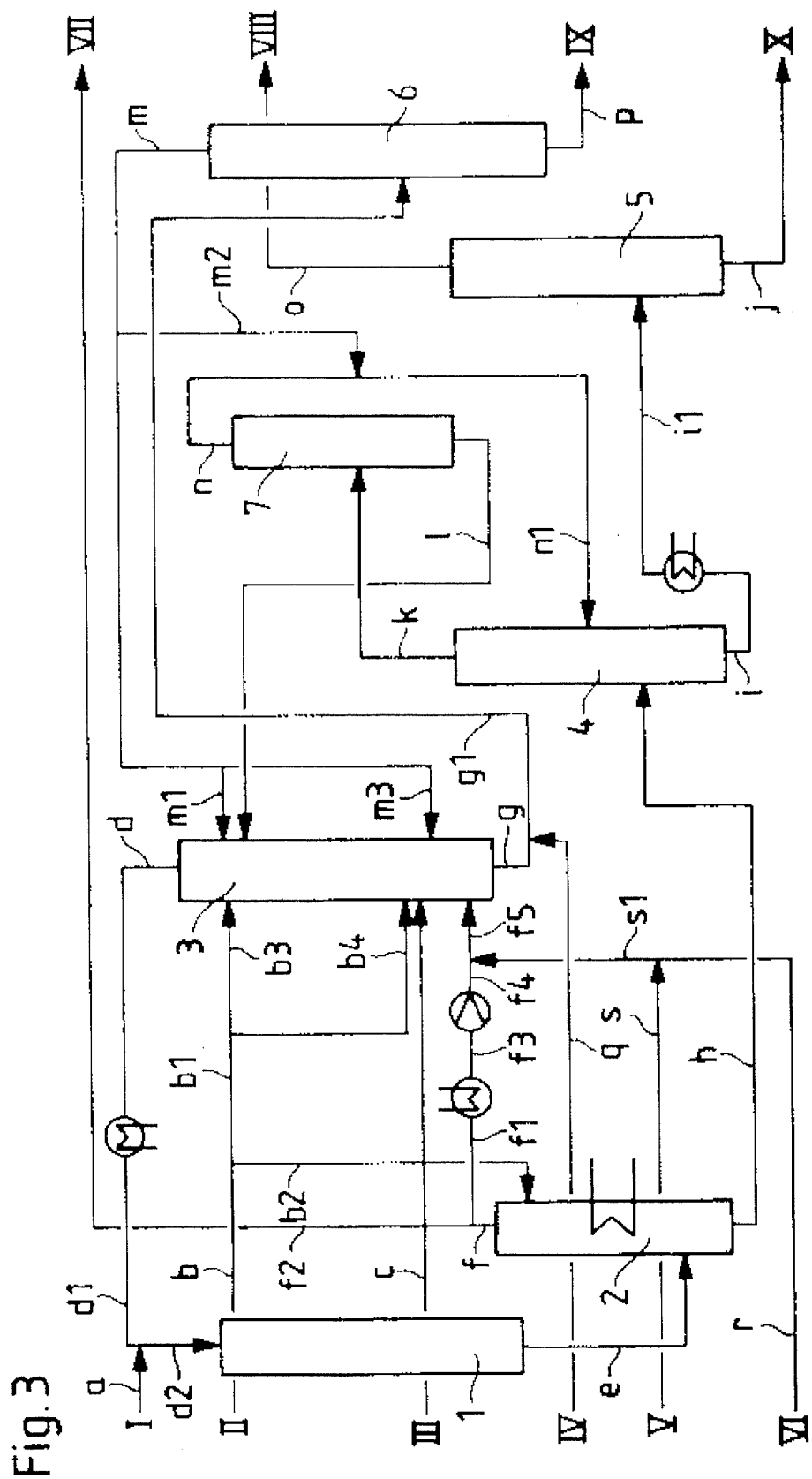

The process according to the invention in the variant according to (e1) is shown as a diagram in FIG. 3. It essentially comprises the reaction, which proceeds in the gas phase within a suitable reactor in the presence of an inert gas, of methyl nitrite with carbon monoxide over a catalyst comprising a platinum metal, preferably palladium. The gaseous reaction products are separated into gaseous and liquid phases in a scrubber/condenser. The gaseous portion, which comprises, inter alia, the nitrogen monoxide formed during the reaction of the methyl nitrite, is reacted with oxygen and methanol in a suitable manner in another reactor for reuse of this portion. The water thereby obtained is passed on to a waste water working up operation, while the methyl nitrite obtained again is recycled to the dimethyl carbonate preparation. The liquid reaction products obtained in the scrubber/condenser are fed to a pressure distillation, in which dimethyl carbonate and high-boiling constituents are separated off, as the base product, from the top product comprising methanol and dimethyl carbonate. Finally, dimethyl carbonate, the desired reaction product, is isolated in a high purity in a final distillation step in which dimethyl carbonate is obtained as the top product and high-boiling constituents, for example dimethyl oxalate, are obtained as the bottom product, while useful substances, such as methanol, are for the most part recycled to the process and waste substances, such as waste water, waste air and high-boiling constituents, are removed from the circulation. The top product of the pressure distillation is distilled again under normal or reduced pressure (variant according to (e1)), a methanol-rich discharge being obtained as the bottom product and being recycled, for example for renewed formation of methyl nitrite, and the top product being fed to the pressure distillation, if appropriate together with other return streams.

The exceptionally high efficiency of the interconnection according to the invention of the apparatuses mentioned, which is explained in detail in the following text, is surprising and has not been previously described in the literature. In contrast, complicated operations which are significantly more susceptible to interference with respect to side reactions, such as those operations discussed above and described in EP 523 728, have been proposed. The outstanding manner, which is particularly advantageous from energy aspects and therefore preserves resources, in which the pressure distillation fits into the overall process concept when this has not been optimized as an isolated process step, as described in the literature cited, but, as corresponds to the process according to the invention, is employed in combination with recycling steps for useful substances, such as, in particular, the methanol to be recycled, is particularly surprising.

Another advantage of the process according to the invention is that a particularly high efficiency of the overall process is achieved by the preferred use of carbon dioxide as the inert or carrier gas. While processes for the preparation of dimethyl carbonate based on methyl nitrite and carbon monoxide which employ catalysts of the type described, for example, in Patent Applications EP 425 197, EP 464 460, EP 503 091, EP 503 618 and EP 523 728, as all the examples cited there demonstrate, rely on the use of nitrogen as the inert or carrier gas, the new catalysts mentioned, which are described, for example, in Patent Application EP 523 508, EP 538 676, EP 559 001, EP 558 996 and EP 581 240 and which are preferably, but not exclusively, also used in the process according to the invention, are suitable above all for use in the presence of carbon dioxide as the inert or carrier gas. On the basis of the completely surprising observation that the limit for the flammability of the reactant or product gas mixture in the gas circulations typical of the process is about 30–50 mol % when carbon dioxide is used as the inert or carrier gas, but is significantly higher, in particular about 50–80 mol % (depending on the nature and amount of the other components within the overall gas mixture), if nitrogen is used, a considerable economic advantage results for the process according to the invention for example from the fact that the usable volume content (total volume minus inert or carrier gas content) is higher in the case of the preferred use of carbon dioxide.

Within apparatus 1 (dimethyl carbonate synthesis, compare FIG. 3), the formation of dimethyl carbonate proceeds in accordance with reaction equation (1). For this, after passing through a heat exchanger which allows a defined temperature to be established, the circulating gas stream (d) which originates from apparatus 3 (methyl nitrite synthesis) and comprises the regenerated methyl nitrite is treated as stream (d1) with carbon monoxide (a) and, if appropriate (not contained in FIG. 3), batchwise or continuously, with other gaseous auxiliaries, such as, for example, small amounts of halogen or hydrogen halide, and is passed as feed gas stream (d2) into the apparatus 1 mentioned. The heat of reaction liberated in the course of the formation of dimethyl carbonate is to be removed completely or partly in this procedure.

Apparatus 1 is therefore, for example, a tube-bundle reactor which is cooled, for example, with hot water.

Apparatus 1 is preferably an apparatus which is divided into two reaction zones, within which apparatus the first reaction zone is designed as a tube-bundle reactor which is cooled, for example, with hot water and the second is designed as a downstream reactor operated adiabatically.

In another preferred variant, the apparatus 1 mentioned is designed as a flat bed reactor, which can be operated adiabatically with intermediate cooling or else isothermally. In a third preferred variant, apparatus 1 mentioned is a reactor operated adiabatically with intermediate cooling.

In principle, it may be of advantage to construct apparatus 1 in duplicate, so that when catalysts which require regular regeneration are employed, one of the reactors can be used for the preparation of dimethyl carbonate while the other is available for the regeneration procedure mentioned. Switching between these two reactors is carried out in a manner known per se.

Another embodiment of apparatus 1 which is possible in principle can be constructed such that portions of the catalyst used can be removed batchwise or continuously from one or more points of the reaction zone or the actual reactor and can be fed to an external working up, regeneration or reactivation or disposal operation, while worked up, regenerated, reactivated or fresh catalyst can be reintroduced, likewise batchwise or continuously, at one or more points into the reactor or reaction zone.

Within apparatus 2 (dimethyl carbonate scrubber/condenser, compare FIG. 3), the product gases (e) flowing out of the dimethyl carbonate synthesis are separated into condensable and non-condensable reaction products (f) and (h) under specified conditions (pressure, temperature, gas speed and the like). In addition, apparatus 2 is charged, if appropriate, with a part stream (b2) of the fresh methanol introduced into the overall process, which is fed into its upper region. The stream (f) obtained at the top of apparatus 2 is passed on, after diversion of the portion (f2) intended for removal from the circulation, as circulating stream (f1) to a heat exchanger which allows the desired entry temperature for further reaction within apparatus 3 (methyl nitrite synthesis) to be established. The stream (f3) heated in this way passes through the compressor and is combined as stream (f4) with stream (s1), which is composed of the inert gas subsequently introduced, preferably, and as shown in FIG. 3, nitrogen (s) and fresh nitric oxide (in FIG. 3 nitrogen monoxide) (r) subsequently introduced in, before it flows into the preparation of methyl nitrite as the feed gas stream (f5).

If appropriate, the portion of circulating gas (f2) removed from the circulation can be subjected to treatment by subsequent operations, such as are described, for example, in DE-A 3 834 065. Such an after-treatment can serve the purpose of, in particular, recovering the useful substances reining in the portion (f2) of the circulating gas stream which has been removed from the circulation, such as, for example, unreacted methyl nitrite, nitrogen monoxide or gaseous dimethyl carbonate, and recycling them to a suitable point in the dimethyl carbonate preparation process. At the same time, the release of toxic gaseous substances, such as, for example, methyl nitrite or nitrogen monoxide, to the environment is avoided in this manner.

Apparatus 2 is, for example, a tube-bundle heat exchanger which can be in a vertical or horizontal construction, a plate heat exchanger, a spiral flow heat exchanger, a spray-in condenser, a scrubber provided with a top condenser, a ribbed tube heat exchanger or a combination of the condenser or heat exchanger and scrubber types mentioned, for example a spray-in condenser with a downstream ribbed tube heat exchanger.

In a preferred embodiment, apparatus 2 is constructed as a spray-in condenser, that is to say as a special variant of a direct contact heat exchanger, with spray jets which are arranged in series and are charged with cold condensate via a circulation and in this manner allow two or more theoretical separation stages to be realized.

In another preferred embodiment, apparatus 2 is a scrubber provided with a top condenser, within which a number of more than three theoretical separation stages is realized.

Apparatus 2, for example as a scrubber, is particularly preferably operated such that the temperature corresponding to the boiling point of dimethyl carbonate under the given reaction pressure (for example about 128° C. under 3 bar) is established in the bottom region, so that methanol present in the crude product mixture can be separated off at this point chiefly in gaseous form as a part of the top stream (f) and essentially as an azeotrope with dimethyl carbonate from virtually pure liquid dimethyl carbonate, as the main constituent of the bottom stream (h).

Within apparatus 3 (methyl nitrite synthesis, compare FIG. 3), the formation or renewed formation of methyl nitrite takes place in accordance with, for example, one of reaction equations (2), (3) or (4). For this, the nitric oxides which function as methyl nitrite equivalents or precursors are reacted with oxygen (c) and methanol (fresh methanol and methanol return streams from the removal of methanol in apparatus 7 and from waste water distillation in apparatus 6) (b3, b4, m1, m3). The water thereby formed and any by-products formed, such as, for example, nitric acid, are removed from the bottom of apparatus (g), and the product gas mixture (d) comprising methyl nitrite is led off, after passing through a condenser at the top of the apparatus (not contained in FIG. 3), and is made available for the formation of dimethyl carbonate. The methanol introduced into apparatus 3 thus serves on the one hand as a reaction partner in the formation of methyl nitrite which takes place in accordance with one of reaction equations (2), (3) or (4), and on the other hand, in particular in the form of the part streams (b3, l, m1) introduced in the upper part of the apparatus and the reflux dripping back from the top condenser, as the wash liquid for removal of the water formed. The nitric oxides taking part in the reaction are essentially nitrogen monoxide, which is liberated in the course of the formation of dimethyl carbonate according to reaction equation (1) and is recycled, as a mixture with further gaseous components, such as, for example, the inert gas, and if appropriate gaseous reactants which have not reacted completely, such as, for example, carbon monoxide or methyl nitrite itself, in the sense of a circulatory process (compare also FIG. 1) in accordance with reaction equation (2) (f→f1→f3→f4). Losses, which are in principle possible, of methyl nitrite itself present within the overall circulatory process or of methyl nitrite equivalents or precursors, that is to say nitrogen monoxide, nitrogen dioxide, dinitrogen dioxide or dinitrogen tetroxide, can result due to undesirable side reactions or else due to removals from the circulation (f2). The undesirable side reactions mentioned can be, for example, the process, which proceeds to a minor extent, of the formation of nitric acid in accordance with reaction equation (4), or the possible formation of nitrogen or dinitrogen monoxide from nitrogen monoxide, as can be formulated, for example, in accordance with reaction equations (12) and (13).

$$2NO + 2\ CO \rightarrow N_2 + 2\ CO_2 \quad (12)$$

$$2\ NO + CO \rightarrow N_2O + CO_2 \quad (13)$$

Losses of the type mentioned can be compensated, for example, by adding to the overall process the deficient methyl nitrite itself or corresponding amounts of methyl nitrite equivalents or precursors, that is to say nitrogen monoxide, nitrogen dioxide, dinitrogen trioxide, dinitrogen tetroxide or mixtures of some of these components, batchwise or continuously, preferably continuously. In FIG. 3, this is done, for example, by common feeding in of the inert gas, nitrogen and nitrogen monoxide (s1), but the process according to the invention is not limited to this embodiment.

In general, it is unacceptable from ecological aspects to release waste waters comprising nitric acid without after-treatment, even if only small amounts are involved here. For this reason, the process according to the invention comprises a neutralization step, which is preferably operated continuously and in which a suitable base is used for trapping such nitric acid. In FIG. 3, sodium hydroxide solution, for example, is used for this purpose, but other bases, such as, for example, potassium hydroxide solution, milk of lime or aqueous solutions of sodium carbonate and sodium bicarbonate, are also suitable. After the base in question, for example sodium hydroxide solution (q), has been admixed to the bottom stream (g) of apparatus 3, a neutralized stream comprising essentially water and methanol is thus obtained and is passed on to apparatus 6 (waste water distillation).

The apparatus is, for example, a column-like scrubber which is provided with baffles, to improve the exchange of heat and matter, such as are usually used for thermal separation tasks. Such baffles which may be mentioned are, for example, packing, trays, such as, for example, bubble trays, perforated trays or valve trays, ordered packing or spray nozzles.

If appropriate, the lower region of the apparatus is equipped with a bottom evaporator, with the aid of which a defined bottom temperature can be established within certain limits, which are determined by the phase equilibria of the substances present in the bottom product.

Apparatuses which are in principle suitable and can be used for mixing the liquid and gaseous components or streams (b4, c, f5, m3) to be fed in at the lower end of apparatus 3 are static mixers, jet mixers, rotating mixers, one- and two-component nozzles, fluidized bed mixers, such as are marketed, for example, by Sulzer, mixing chambers, such as are marketed, for example, by Pfaudler, in-line full-turbulence tubes, HI mixers, such as are marketed, for example, by Toray, Komax mixing elements, helical mixers, Kennix mixers, tubes filled with packing, such as, for example, Raschig rings, and combinations of such elements. Feeding in of oxygen (c) preferably takes place in the lower part of apparatus 3. A part stream (b3) of the fresh methanol and the methanol return streams (l) and (m1) are passed in the liquid form into the upper part of the reactor. Another portion of the methanol (b4) and the methanol return stream (m3) are fed into the lower part of apparatus 3 separately or together with the overall stream (f5) formed from circulating gas to be recycled and the nitric oxide and inert gas streams freshly fed in. In FIG. 3, only one of the variants possible according to the invention is shown, in which the feeding in of the oxygen (c), the methanol part stream (b4) and the combined stream (f5) of circulating gas to be recycled, inert gas newly fed in and nitric oxide freshly fed in is carried out separately. However, the process according to the invention is in no way limited to this embodiment. In particular, if specific feeding units are used, such as, in particular, two-component nozzles and/or static mixers, and combinations of such elements, it is advantageous to introduce streams (f5) and/or (b4) and/or (m3) and the oxygen stream (c) together into the lower part of apparatus (3).

In a preferred embodiment, mixing of the liquid and gaseous components or streams (b4, c, f5, m3) to be fed in at the lower end of apparatus 3 mentioned is carried out by means of an effectively operating static mixer such as is marketed, for example, by Sulzer (SMX or SMV type). The use of such units is described, for example, in Ing. Tech. 51 (5), page 307 et seq. (1979) or Chem. Eng. Process 25, page 59 et seq. (1989).

In another preferred embodiment, one- or two-component nozzles or combinations of static mixers and one- or two-component nozzles are used for mixing the liquid and gaseous components or streams (b4, c, f5, m3) to be fed in at the lower end of apparatus 3.

Apparatus 4 (pressure distillation, compare FIG. 3) is a distillation column operated under a bottom pressure of about 1 to 25 bar, preferably 1 to 12 bar. It serves to split stream (h) into an azeotrope-like mixture comprising methanol and dimethyl carbonate which is removed at the top of the apparatus (k), and a bottom product (i), which also comprises the remaining high-boiling constituents, in particular dimethyl oxalate, and, after passage through a heat exchanger, which allows a certain temperature to be established, is passed on as stream (i1) to apparatus 5 (dimethyl carbonate distillation). The exact composition of the top product mentioned depends here, inter alia, on the absolute pressure under which the distillation has been carried out (compare DE-A 2 607 003 and JP 02-212 456).

Distillation columns which are usually used for thermal separation of mixtures of substances under pressure and which have a stripping and a rectifying section and have the required number of theoretical separation stages corresponding to the separation problem are in general suitable for the apparatus mentioned. Examples which may be mentioned are tray columns, packed columns and columns which contain ordered packing as baffles. Apparatuses which may be mentioned as preferred are packed columns and columns which contain ordered packing as baffles.

Apparatus 5 (dimethyl carbonate distillation, compare FIG. 3) is a distillation column which is charged with the bottom product (i1) of apparatus 4 (pressure distillation) and serves to separate off the desired reaction product, dimethyl carbonate (o), in a form which complies with the specification, from the bottom product (i), which essentially comprises dimethyl oxalate and other possible high-boiling constituents.

Distillation columns such as are mentioned for apparatus 4 are in general suitable for apparatus 5, but a pressure-resistant construction is not necessary.

Apparatus 6 (waste water distillation, compare FIG. 3) is a distillation column which is charged with the neutralized bottom discharge (g1) of apparatus 3 (methyl nitrite synthesis). The task of this column is to remove and recycle the methanol contained in stream (g1) in the form of the top stream (m), which is recycled in the form of part streams (m1) and (m3) into apparatus 3 (methyl nitrite synthesis) and as part stream (m2), combined with the top stream (n) from apparatus 7 (removal of methanol) to give the stream (n1) into apparatus 4 (pressure distillation). The actual waste water of the overall process (p) is obtained at the bottom of apparatus 6.

Distillation columns such as are mentioned for apparatus 4 and 5 are in general suitable for apparatus 6; however, a pressure-resistant construction is not necessary.

Apparatus 7 (removal of methanol, compare FIG. 3) is a distillation column which is operated under normal pressure or under reduced pressure. It serves to split the stream (k) obtained as the top product of distillation column 4 into an azeotrope comprising methanol and dimethyl carbonate, which is removed at the top of apparatus (n) and is fed back (n1) into distillation column 4, together with some of the methanol return stream (m2) obtained from distillation column 6 (waste water column), and a bottom discharge (l), which essentially comprises methanol and is recycled into the upper part of the methyl nitrite reactor (apparatus 3).

Distillation columns such as have been mentioned for apparatuses 4, 5 and 6 are in general suitable for apparatus 7; however, they are equipped for operation under reduced pressure.

The substance streams described in FIG. 3 and the associated pressure and temperature conditions such as are realized when carrying out the process according to the invention are described below.

The gas stream (d2) introduced into apparatus 1 in continuous operation in general has a temperature of 25° to 120° C., preferably 40° to 110° C., and a pressure of 1 to 5 bar, preferably 1.5 to 4 bar. It is in general composed of 4 to 16 mol % of carbon monoxide, 0 to 5 mol % of carbon dioxide, 5 to 25 mol % of methyl nitrite, 40 to 80 mol % of nitrogen, 1 to 10 mol % of methanol, 0 to 5 mol % of dimethyl carbonate, 0 to 5 mol % of nitrogen monoxide, 0 to 1 mol % of water and less than 5 mol % of various, usually highly volatile secondary components; preferably of 8 to 14 mol % of carbon monoxide, 0.5 to 3 mol % of carbon dioxide, 10 to 20 mol % of methyl nitrite, 50 to 75 mol % of nitrogen, 1.5 to 8 mol % of methanol, 0 to 2 mol % of dimethyl carbonate, 0.1 to 5 mol % of nitrogen monoxide, 0 to 0.5 mol % of water and less than 4 mol % of usually highly volatile secondary components.

The gas stream (e) leaving apparatus 1 in continuous operation in general has a temperature of 50° to 170° C., preferably 60° to 160° C., and a pressure of 1 to 5 bar, preferably 1.5 to 4 bar. It is in general composed of 0 to 13 mol % of carbon monoxide, 0 to 5 mol % of carbon dioxide, 0 to 20 mol % of methyl nitrite, 40 to 80 mol % of nitrogen, 1 to 10 mol % of methanol, 1 to 10 mol % of dimethyl carbonate, 3 to 15 mol % of nitrogen monoxide, 0 to 0.5 mol % of water and less than 5 mol % of various, usually highly volatile secondary components; preferably of 1 to 12 mol % of carbon monoxide, 0.5 to 3 mol % of carbon dioxide, 5 to 15 mol % of methyl nitrite, 50 to 75 mol % of nitrogen, 1.5 to 8 mol % of methanol, 2 to 8 mol % of dimethyl carbonate, 5 to 14 mol % of nitrogen monoxide, 0 to 0.5 mol % of water and less than 4 mol % of usually highly volatile secondary components.

The gas stream (f) leaving apparatus 2 in continuous operation in general has a temperature of 0° to 40° C., preferably 5° to 35° C., and a pressure of 1 to 5 bar, preferably 2 to 4 bar. It is in general composed of 0 to 13 mol % of carbon monoxide, 0 to 5 mol % of carbon dioxide, 0 to 20 mol % of methyl nitrite, 40 to 80 mol % of nitrogen, 0 to 10 mol % of methanol, 0 to 3 mol % of dimethyl carbonate, 3 to 15 mol % of nitrogen monoxide, 0 to 0.5 mol % of water and less than 5 mol % of various, usually highly volatile secondary components; preferably of 1 to 12 mol % of carbon monoxide, 0.5 to 3 mol % of carbon dioxide, 5 to 15 mol % of methyl nitrite, 50 to 75 mol % of nitrogen, 1 to 8 mol % of methanol, 0 to 2 mol % of dimethyl carbonate, 5 to 14 mol % of nitrogen monoxide, 0 to 0.5 mol % of water and less than 4 mol % of usually highly volatile secondary components.

The amount of the portion of the circulating gas removed from the circulation as gas stream (f2) in continuous operation is in general 0 to 7% by weight, preferably 0.1 to 5 % by weight, based on the top stream (f) of apparatus 2.

The main stream (f1) which remains after the gas stream (f2) has been removed from the circulation is fed into apparatus 3 after passing through a heat exchanger and a compressor, if appropriate (compare FIG. 3) with prior admixing of fresh nitric oxide and/or inert gas.

The rate at which the gaseous nitrogen monoxide, which is in general introduced at ambient temperature as stream (r), is fed into apparatus 3 (compare FIG. 3) in continuous operation is 0 to 3 mol %, preferably 0 to 1.5 mol %, based on the gas stream (f4). Instead of the nitrogen monoxide, it is in principle also possible to feed in equivalent amounts of nitrogen dioxide, dinitrogen trioxide, dinitrogen tetroxide, methyl nitrite or any desired mixtures of these substances.

The rate at which the gaseous nitrogen, which is in general introduced at ambient temperature as stream (s), is fed into apparatus (3) (compare FIG. 3 ) in continuous operation is 0 to 3 mol %, preferably 0 to 1.5 mol %, based on gas stream (f4).

The temperature of gas stream (f5) in continuous operation is in general 0° to 70° C., preferably 20° to 60° C., under a pressure of 1 to 5 bar, preferably 1.5 to 4 bar.

In continuous operation, the amount of methanol fed in via feed line (b4) is advantageously chosen such that the ratio of the amounts of substances between this methanol and the nitrogen monoxide contained in the gas stream (f5) fed in is 0.1 to 5, preferably 0.1 to 2. The temperature of the methanol fed in is in general 10° to 80° C., preferably 20° to 60° C.

The amount of methanol fed in via feed line (b3) in continuous operation is advantageously chosen such that the ratio of the amounts of substances between this methanol and the nitrogen monoxide contained in the gas stream (f5) fed in is 0.1 to 5, preferably 0.2 to 4. The temperature of the methanol fed in is in general 10° to 40° C., preferably 10° to 35° C.

In continuous operation, the amount of oxygen in general introduced at ambient temperature via feed line (c) is advantageously chosen such that the ratio of the amounts of substances between oxygen and the nitrogen monoxide contained in the gas stream (f5) fed in is 0.125 to 0.25, preferably 0.15 to 0.245.

The internal pressure of the apparatus 3 mentioned is in general 1 to 5 bar, preferably 1.5 to 4 bar, and its internal temperature can be varied within wide limits. The temperature profile over the entire length of the apparatus is established according to the amount, entry temperature and state of aggregation of the individual feeds, the total pressure, the conversion of the reactants introduced, the reflux of the top condenser and the energy supplied at the bottom of the apparatus.

The stream (h) leaving apparatus 2 as the bottom product and fed to apparatus 4 in general has a temperature of 10° to 150° C., preferably 20° to 140° C., and comprises 1 to 60 mol % of methanol, 20 to 99 mol % of dimethyl carbonate and, where appropriate, small amounts of high-boiling constituents, such as, for example, dimethyl oxalate, in addition to other components in an order of magnitude of less than 10 mol % in total, preferably less than 5 mol %.

The stream (i) leaving apparatus 4 as the bottom product in general has a temperature of 90° to 240° C., preferably 90° to 190° C., and in general comprises less than 0.1 mol % of methanol, preferably less than 0.05 mol % of methanol, more than 90 mol % of dimethyl carbonate, preferably more than 95 mol % of dimethyl carbonate, and, where appropriate, small amounts of high-boiling constituents, such as, for example, dimethyl oxalate, and other components in an order of magnitude of less than 10 mol % in total, preferably less than 5 mol %.

The stream (k) leaving apparatus 4 as the top product and fed to apparatus 7 in general has a temperature of 80° to 160° C., preferably 90° to 140° C., and in general comprises 55 to 97 mol % of methanol, 2 to 35 mol % of dimethyl carbonate, 0 to 15 mol % of water and, where appropriate, small amounts of low-boiling constituents.

The liquid stream (n) fed into apparatus 4 and introduced as the top stream from apparatus 7 has a temperature of 40° to 90° C., preferably 50° to 80° C., and comprises 50 to 90 mol % of methanol, 5 to 30 mol % of dimethyl carbonate and small amounts of low-boiling components in an order of magnitude of in general less than 10 mol %.

The stream (l) leaving apparatus 7 as the bottom stream and fed into apparatus 3 in general comprises more than 80 mol % of methanol, preferably more than 90 mol % of methanol, and small amounts of dimethyl carbonate and water.

Apparatus 6 (waste water distillation) is in general operated under a pressure of 0.5 to 2 bar, preferably 0.5 to 1.5 bar. The condensed top product (m) is obtained in continuous operation with a temperature of 15° to 50° C., preferably 15° to 35° C., and has a composition of 60 to 95 mol % of methanol, 1 to 35 mol % of dimethyl carbonate and 0 to 7 mol % of water, preferably 70 to 88 mol % of methanol, 2 to 30 mol % of dimethyl carbonate and 0 to 5 mol % of water.

The amount of methanol/dimethyl carbonate mixture recycled as part stream (m2) can be adjusted, according to the content of dimethyl carbonate, such that it comprises 0 to 90%, preferably 0 to 30%, of the total stream (m).

The amount of methanol/dimethyl carbonate mixture recycled as part stream (m1) can be adjusted according to the content of dimethyl carbonate such that it comprises between 0 and 100% of the total stream (m). The same applies to the amount of methanol recycled as part stream (m3).

The carbon monoxide in general fed in at ambient temperature as stream (a) is in general employed in the chemically pure form, but can contain foreign gases, depending on the type of preparation, such as, for example, small amounts of hydrogen (<0.1 mol %) or methane (<0.1 mol %). In continuous operation, it is fed in such that the ratio of the amounts of substances between carbon monoxide metered in and dimethyl carbonate produced is 1 to 1.2 and a constant concentration of carbon monoxide is present in gas stream (d2).

The dimethyl carbonate distilled in apparatus 5 has a purity of 99.0 to 99.9%, depending on the reflux/withdrawal ratio.

Another arrangement for variant (e1) is described as follows with the aid of FIG. 7:

Apparatus 1 is the same as that in FIG. 3. (y) is the batchwise or continuous feeding in of small amounts of gaseous auxiliaries (for example halogen or hydrogen halide). $CO_2$ is employed instead of $N_2$ as the inert gas.

Figure 7:
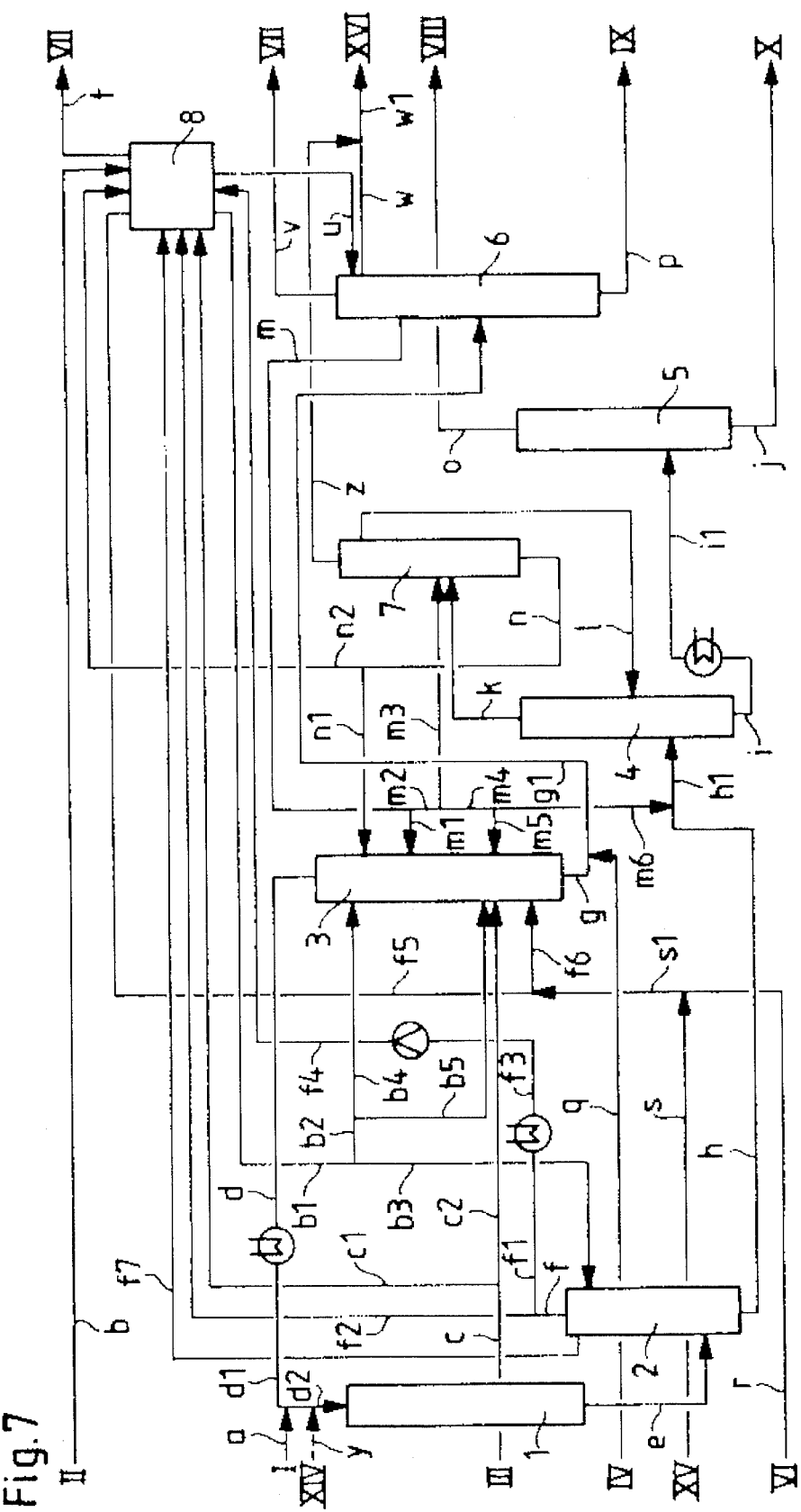

Apparatus 2 of FIG. 7 is essentially the same as that in FIG. 3. A part stream chiefly comprising methanol is fed via (b3) from apparatus arrangement 8 (working up of waste gas/recycling of useful substances/removal of secondary products from the circulation), that is to say from (b1), into the upper region of apparatus 2.

If appropriate, the gaseous stream (f) obtained at the top of apparatus 2 can be passed on, after diversion of the portion (f2) intended for removal from the circulation, as circulating stream (f1) to a heat exchanger (contained in FIG. 7), which allows the desired entry temperature for the subsequent reaction to be established. The stream (f3) thus heated passes through the compressor and is introduced as stream (f4) into apparatus arrangement 8. Depending on the mode of operation of the overall plant, such a prior heat exchanger can also be dispensed with if appropriate. Stream (f5), which comprises, as essential constituents, the fresh methanol fed to the process and dissolved methyl nitrite, is removed from this apparatus arrangement 8, the construction and functioning of which is explained below. The stream (f5) mentioned is combined with stream (s1), which is composed of inert gas subsequently added, preferably, and as shown in FIG. 7, carbon dioxide (s), and fresh nitric oxide (in FIG. 7 nitrogen monoxide) (r) subsequently added before it flows as feed gas stream (f6) into the methyl nitrite preparation. A liquid stream (f7) is furthermore removed at the top of the apparatus 2 mentioned and is passed into apparatus arrangement 8 (compare the description below).

If appropriate, the portion of circulating gas (f2) removed from the circulation can also be subjected to treatment by other suitable subsequent operations, such as are described, for example, in DOS 3 834 065, instead of as in the embodiment described below, which comprises use of apparatus arrangement 8. Such an after-treatment usually serves in particular the aim of recovering useful substances remaining in the portion (f2) of the circulating gas stream removed from the circulation, such as, for example, unreacted methyl nitrite, nitrogen monoxide or gaseous dimethyl carbonate, and recycling them to the dimethyl carbonate preparation process. At the same time, the release of toxic gaseous substances, such as, for example, methyl nitrite or nitrogen monoxide, to the environment is avoided in this manner. In this context, the process according to the invention is associated only by way of example and not necessarily and irretrievably with the working up of waste gas/recycling of useful substances/removal of secondary products from the circulation, as is achieved with the aid of apparatus arrangement 8, but in principle can also be combined with other conceivable embodiments of waste gas and process gas treatment.

The construction of apparatus 2 is the same as that described above in connection with FIG. 3, as is its mode of operation.

Within apparatus 3 (methyl nitrite synthesis, compare FIG. 7), formation or re-formation of the methyl nitrite takes place in accordance with, for example, one of reaction equations (2), (3) or (4). For this, the nitric oxides which function as methyl nitrite equivalents or precursors are reacted with oxygen (c2) and methanol (methanol charged with dissolved methyl nitrite from apparatus arrangement 8 and methanol return streams from the removal of methanol in apparatus 7 and from the waste water distillation in apparatus 6) (b4, b5, m1, m5, n1). The water thereby formed and any by-products formed, such as, for example, nitric acid, are removed as stream (g) at the bottom of the apparatus 3 mentioned, and, after passing through a condenser at the top of the apparatus (not contained in FIG. 7), the product gas mixture (d) comprising methyl nitrite is led off and made available again for the formation of dimethyl carbonate. The methanol introduced into apparatus 3 thus serves on the one hand as a reaction partner in the formation of methyl nitrite which takes place in accordance with one of reaction equations (2), (3) or (4), and on the other hand, in particular in the form of the part streams (b4, m1, n1) introduced at the upper part of the apparatus and the reflux which drips back from the top condenser, as the wash liquid for removal of the water formed. The nitric oxides entering into the reaction are essentially nitrogen monoxide, which is liberated in the course of the formation of dimethyl carbonate in accordance with reaction equation (1) and, as a mixture with other gaseous components, such as, for example, the inert gas and, if appropriate, gaseous reactants which have not reacted completely, such as, for example, carbon monoxide or methyl nitrite itself, is recycled in the context of a circulatory process (compare also FIG. 1) in accordance with reaction equation (2), the route (f→f1→f3→f4→f5) being passed through. Losses, which are in principle possible, of methyl nitrite itself present within the entire circulatory process or of methyl nitrite equivalents or precursors, that is to say nitrogen monoxide, nitrogen dioxide, dinitrogen dioxide or dinitrogen tetraoxide, may result due to undesirable side reactions, such as may occur in principle within apparatus 3, or else due to removals from the circulation (p, t, v, w1). The undesirable side reactions mentioned can be, for example, the process, which proceeds to a minor extent, of the formation of nitric acid in accordance with reaction equation (4) or the possible formation of nitrogen or dinitrogen monoxide from nitrogen monoxide, such as can be formulated, for example, in accordance with reaction equations (12) and (13) (see above).

Losses of the type mentioned can be compensated, for example, by adding to the overall process the deficient methyl nitrite itself, which can be prepared in a manner known per se in an apparatus connected upstream, or else corresponding amounts of methyl nitrite equivalents or precursors, that is to say nitrogen monoxide, nitrogen dioxide, dinitrogen trioxide, dinitrogen tetraoxide or mixtures of some of these components, batchwise or continuously, preferably continuously. In FIG. 7, this is done, for example, by feeding in the inert gas, carbon dioxide and nitrogen monoxide together (s1) but the process according to the invention is not limited to this embodiment.

In general, it is unacceptable from ecological aspects to release waste waters comprising nitric acid without after-treatment, even if only small amounts are involved here. For this reason, the process according to the invention comprises a neutralization step, which is preferably operated continuously and in which a suitable base is used for trapping any nitric acid formed. In FIG. 7, sodium hydroxide solution, for example, is used for this purpose, but other bases, such as, for example, potassium hydroxide solution, milk of lime or aqueous solutions of sodium carbonate and sodium bicarbonate, are also possible. After the base in question, for example sodium hydroxide solution (q), has been admixed to the bottom stream (g) of apparatus 3, a neutralized stream (g1) essentially comprising water and methanol is thus obtained, and is passed on to apparatus 6 (waste water distillation).

The construction of apparatus 3 is that described in association with FIG. 3.

The feeding in of oxygen (c2) preferably takes place in the lower part of apparatus 3. A part stream (b4) of the stream (b1) which is introduced from apparatus 8 and is charged with dissolved methyl nitrite and comprises the methanol fed to the process, and the methanol return streams (n1) and (m1) are introduced in liquid form into the upper part of the reactor. Another portion of the methanol (b4) and the return streams (m5) comprising methanol are fed into the lower part of apparatus 3 separately or together with the overall stream (f6) formed from circulating gas to be recycled and the nitric oxide and inert gas streams freshly fed in. In FIG. 7, only one of the variants possible according to the invention is shown, in which the oxygen (c2), the methanol part streams (b4) and (m5) and the combined stream (f6) of circulating gas to be recycled, inert gas newly fed in and nitric oxide freshly fed in are carried out separately for reasons of clarity. However, the process according to the invention is in no way limited to this embodiment. In particular, if special feeding units are used, such as, in particular, two-component nozzles and/or static mixers and combinations of such elements, it is advantageous for the streams (f6) and/or (b5) and/or (m5) and the oxygen stream (c2) to be introduced together into the lower part of apparatus 3.

In a preferred embodiment, the liquid and gaseous components or streams (b5, c2, f6, m5) to be fed in at the lower end of the apparatus 3 mentioned are mixed by means of an effectively operating static mixer such as is marketed, for example, by Sulzer (SMX or SMV type). The use of such units is described, for example, in Ing. Tech. 51 (5), page 307 et seq. (1979) or in Chem. Eng. Process 25, page 59 et seq. (1989).

In another preferred embodiment, one-component or two-component nozzles or combinations of static mixers and one- or two-component nozzles are used for mixing the liquid and gaseous components or streams (b5, c2, f6, m5) to be fed in at the lower end of the apparatus 3 mentioned.

The mode of operation and construction of apparatuses 4 and 5 correspond to the description in connection with FIG. 3.

Figure 9:
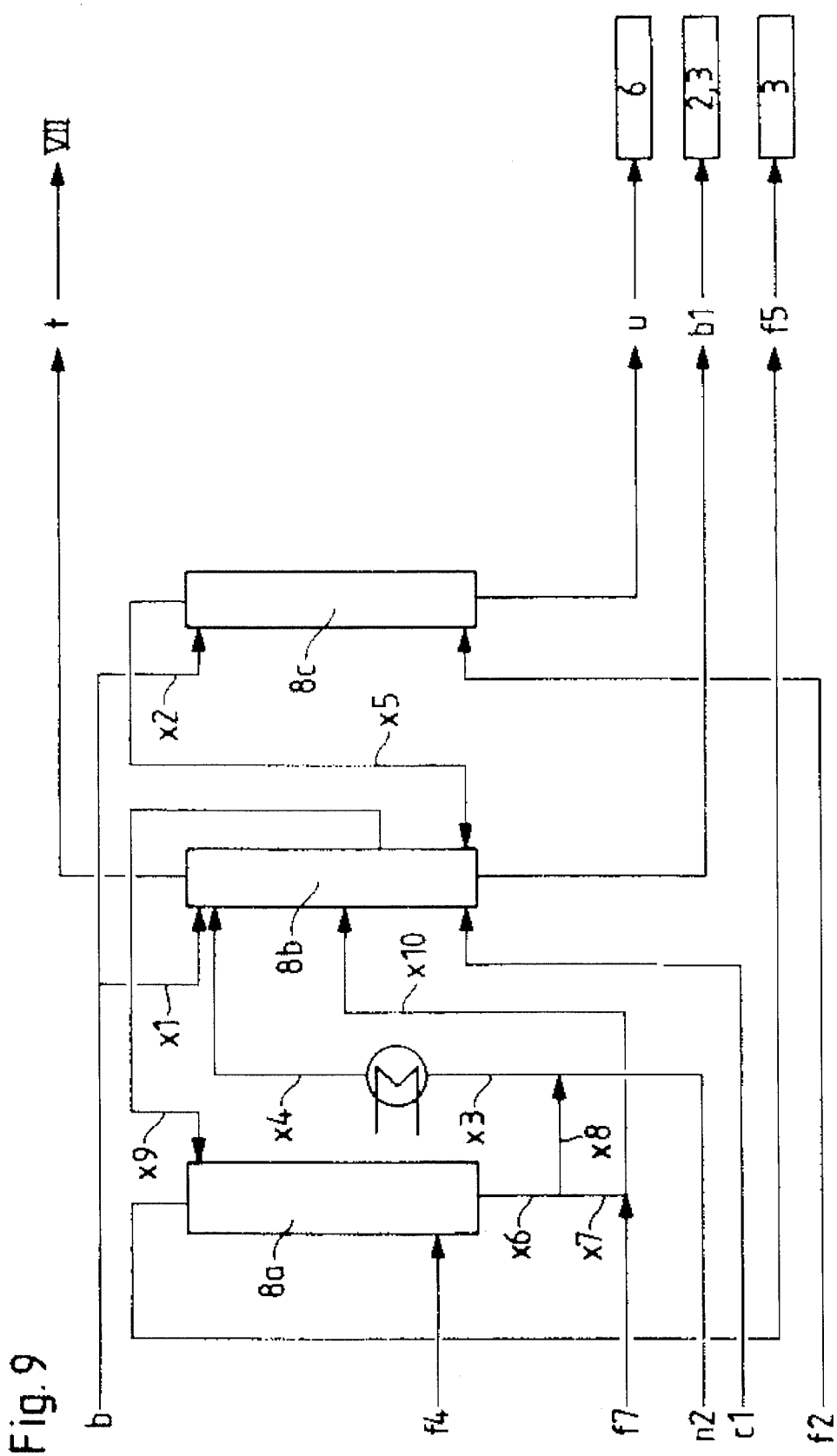

Apparatus 6 (waste water distillation, compare FIG. 7) is a distillation column which is charged with the neutralized bottom discharge (g1) of apparatus 3 (methyl nitrite synthesis) and with the stream (u) from apparatus arrangement 8 (bottom stream of the low-boiling constituents scrubber 8c of the working up of waste gas/recycling of useful substances/removal of by-products from the circulation, compare FIG. 9). The task of this column is essentially removal and recycling of the methanol contained in the stream (g1) mentioned and if appropriate dimethyl carbonate also present as side stream (m) removed from the upper part, which is recycled in the form of part streams (m1) and (m5) into apparatus 3 (methyl nitrite synthesis), as part stream (m3) to apparatus 7 (methanol distillation) and if appropriate also as part stream (m6), combined with stream (h) to give stream (h1), into apparatus 4 (pressure distillation). The actual waste water of the overall process (p) is obtained at the bottom of apparatus 6.

Distillation columns such as have been described above for apparatuses 4 and 5 are in general suitable for the apparatus 6 mentioned; however, a pressure-resistant construction is not necessary.

Depending on the operating conditions chosen, it may be appropriate in the event of problems due to varying qualities of the feed substances or for other reasons to remove a part stream (w) (compare FIG. 7) from the upper part of apparatus 6 and to subject it to a particular treatment, for example removal of by-products (not a component of the process circulation shown in FIG. 7), it being possible for the useful substances recovered by this working up to be fed back into the process, if appropriate, at another suitable point.

Apparatus 7 (methanol removal, compare FIG. 7) is a distillation column operated under normal pressure or under reduced pressure. It serves to split the stream (k) obtained as the top product of distillation column 4 into an azeotrope (l), which comprises methanol and dimethyl carbonate, is removed at the top of the apparatus and is recycled to distillation column 4, and to a bottom discharge (n), which essentially comprises methanol and is passed on as part stream (n1) into the upper part of the methyl nitrite reactor (apparatus 3) and as spart stream (n2) into apparatus arrangement 8 (working up of waste gas/recycling of useful substances/removal of by-products from the circulation). It is additionally fed by part stream (m3) which originates from the waste water distillation and comprises methanol.

Depending on the mode of operation, it may be appropriate, depending on problems due to varying qualities of the feed substances or for other reasons, for the azeotrope comprising methanol and dimethyl carbonate to be removed as stream (k) from the upper region of apparatus 7, and additionally to remove at the top of the apparatus mentioned a gaseous stream (z) which is particularly rich in low-boiling by-products and which can be fed, if appropriate, to another working up operation (compare also the description of apparatus 6, stream (w) there). This variant has also been included in FIG. 7.

Distillation columns such as have been mentioned for apparatuses 4, 5 and 6 are in general suitable for the apparatus 7 mentioned; however, they are equipped for operation under reduced pressure.

Figure 8:
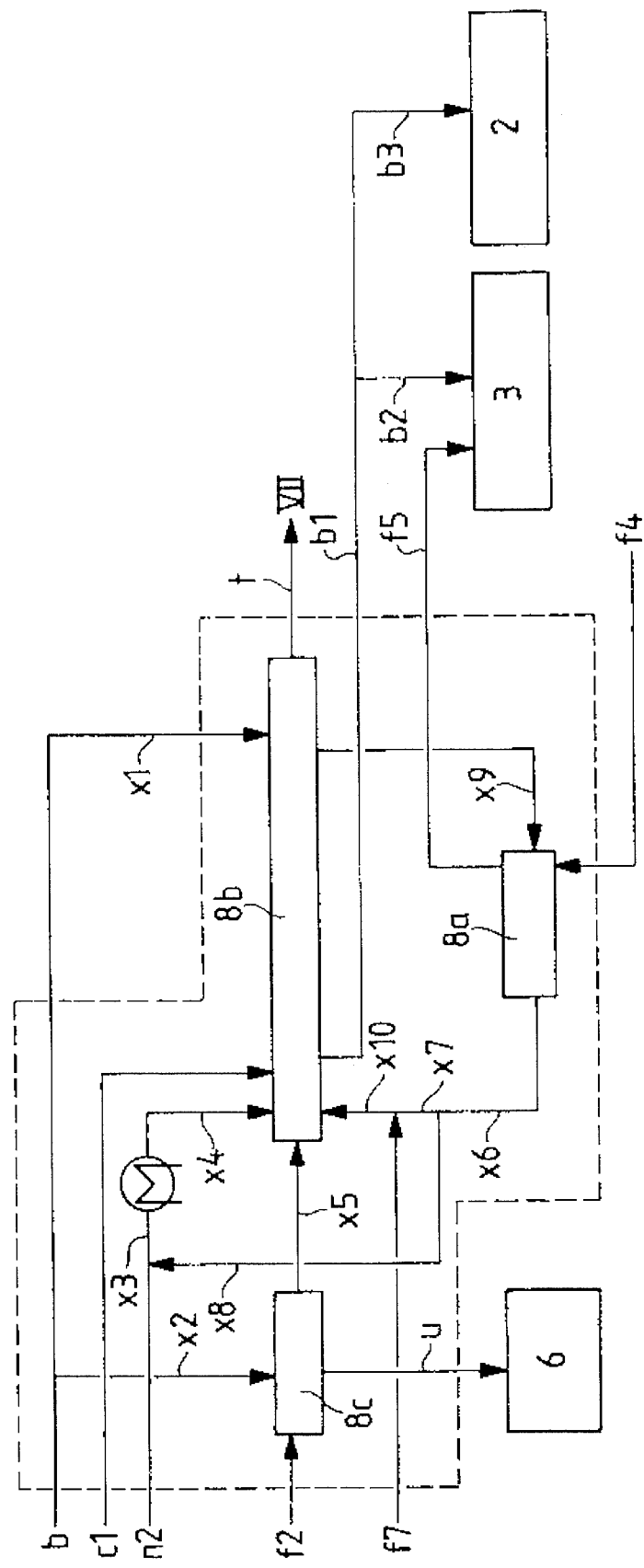

FIG. 8 shows by way of example, in the form of a block diagram, how the task complex of working up of waste gas/recycling of useful substances/removal of by-products from the circulation can be achieved with the aid of apparatus arrangement 8. It is also shown merely by way of example in FIG. 9 how this concept can be realized concretely. These are individual or, where appropriate, also partly interconnected apparatuses.

The part stream (f2) diverted from the circulating gas stream (f) leaving apparatus 2 is first introduced into the lower region of a low-boiling constituents scrubber (apparatus 8c, compare FIGS. 8 and 9), into the upper region of which is/are fed a part stream (x2) of the methanol (b) freshly fed to the process and/or (not contained in FIG. 7 or FIG. 9) a portion from the stream (n2) brought from apparatus 7. The stream (u) emerging at the bottom of the apparatus 8c mentioned is fed to the waste water column (apparatus 6 in FIG. 7), while the gaseous mixture obtained at the top of the apparatus is fed as stream (x5) into the lower region of apparatus 8b (methyl nitrite after-reactor/methanol waste gas scrubber, see below for the description).

Apparatus 8c is, for example, a column-like scrubber which is equipped, if appropriate, with a top condenser and, to improve the exchange of heat and matter, is provided with baffles such as are usually used in thermal separation tasks, and within which a number of more than two theoretical separation stages is realized. Baffles of this type which may be mentioned are, for example, packing, trays, such as, for example, bubble trays, perforated trays or valve trays, ordered packing or spray nozzles.

If appropriate, the lower region of the apparatus is equipped with a bottom evaporator, with the aid of which a defined bottom temperature can be established within certain limits determined by the phase equilibria of the substances present in the bottom product.

Most of the circulating gas stream (f4) is introduced into the lower region of apparatus 8a (methyl nitrite desorber, compare FIGS. 8 and 9), into the upper region of which the part stream (x9) which comprises methanol and dissolved methyl nitrite and is brought from apparatus 8b is fed. Stream (f5) is obtained at the top of the apparatus 8a mentioned and is passed on to apparatus 3, while the bottom stream (x6) obtained is divided into the two part streams (x7) and (x8). Part stream (x7) is combined with stream (f7) brought from apparatus 2 to give stream (x10) and is fed directly into apparatus 8b (for description, see below), while part stream (x8) is combined with part stream (n2) brought from apparatus 7 to give stream (x3). This is introduced, if appropriate after passing through a heat exchanger which allows a defined entry temperature to be established, as stream (x4) into apparatus 8b (for the description, see below).

Numerous apparatuses of widely varying design are in principle suitable for apparatus 8a according to its function as a methyl nitrite desorber. For example, apparatus 8a can be a tube-bundle heat exchanger, which can be in vertical or horizontal construction, a falling film evaporator, a spray-in condenser, a scrubber provided with a top condenser and/or a bottom evaporator, a ribbed tube heat exchanger or a combination of the condenser or heat exchanger and scrubber types mentioned, for example a spray condenser with a downstream ribbed tube heat exchanger. Apparatuses which are furthermore suitable for the apparatus 8a mentioned are also distillation columns which are usually used for thermal separation of mixtures of substances under normal pressure or increased pressure, which have, where appropriate, a stripping and a rectifying section and which have the required number of theoretical separation stages according to the separation problem. Examples which may be mentioned are tray columns, packed columns and columns which contain ordered packing as baffles. Packed columns and columns which contain ordered packing as baffles may be mentioned as preferred.

Apparatus 8b functions as a methyl nitrite after-reactor and methanol waste gas scrubber (compare FIGS. 8 and 9). It can be realized as a constructional unit, as described in FIG. 9 and explained below, but if appropriate also in the form of two apparatuses which are separated from one another.

The more highly positioned part of the apparatus 8b mentioned (methanol waste gas scrubber part) essentially functions as a scrubber. Streams (x1) and (x4) which chiefly comprise methanol are fed into its upper region. The central region of the apparatus 8b mentioned contains suitable baffles, from which the liquid which collects there can be removed completely or partly as stream (x9) and passed to apparatus 8a. Gas rising from the lower part of the apparatus 8b mentioned (methyl nitrite after-reactor part) is washed with stream (x10) introduced into the central region of the apparatus 8b mentioned, whereby useful substances contained in it can be dissolved out and recycled to the process. Inert gases, such as, for example, methane, hydrogen and any low-boiling by-products, such as, for example, methyl chloride, leave the total apparatus as top stream (t) and can be fed, for example, to the waste gas combustion.

The lower part of the apparatus 8b mentioned essentially functions as a methyl nitrite reactor, similarly to apparatus 3 described above. Gas stream (x5) which comprises nitrogen monoxide and is brought from apparatus 8c is fed, like oxygen stream (c1) into the lower region of the methyl nitrite after-reactor part, while stream (x10), which comprises methanol, is introduced into the upper region, thus, approximately into the central region of the overall apparatus. Stream (b1) obtained at the bottom of the overall apparatus is passed on to apparatuses 2 and 3 (compare FIG. 7).

The upper part of the apparatus 8b mentioned (methanol waste gas scrubber part) is, for example, a column-like scrubber which is equipped, if appropriate, with a top condenser and, to improve the exchange of heat and matter, is provided with baffles such as are usually used in thermal separation tasks, and within which a number of more than two theoretical separation stages is realized. Such baffles which may be mentioned are, for example, packing, trays, such as, for example, bubble trays, perforated trays or valve trays, ordered packing or spray nozzles.

The lower part of the apparatus 8b mentioned (methyl nitrite after-reactor) is, for example, a column-like scrubber which, to improve the exchange of heat and matter, is provided with baffles such as are usually used in thermal separation tasks. Such baffles which may be mentioned are, for example, packing, trays, such as, for example, bubble trays, perforated trays or valve trays, ordered packing or spray nozzles.

If appropriate, the lower region of the apparatus is equipped with a bottom evaporator, with the aid of which a defined bottom temperature can be established within certain limits determined by the phase equilibria of the substances present in the bottom product.

Gaseous streams (c1) and (x4) can be fed into the methyl nitrite after-reactor part of apparatus 8b separately or as a mixture. Apparatuses which are in principle suitable and can be used for mixing the gaseous components and streams (c1, x5) to be fed in at the lower end of the apparatus 8b mentioned are static mixers, jet mixers, rotating mixers, one-component nozzles, fluidized bed mixers, such as are marketed, for example, by Sulzer, mixing chambers, such as are marketed, for example, by Pfaudler, in-line full turbulence tubes, HI mixers, such as are marketed, for example, by Toray, Komax mixing elements, spiral mixers, Kennix mixers, tubes filled with packing, such as, for example, Raschig rings, and combinations of such elements. Oxygen (c1) is preferably fed into the lower part of apparatus 8b.

The substance streams described in FIGS. 7, 8 and 9 and the associated pressure and temperature conditions realized when carrying out the process according to the invention are stated below.

The gas stream (d2) passed into apparatus 1 in continuous operation in general has a temperature of 25° to 120° C., preferably 50° to 110° C., and a pressure of 1 to 5 bar, preferably 1.5 to 4 bar. In general, it comprises 4 to 25 mol % of carbon monoxide, 30 to 80 mol % of carbon dioxide, 5 to 40 mol % of methyl nitrite, 0 to 5 mol % of nitrogen, 1 to 10 mol % of methanol, 0 to 5 mol % of dimethyl carbonate, 0.1 to 5.0 mol % of nitrogen monoxide, 0 to 1 mol % of water and less than 15 mol % of various, usually highly volatile secondary components, preferably 5 to 20 mol % of carbon monoxide, 35 to 70 mol of carbon dioxide, 10 to 35 mol % of methyl nitrite, 0 to 4 mol % of nitrogen, 2 to 9 mol % of methanol, 0 to 4 mol % of dimethyl carbonate, 0.5 to 5.0 mol % of nitrogen monoxide, 0 to 0.5 mol % of water and 1 to 12 mol % of various, usually highly volatile secondary components.

The stream (y) admixed to the stream (d2), where appropriate, before entry into apparatus 1 comprises, as the activator, hydrogen halide and/or methyl chloroformate and/or halogen and/or further substances which contain halogen acting activating under the reaction conditions, preferably hydrogen chloride and/or chlorine, in pure or dilute form and is metered in such that the gas stream entering apparatus 1 comprises 0 to 3000 ppm, preferably 10 to 1000 ppm, of these components.

The gas stream (e) leaving apparatus 1 in continuous operation in general has a temperature of 50° to 170° C., preferably 60° to 160° C., and a pressure of 1 to 5 bar, preferably 1.5 to 4 bar. In general, it comprises 0 to 12 mol % of carbon monoxide, 30 to 80 mol % of carbon dioxide, 0 to 20 mol % of methyl nitrite, 0 to 5 mol % of nitrogen, 2 to 12 mol % of methanol, 3 to 25 mol % of dimethyl carbonate, 5 to 40 mol % of nitrogen monoxide, 0 to 0.5 mol % of water and less than 16 mol % of various, usually highly volatile secondary components, preferably 1 to 10 mol % of carbon monoxide, 35 to 70 mol % of carbon dioxide, 1 to 19 mol % of methyl nitrite, 0 to 5 mol % of nitrogen, 3 to 10 mol % of methanol, 5 to 20 mol % of dimethyl carbonate, 5 to 35 mol % of nitrogen monoxide, 0 to 0.5 mol % of water and less than 13 mol % of various, usually highly volatile secondary components.

The gas stream (f) leaving apparatus 2 in continuous operation in general has a temperature of 0° to 50° C., preferably 5° to 40° C., and a pressure of 1 to 5 bar, preferably 1.5 to 4 bar. In general, it comprises 0 to 15 mol % of carbon monoxide, 30 to 80 mol % of carbon dioxide, 0 to 20 mol % of methyl nitrite, 0 to 5 mol % of nitrogen, 0 to 12 mol % of methanol, 0 to 5 mol % of dimethyl carbonate, 5 to 45 mol % of nitrogen monoxide, 0 to 1 mol % of water and less than 20 mol % of various, usually highly volatile secondary components, preferably 1 to 12 mol % of carbon monoxide, 35 to 70 mol % of carbon dioxide, 3 to 15 mol % of methyl nitrite, 0 to 5 mol % of nitrogen, 3 to 10 mol % of methanol, 0 to 3 mol % of dimethyl carbonate, 5 to 40 mol % of nitrogen monoxide, 0 to 0.5 mol % of water and less than 14 mol % of various, usually highly volatile secondary components.

The amount of the portion of circulating gas removed from the circulation as gas stream (f2) in continuous operation is in general 0 to 7% by weight, preferably 0.1 to 5% by weight, based on the gaseous top stream (f) of apparatus 2.

The liquid stream (f7) removed in the upper region of apparatus 2 comprises 20 to 90% by weight of methanol, 10 to 80% by weight of dimethyl carbonate and less than 30% by weight of other, usually less volatile, dissolved constituents, preferably 25 to 60% by weight of methanol, 40 to 75% by weight of dimethyl carbonate and less than 20% of other, usually less volatile dissolved components.

The gaseous main stream (f1) which remains after the gas stream (f2) has been removed from the circulation is fed, after passing through a heat exchanger as stream (f3) and subsequently a compressor as stream (f4) to apparatus arrangement 8. The stream (f4) mentioned then has a temperature of 10° to 70° C., preferably 20° to 60° C., and a pressure of 1 to 5 bar, preferably 1.5 to 4 bar.

The stream (f5) recycled from apparatus arrangement 8 in general has a temperature of 0° to 70° C., preferably 20° to 60° C., and a pressure of 1 to 5 bar, preferably 1.5 to 4 bar. In general, it comprises 0 to 15 mol % of carbon monoxide, 30 to 80 mol % of carbon dioxide, 0 to 20 mol % of methyl nitrite, 0 to 5 mol % of nitrogen, 0 to 16 mol % of methanol, 0 to 5 mol % of dimethyl carbonate, 5 to 45 mol % of nitrogen monoxide, 0 to 1 mol % of water and less than 20 mol % of various, usually highly volatile secondary components, preferably 1 to 12 mol % of carbon monoxide, 35 to 70 mol % of carbon dioxide, 3 to 15 mol % of methyl nitrite, 0 to 5 mol % of nitrogen, 3 to 10 mol % of methanol, 0 to 3 mol % of dimethyl carbonate, 5 to 40 mol % of nitrogen monoxide, 0 to 0.5 mol % of water and less than 14 mol % of various, usually highly volatile secondary components.

The stream (h) leaving apparatus 2 as the bottom product in general has a temperature of 10° to 150° C., preferably 20° to 140° C., and in general comprises 0 to 40 mol % of methanol, 20 to 99 mol % of dimethyl carbonate and, where appropriate, small amounts of water, high-boiling constituents, such as, for example, dimethyl oxalate, and other components in an order of magnitude of less than 5 mol %.

The feed rate of the gaseous nitrogen monoxide, which is in general introduced as stream (r) at ambient temperature, into apparatus 3 (compare FIG. 7) in continuous operation is 0 to 3 mol %, preferably 0 to 1.5 mol %, based on the gas stream (f5). Instead of the nitrogen monoxide, it is in principle also possible for equivalent amounts of nitrogen dioxide, dinitrogen trioxide, dinitrogen tetroxide, methyl nitrite or any desired mixtures of these substances to be fed in.

The feed rate of the gaseous carbon dioxide in general introduced as stream (s) at ambient temperature into apparatus 3 (compare FIG. 7) in continuous operation is 0 to 3 mol %, preferably 0 to 1.5 mol %, based on gas stream (f5).

The gas stream (f6) which results from joining streams (s1) and (f5) in continuous operation in general has a temperature of 0° to 70° C., preferably 20° to 60° C., and a pressure of 1 to 5 bar, preferably 1.5 to 4 bar.

The stream (b2) brought from apparatus arrangement 8 is in general such that the ratio of the amounts of substances between the methanol contained therein and the nitrogen monoxide contained in gas stream (f6) is 1 to 10, preferably 1 to 5. The stream (b2) mentioned is separated into part streams (b4) and (b5), if appropriate, part stream (b4) in general comprising 50 to 100%, preferably 70 to 100%, of stream (b2).

In a specific embodiment of the process according to the invention, the amount of methanol fed in via feed (b5) in continuous operation is advantageously chosen such that the ratio of the amounts of substances between this methanol and the nitrogen monoxide contained in the gas stream (f6) fed in is 0.1 to 2.5, preferably 0.1 to 1.5.

In continuous operation, the amount of oxygen in general introduced at ambient temperature via feed (c2) is advantageously chosen such that the ratio of the amounts of substances between oxygen and the nitrogen monoxide contained in the gas stream (f6) fed in is 0.15 to 0.26, preferably 0.20 to 0.25.

The internal pressure of the apparatus 3 mentioned is in general 1 to 5 bar, preferably 1.5 to 4 bar, and its internal temperature can be varied within wide limits. The temperature profile over the entire length of the apparatus is established as a function of the amount, entry temperature and state of aggregation of the individual feeds, the overall pressure, the conversion of the reactants introduced, the reflux of the top condenser and the energy supplied to the bottom of the apparatus.

The liquid stream (g) which leaves apparatus 3 as the bottom product in continuous operation in general has a temperature of 10° to 150° C., preferably 20° to 140° C., and in general comprises 0 to 70 mol % of methanol, 10 to 99 mol % of water, 0 to 20 mol % of dimethyl carbonate and, where appropriate, small amounts of nitric acid and other dissolved components.

The stream (q) which is in general introduced at ambient temperature and comprises a base for the purpose of neutralization is in general chosen such that it is capable of neutralizing the acid contained in the stream (g) mentioned.

The stream (d) leaving apparatus 3 as the top product in continuous operation in general has a temperature of 0° to 60° C., preferably 10° to 50° C., and a pressure of 1 to 5 bar, preferably 1.5 to 4 bar, and in general comprises 0 to 20 mol % of carbon monoxide, 30 to 80 mol % of carbon dioxide, 5 to 40 mol % of methyl nitrite, 0 to 5 mol % of nitrogen, 1 to 12 mol % of methanol, 0 to 5 mol % of dimethyl carbonate, 0.1 to 5 mol % of nitrogen monoxide, 0 to 1 mol % of water and less than 15 mol % of various, usually highly volatile secondary components, preferably 5 to 15 mol % of carbon monoxide, 35 to 70 mol % of carbon dioxide, 10 to 35 mol % of methyl nitrite, 0 to 4 mol % of nitrogen, 2 to 9 mol % of methanol, 0 to 4 mol % of dimethyl carbonate, 0.5 to 5 mol % of nitrogen monoxide, 0 to 0.5 mol % of water and 1 to 12 mol % of various, usually highly volatile secondary components.

If appropriate, the stream (d) mentioned is brought to the temperature desired for feeding it into apparatus 1 with the aid of a heat exchanger. The carbon monoxide in general fed as stream (a) at ambient temperature to the stream (d1) obtained in this manner is in general employed in chemically pure form, but may comprise foreign gases, such as, for example, small amounts of hydrogen (<0.1 mol %) or methane (<0.1 mol %), depending on the method of preparation. In continuous operation, it is fed in such that the ratio of the amounts of substances between the carbon monoxide metered in and the dimethyl carbonate produced is 1 to 1.2 and a concentration of the carbon monoxide in gas stream (d2) which is constant with respect to time exists.

Apparatus 6 (waste water distillation) is in general operated under a pressure of 0.5 to 2 bar, preferably 0.5 to 1.5 bar. The liquid stream (m) removed in the upper region of this apparatus is obtained in continuous operation with a temperature of 25° to 80° C., preferably 40° to 75° C., and in general comprises 60 to 95 mol % of methanol, 1 to 35 mol % of dimethyl carbonate and 0 to 7 mol % of water, preferably 70 to 95 mol % of methanol, 2 to 30 mol % of dimethyl carbonate and 0 to 5 mol % of water.

The amount of liquid mixture recycled as part stream (m3) of the stream (m) mentioned can be chosen within wide limits, depending on the content of dimethyl carbonate, such that it comprises 0 to 100%, preferably 30 to 100%, of the total stream (m).

The amount of liquid mixture passed as part streams (m1) and (m5) into the upper and/or the lower region of apparatus 3 can be chosen within wide limits, depending on the content of dimethyl carbonate, such that it comprises 0 to 90%, preferably 0 to 30%, of the total stream (m). The same applies to the amount of liquid mixture recycled as part stream (m6).

The gaseous stream (v) leaving apparatus 6 in general comprises carbon dioxide and small amounts of methanol, dimethyl carbonate, methyl nitrite and various low-boiling constituents. If appropriate, it can be subjected to a further working up operation with the aim of recovering the useful substances still contained therein.

The liquid stream (w) removed in the upper region of the apparatus 6 mentioned in continuous operation has a temperature of 10° to 80° C., preferably 20° to 70° C., and, in addition to methanol and small amounts of dimethyl carbonate and water, comprises above all low-boiling constituents such as, for example, formaldehyde dimethyl acetal and methyl formate. If appropriate, like the stream (z) brought from apparatus 7, it is subjected to a further, if appropriate joint working up operation (compare streams (z), (w), (w1) in FIG. 7) with the aim of recovering the useful substances still contained therein.

The stream (u) introduced into the upper region of the apparatus 6 mentioned and brought from apparatus arrangement 8 in general has a temperature of −15° to 30° C., preferably −10° to 15° C., and comprises 60 to 99 mol % of methanol, 0 to 10 mol % of dimethyl carbonate, 0 to 10 mol % of methyl nitrite and 0 to 5 mol % of water, and if appropriate small amounts of other low-boiling constituents in an order of magnitude of 0 to 10 mol %, preferably 70 to 98 mol % of methanol, 0 to 5 mol % of dimethyl carbonate, 1 to 7 mol % of methyl nitrite and 0 to 3 mol % of water and, if appropriate, small amounts of other low-boiling components in an order of magnitude of 0 to 6 mol %.

The stream (p) leaving the apparatus 6 mentioned as the bottom product essentially comprises the process waste water and small amounts of salts dissolved therein which originate from neutralization of the bottom stream (g) of apparatus 3.

The stream (h) leaving apparatus 2 as the bottom product is combined with the stream (m6) brought from apparatus 6 to give stream (h1) and passed into apparatus 4. The apparatus 4 mentioned is in general operated in a temperature range of 90° to 240° C., depending on the internal pressure chosen.

The liquid stream (l) fed into the apparatus 4 mentioned and brought from apparatus 7 has a temperature of 40° to 90° C., preferably 50° to 80° C., and comprises 70 to 95 mol % of methanol, 5 to 30% of dimethyl carbonate and small amounts of low-boiling components in an order of magnitude of in general less than 5 mol %.

The stream (i) leaving apparatus 4 as the bottom product in general has a temperature of 90° to 240° C., preferably 90° to 190° C., and in general comprises less than 0.1 mol % of methanol, preferably less than 0.05 mol % of methanol, more than 90 mol % of dimethyl carbonate, preferably more than 95 mol % of dimethyl carbonate, and if appropriate small amounts of high-boiling constituents, such as, for example, dimethyl oxalate and other components in an order of magnitude in total of less than 10 mol %, preferably less than 5 mol %.

The stream (k) leaving apparatus 4 as the top product in general has a temperature of 80° to 160° C., preferably 90° to 140° C., and in general comprises 55 to 97 mol % of methanol, 2 to 35 mol % of dimethyl carbonate, 0 to 15 mol % of water and, where appropriate, small amounts of low-boiling constituents.

The apparatus 7 mentioned (methanol distillation) is operated in a pressure range from 0.2 to 1.5 bar, preferably 0.4 to 1 bar. The operating temperature is in general in the range from 20° to 80° C., preferably 40° to 70° C., depending on the internal pressure chosen.

The gaseous stream (z) leaving apparatus 7 in general comprises methanol and relatively small amounts of carbon dioxide, dimethyl carbonate and various low-boiling constituents, such as, for example, methyl formate and formaldehyde dimethyl acetal.

The stream (n) leaving apparatus 7 as the bottom product is in the range from 20° to 80° C., preferably 40° to 70° C., in respect of its temperature and in general comprises more than 80 mol % of methanol, preferably more than 90 mol % of methanol, and small amounts of dimethyl carbonate and water. Where appropriate, the stream (n) mentioned is divided into two part streams (n1) and (n2), (n1) being about 0 to 30%, preferably 0 to 20%, of the total stream (n).

The stream (i) leaving apparatus 4 is brought to the temperature desired for charging apparatus 5 (dimethyl carbonate distillation) with the aid of a heat exchanger. The stream (i1) thus obtained has a temperature of 20° to 180° C., preferably 40° to 170° C. The apparatus 5 mentioned is in general operated in the pressure range from 0.75 to 1.25 bar, preferably under about 1 bar.

The dimethyl carbonate (o) distilled in apparatus 5 has a purity of 99.0 to 99.9%, depending on the reflux/withdrawal ratio and the number of theoretical distillation stages.

The bottom product obtained in apparatus 5 essentially comprises high-boiling constituents, which are discarded or fed to a further working up operation.

The fresh methanol (b) fed to the overall process in general at ambient temperature is divided into the liquid part streams (x1) and (x2), the proportion of part stream (x1) comprising 50 to 100% of the total stream (b). Part stream (x2) is introduced into the upper region of apparatus 8c (low-boiling constituents scrubber), which is operated in the temperature range of −15° to 30° C., preferably −10° to 15° C., and in the pressure range of 1 to 5 bar, preferably 1.5 to 4 bar.

The stream (x5) leaving the apparatus 8c mentioned in general has a temperature of −15° to 30° C., preferably −10° to 15° C., and comprises 0 to 15 mol % of carbon monoxide, 30 to 80 mol % of carbon dioxide, 0 to 20 mol % of methyl nitrite, 0 to 5 mol % of nitrogen, 0 to 12 mol % of methanol, 0 to 3 mol % of dimethyl carbonate, 5 to 45 mol of nitrogen monoxide, 0 to 0.5 mol % of water and less than 15 mol % of various, usually highly volatile secondary components, preferably 1 to 12 mol % of carbon monoxide, 35 to 70 mol % of carbon dioxide, 0 to 7 mol % of methyl nitrite, 0 to 5 mol % of nitrogen, 0 to 7 mol % of methanol, 0 to 1 mol % of dimethyl carbonate, 5 to 40 mol % of nitrogen monoxide, 0 to 0.5 mol % of water and less than 10 mol % of various, usually highly volatile secondary components.

The abovementioned part stream (x1) of the fresh methanol fed to the overall process is fed into the upper region of apparatus 8b (methyl nitrite after-reactor/ methanol waste gas scrubber), which is operated in the temperature range of $-10°$ to 60° C., preferably 0° to 40° C., and in the pressure range of 1 to 5 bar, preferably 1.5 to 4 bar.

In continuous operation, the part portion (c1) of the oxygen introduced into the overall process in general at ambient temperature via feed (c) is advantageously chosen such that the ratio of the amounts of substances between oxygen and the nitrogen monoxide contained in the gas stream (x5) fed in is 0.20 to 0.30, preferably 0.23 to 0.28.

The stream (b1) leaving apparatus 8b as the bottom product is in the range from 0° to 60° C., preferably 0° to 40° C., in respect of its temperature and in general comprises more than 70 mol % of methanol, preferably more than 80 mol % of methanol, and small amounts of dimethyl carbonate, water, methyl nitrite and various low-boiling constituents. Where appropriate, the stream (b1) mentioned is divided into two part streams (b2) and (b3), (b2) comprising about 70 to 100%, preferably 80 to 100%, of the total stream (b1).

The stream (t) leaving the apparatus 8b mentioned as gaseous top product is waste gas, which is fed to an additional after-treatment, where appropriate. It essentially comprises carbon dioxide and small amounts of carbon monoxide, methanol and, where appropriate, inert gases and gaseous low-boiling constituents.

The liquid stream (x9) removed laterally from apparatus 8b in general comprises more than 70 mol % of methanol, preferably more than 80% of methanol, and small amounts of dimethyl carbonate, water, methyl nitrite and various low-boiling constituents. It is fed to apparatus 8a.

The apparatus 8a mentioned (methyl nitrite desorber) is operated in a temperature range from 0° to 70° C., preferably 20° to 60° C., and in a pressure range from 1 to 5 bar, preferably 1.5 to 4 bar.

The stream (x6) leaving apparatus 8a as the bottom product is in the range from 0° to 70° C., preferably 20° to 60° C., in respect of its temperature and in general comprises more than 70 mol % of methanol, preferably more than 80 mol % of methanol, and small amounts of dimethyl carbonate, water, methyl nitrite and various low-boiling constituents. Where appropriate, stream (x6) is divided into two part streams (x7) and (x8), (x7) comprising about 70 to 100%, preferably 80 to 100%, of the total stream (x6).

Part stream (x8) is combined with the stream (n2) brought from apparatus 7 to give stream (x3) and is brought to the temperature desired for feeding into the upper region of apparatus 8b with the aid of a heat exchanger. The stream (x4) which results in this way is in the working range of apparatus 8b in respect of its temperature.

Part stream (x7) is combined with the stream (f7) brought from apparatus 2 to give stream (x10) and is likewise fed into apparatus 8b.

The top product of the pressure distillation can alternatively also be depleted, in accordance with variant (e2) with respect to the component methanol, which is the substantial part of the permeate, by pervaporation or steam permeation. While the retained material is recycled to the pressure distillation mentioned, the said permeate is recycled to the process. The pressure distillation and the pervaporation or vapour permeation therefore further fit into the overall process concept in a manner which is advantageous from energy aspects and therefore preserves resources if these operations are not optimized as isolated process steps, as described in the literature cited, but are employed, as corresponds to the process according to the invention, in combination with recycling steps for useful substances, such as, in particular, the methanol to be recycled.

Figure 5:
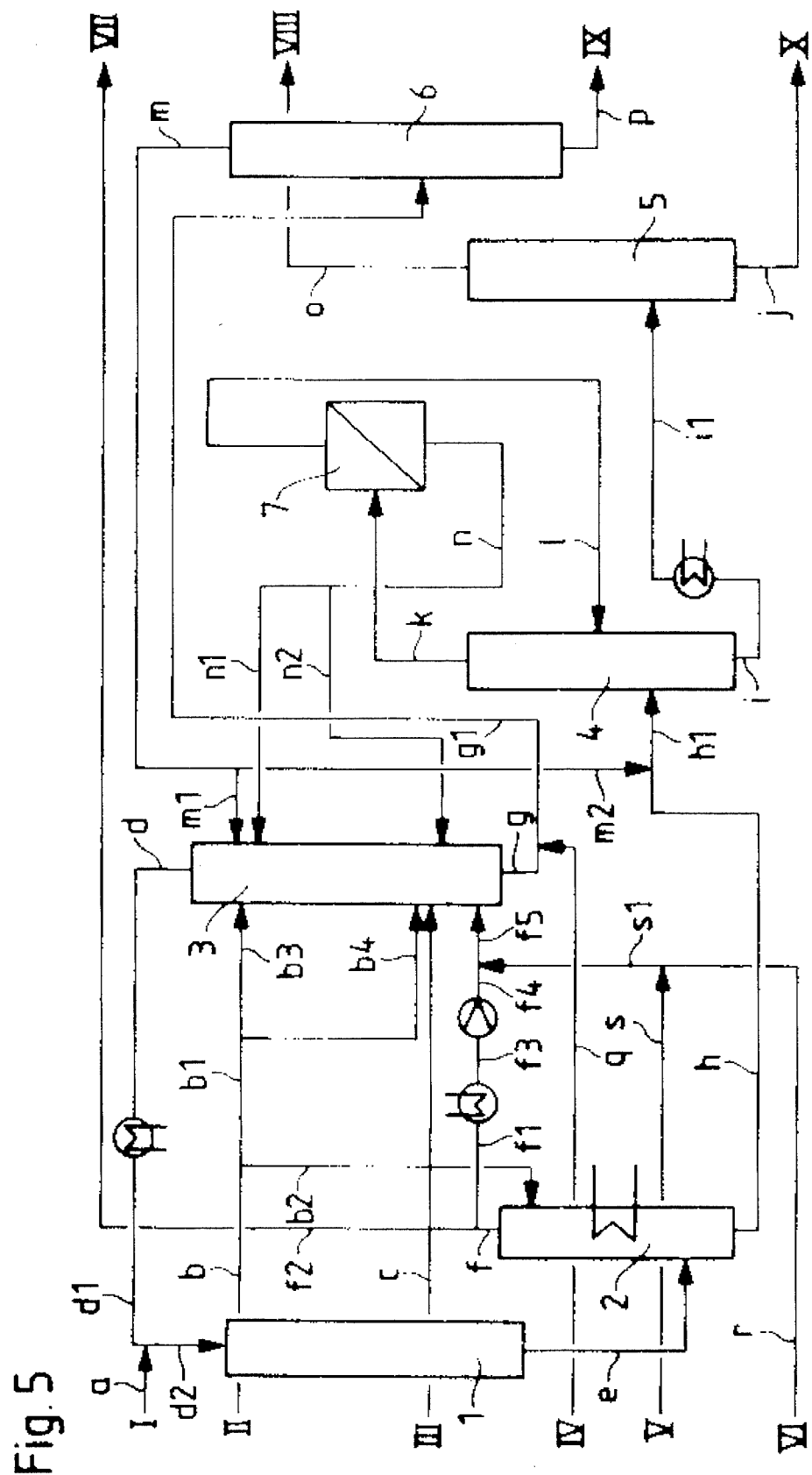

FIG. 5 shows merely one of the variants possible according to the invention of (e2), in which the oxygen (c), the methanol part streams (b4) and (n2) and the combined stream (f5) of recycling circulating gas, inert gas newly fed in and nitric oxide freshly fed in are fed in separately. However, the process according to the invention is in no way limited to this embodiment. If special feeding units, such as, in particular, two-component nozzles and/or static mixers, and combinations of such elements, are used in particular, it is advantageous to introduce streams (f5) and/or (b4) and/or (n2) and the oxygen stream (c) together into the lower part of apparatus 3.

Apparatus 3 in FIG. 5 can be operated as described for FIG. 3. In another preferred embodiment, one-component or two-component nozzles or combinations of static mixers and one- or two-component nozzles are used for mixing the liquid and gaseous components or streams (b4, c, f5, n2) to be fed into the lower end of the apparatus 3 mentioned.

The pressure under which the distillation process within apparatus 4 is carried out when the variant according to (e2) is used is chosen such that the temperature of the condensate or of the vapours obtained as stream (k) at the top of the apparatus corresponds to the preferred temperature for the subsequent separation which proceeds in apparatus 7 (pervaporation or vapour permeation). The top pressure accordingly is in general 1 to 5 bar. If the pervaporation technique is used, the vapour stream (k) is condensed, so that it runs boiling to the membrane. In this case also, the column pressure is regulated accordingly.

Apparatus 6 (waste water distillation, compare FIG. 5), as in FIG. 3, is a distillation column charged with the neutralized bottom discharge (g1) of apparatus 3 (methyl nitrite synthesis). The task of this column is to separate off and recycle the methanol contained in the stream (g1) mentioned in the form of top stream (m), which is recycled as part stream (m1) into apparatus 3 (methyl nitrite synthesis) and as part stream (m2), combined with the bottom stream (h) of apparatus 2 (dimethyl carbonate condenser) to give stream (h1), into apparatus 4 (pressure distillation). The actual waste water of the overall process (p) is obtained at the bottom of apparatus 6. A variant which deviates from FIG. 3 is shown here in respect of the use of the methanol part stream (m2).

Apparatus 7 (methanol removal by pervaporation, compare FIG. 5) is, for example, a pervaporation plant such as is described in the dissertation by M. Francke, 22.06.1990, Rheinisch-Westfälische Technical College Aachen, Federal Republic of Germany. If special plasma-polymerized membranes such as are marketed, for example, by GFT are used, methanol is removed from mixtures with dimethyl carbonate at very high selectivities and permeate flow rates. In addition to this highly efficient removal of methanol from the azeotrope-like mixtures with dimethyl carbonate, pervaporation on such plasmapolymerized membranes offers the additional advantage that even small amounts of water which may still be contained in stream (k) can be removed in an extremely effective manner at the same time as the methanol. In this respect, the membranes of the type mentioned are also far superior to conventional membranes, such as are described, for example, in EP 331 846, in U.S. Pat. No. 4,877,529 or in EP 423 949. The permeate obtained in the course of the pervaporation is recycled as stream (n) to apparatus 3 (methyl nitrite synthesis), if appropriate after being split into part streams (n1) and (n2). The retained material, which comprises concentrated dimethyl carbonate, is fed back as stream (l) into apparatus 4.

Pervaporation plants which are designed in a coil module, tubular module or plate module construction are in general suitable for apparatus 7.

In an alternative variant, a vapour permeation plant which offers savings in energy compared with pervaporation and the advantage of a simpler construction is used as apparatus 7. These advantages essentially result from the elimination of the heat exchanger between the module units required in pervaporation plants for application of the heat of evaporation to the permeating components (compare the dissertation by M. Francke, 22.06.1990, Rheinisch-Westfälische Technical College Aachen). Methanol is also removed from mixtures with dimethyl carbonate at very high selectivities and permeate flow rates using the special plasma-polymerized membranes mentioned, such as are marketed, for example, by GFT. In addition to this highly efficient removal of methanol from the azeotrope-like mixtures with dimethyl carbonate, vapour permeation on such plasma-polymerized membranes also offers the surprising additional advantage that even small amounts of water which may still be contained in stream (k) are removed in an extremely effective manner at the same time as the methanol. The permeate obtained in the course of the vapour permeation is recycled as stream (n) into apparatus 3 (methyl nitrite synthesis). The retained material, which comprises concentrated dimethyl carbonate, is fed back as stream (l) into apparatus 4.

Apparatus 7 (pervaporation or vapour permeation) is in general operated on the permeate side under a pressure of 0.5 to 500 mbar, preferably 1 to 100 mbar, at a temperature of −30° to +30° C., preferably −15° to +10° C. The condensed permeate (n) in continuous operation has a composition of about 80 to 97 mol % of methanol, 0.5 to 15% of dimethyl carbonate and 0 to 7 mol % of water, preferably 70 to 88 mol % of methanol, 2 to 30 mol % of dimethyl carbonate and 0 to 5 mol % of water.

A pressure of 0.5 to 10 bar and a temperature of 20° to 150° C. are established on the retained material side. At the retained material side always prevails a higher pressure than at the permeate side.

The amount of condensed permeate recycled as part stream (n1) can be adjusted, depending on the content of dimethyl carbonate, such that it comprises between 0 and 100% of the total stream (n). The amount of condensed permeate recycled as part stream (n2) can be adjusted, depending on the content of dimethyl carbonate, such that it is between 0 and 90% of the total stream (n).

The statements made above for FIG. 3 apply to the apparatuses and substance streams not mentioned in connection with FIG. 5.

Another arrangement for variant (e2) is described as follows, with the aid of FIG. 12:

Apparatuses 1 and 2 are the same in construction and operation to those in FIG. 3 and FIG. 5. (y) is the batchwise or continuous feeding in of small amounts of gaseous auxiliaries (for example halogen or hydrogen halide). A part stream comprising chiefly methanol from apparatus arrangement 8 (working up of waste gas/recycling of useful substances/removal of by-products from the circulation), that is to say from (b1), is fed via (b3) into the upper region of apparatus 2.

The gaseous stream (f) obtained at the top of apparatus 2, after diversion of the portion (f2) intended for removal from the circulation, can be passed on as circulating stream (f1), if appropriate, to a heat exchanger (contained in FIG. 12) which allows the desired entry temperature for the further reaction to be established. The stream (f3) thus heated passes through the compressor and is passed as stream (f4) into apparatus arrangement 8. Depending on the mode of operation of the entire plant, such a prior heat exchanger can also be dispensed with, if appropriate. From this apparatus arrangement 8, the construction and function of which have been explained, stream (f5) is removed, which comprises the fresh methanol fed to the process and dissolved methyl nitrite as essential constituents. The stream (f5) mentioned is combined with stream (s1) composed of subsequently added inert gas, preferably, and as shown in FIG. 12, carbon dioxide (s), and subsequently added fresh nitric oxide (nitrogen monoxide in FIG. 12) (r), before it flows as feed gas stream (f6) into the preparation of methyl nitrite. A liquid stream (f7) furthermore is removed at the top of the apparatus 2 mentioned and is passed into apparatus arrangement 8 (see the description above).

The portion of the circulating gas (f2) removed from the circulation if appropriate can also be subjected to treatment by other suitable subsequent operations, such as are described, for example, in DOS 3 834 065, instead of as in the embodiment described below, which comprises the use of apparatus arrangement 8 (compare above).

Within apparatus 3 (methyl nitrite synthesis, compare FIG. 12), the processes proceed in the same manner as described above in connection with FIG. 7.

The construction of apparatus 3 is that described in connection with FIG. 3 and FIG. 5.

The mode of operation and construction of apparatuses 4 and 5 correspond to the description in connection with FIG. 3 and FIG. 5.

Figure 12:
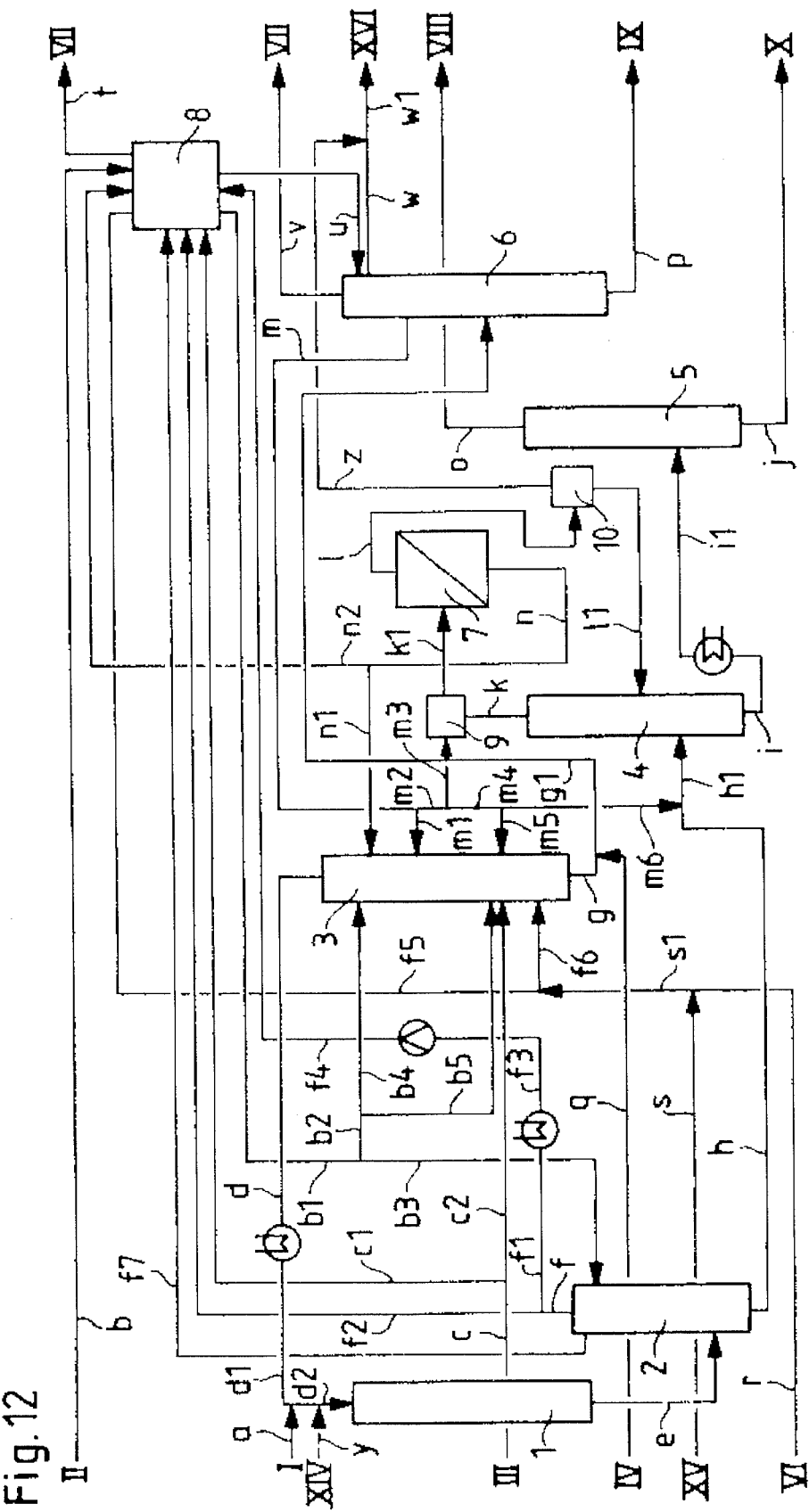

Apparatus 7 (methanol removal by pervaporation or vapour permeation, compare FIG. 12) is a pervaporation or a vapour permeation plant which serves to split the stream (k) obtained as the top product of distillation column 4 into retained material comprising methanol and dimethyl carbonate, which is removed (l) on the so-called retained material side of the apparatus and recycled, totally or partially as stream (l1) via apparatus 10, back into distillation column 4, and a permeate (n) which essentially comprises methanol, is removed on the so-called permeate side and is passed on as part stream (n1) into the upper part of the methyl nitrite reactor (apparatus 3) and as part stream (n2) into apparatus arrangement 8 (working up of waste gas/ recycling of useful substances/removal of by-products from the circulation). The apparatus 7 mentioned is additionally fed on the retained material side by the part stream (m3) comprising the methanol originating from the waste water distillation, and in particular preferably in a form such that streams (k) and (m3) are combined beforehand in a storage vessel apparatus 9, from which stream (k1) is removed for charging apparatus 7.

Apparatus 7 (case: methanol removal by pervaporation) is, for example, an apparatus of the type described above.

The apparatus 9 already mentioned above is a pressure-resistant stirred storage tank intended for collection of streams (m3) and (k). The apparatus 10 mentioned above is likewise a pressure-resistant stirred storage tank. According to the mode of operation, depending on problems due to varying qualities of the feed substances or for other reasons, it may be appropriate to remove from the apparatus 10 mentioned an additional gaseous stream (z) by depressurisation which is particularly rich in low-boiling by-products and which can be fed, if appropriate, to a further working up operation, for example a removal of by-products (not the subject-matter of the process circuit described in FIG. 12), the useful substances recovered during this working up operation being fed into the process again, where appropriate, at another suitable point (compare also the description of apparatus 6, stream (w) there).

The above descriptions of FIG. 8 and FIG. 9 and the apparatuses described therein also apply in connection with FIG. 12.

The substance streams described in FIGS. 12, 8 and 9 and the associated pressure and temperature conditions such as are realized in carrying out the process according to the invention are described in the following.

The gas stream (d2) passed into apparatus i in continuous operation in general has a temperature of 25° to 120° C., preferably 50° to 110° C., and a pressure of 1 to 5 bar, preferably 1.5 to 4 bar. In general, it comprises 4 to 25 mol % of carbon monoxide, 30 to 80 mol % of carbon dioxide, 5 to 40 mol % of methyl nitrite, 0 to 5 mol % of nitrogen, 1 to 10 mol % of methanol, 0 to 5 mol % of dimethyl carbonate, 0.1 to 5.0 mol % of nitrogen monoxide, 0 to 1 mol % of water and less than 15 mol % of various, usually highly volatile secondary components, preferably 5 to 20 mol % of carbon monoxide, 35 to 70 mol % of carbon dioxide, 10 to 35 mol % of methyl nitrite, 0 to 4 mol % of nitrogen, 2 to 9 mol % of methanol, 0 to 4 mol % of dimethyl carbonate, 0.5 to 5.0 mol % of nitrogen monoxide, 0 to 0.5 mol % of water and 1 to 12 mol % of various, usually highly volatile secondary components.

The stream (y) admixed to the stream (d2), where appropriate, before entry into apparatus 1 comprises, as the activator, hydrogen halide and/or methyl chloroformiate and/or halogen and/or other substances which contain halogen acting activating under the reaction conditions, preferably hydrogen chloride and/or chlorine, in pure or dilute form and is metered in such that the gas stream entering apparatus 1 comprises 0 to 3000 ppm, preferably 10 to 1000 ppm, of these components.

The gas stream (e) leaving apparatus 1 in continuous operation in general has a temperature of 50° to 170° C., preferably 60° to 160° C., and a pressure of 1 to 5 bar, preferably 1.5 to 4 bar. In general, it comprises 0 to 12 mol % of carbon monoxide, 30 to 80 mol % of carbon dioxide, 0 to 20 mol % of methyl nitrite, 0 to 5 mol % of nitrogen, 2 to 12 mol % of methanol, 3 to 25 mol % of dimethyl carbonate, 5 to 40 mol % of nitrogen monoxide, 0 to 0.5 mol % of water and less than 16 mol % of various, usually highly volatile secondary components, preferably 1 to 10 mol % of carbon monoxide, 35 to 70 mol % of carbon dioxide, 1 to 19 mol % of methyl nitrite, 0 to 5 mol % of nitrogen, 3 to 10 mol % of methanol, 5 to 20 mol % of dimethyl carbonate, 5 to 35 mol % of nitrogen monoxide, 0 to 0.5 mol % of water and less than 13 mol % of various, usually highly volatile secondary components.

The gas stream (f) leaving apparatus 2 in continuous operation in general has a temperature of 0° to 50° C., preferably 5° to 40° C., and a pressure of 1 to 5 bar, preferably 1.5 to 4 bar. In general, it comprises 0 to 15 mol % of carbon monoxide, 30 to 80 mol % of carbon dioxide, 0 to 20 mol % of methyl nitrite, 0 to 5 mol % of nitrogen, 0 to 12 mol % of methanol, 0 to 5 mol % of dimethyl carbonate, 5 to 45 mol % of nitrogen monoxide, 0 to 1 mol % of water and less than 20 mol % of various, usually highly volatile secondary components, preferably 1 to 12 mol % of carbon monoxide, 35 to 70 mol % of carbon dioxide, 3 to 15 mol % of methyl nitrite, 0 to 5 mol % of nitrogen, 3 to 10 mol % of methanol, 0 to 3 mol % of dimethyl carbonate, 5 to 40 mol % of nitrogen monoxide, 0 to 0.5 mol % of water and less than 14 mol % of various, usually highly volatile secondary components.

The amount of the portion of circulating gas removed from the circulation as gas stream (f2) in continuous operation is in general 0 to 7% by weight, preferably 0.1 to 5% by weight, based on the gaseous top stream (f) of apparatus 2.

The liquid stream (f7) removed in the upper region of apparatus 2 comprises 20 to 90% by weight of methanol, 10 to 80% by weight of dimethyl carbonate and less than 30% by weight of other, usually less volatile, dissolved components, preferably 25 to 60% by weight of methanol, 40 to 75% by weight of dimethyl carbonate and less than 20% by weight of other, usually less volatile dissolved components.

The gaseous main stream (f1) which reins after the gas stream (f2) has been removed from the circulation is fed, after passing through a heat exchanger as stream (f3) and subsequently a compressor as stream (f4) to apparatus arrangement 8. The stream (f4) mentioned then has a temperature of 10° to 70° C., preferably 20° to 60° C., and a pressure of 1 to 5 bar, preferably 1.5 to 4 bar.

The stream (f5) recycled from apparatus arrangement 8 in general has a temperature of 0° to 70° C., preferably 20° to 60° C., and a pressure of 1 to 5 bar, preferably 1.5 to 4 bar. In general, it comprises 0 to 15 mol % of carbon monoxide, 30 to 80 mol % of carbon dioxide, 0 to 20 mol % of methyl nitrite, 0 to 5 mol % of nitrogen, 0 to 16 mol % of methanol, 0 to 5 mol % of dimethyl carbonate, 5 to 45 mol % of nitrogen monoxide, 0 to 1 mol % of water and less than 20 mol % of various, usually highly volatile secondary components, preferably 1 to 12 mol % of carbon monoxide, 35 to 70 mol % of carbon dioxide, 3 to 15 mol % of methyl nitrite, 0 to 5 mol % of nitrogen, 3 to 10 mol % of methanol, 0 to 3 mol % of dimethyl carbonate, 5 to 40 mol % of nitrogen monoxide, 0 to 0.5 mol % of water and less than 14 mol % of various, usually highly volatile secondary components.

The stream (h) leaving apparatus 2 as the bottom product in general has a temperature of 10° to 150° C., preferably 20° to 140° C., and in general comprises 0 to 40 mol % of methanol, 20 to 99 mol % of dimethyl carbonate and, where appropriate, small amounts of water, high-boiling constituents, such as, for example, dimethyl oxalate, and other components in an order of magnitude of less than 5 mol %.

The feed rate of the gaseous nitrogen monoxide, which is in general introduced as stream (r) at ambient temperature, into apparatus 3 (compare FIG. 12) in continuous operation is 0 to 3 mol %, preferably 0 to 1.5 mol %, based on the gas stream (f5). Instead of the nitrogen monoxide, it is in principle also possible for equivalent amounts of nitrogen dioxide, dinitrogen trioxide, dinitrogen tetroxide, methyl nitrite or any desired mixtures of these substances to be fed in.

The feed rate of the gaseous carbon dioxide in general introduced as stream (s) at ambient temperature into apparatus 3 (compare FIG. 12) in continuous operation is 0 to 3 mol %, preferably 0 to 1.5 mol %, based on gas stream (f5).

The gas stream (f6) which results from joining streams (s1) and (f5) in continuous operation in general has a temperature of 0° to 70° C., preferably 20° to 60° C., and a pressure of 1 to 5 bar, preferably 1.5 to 4 bar.

The stream (b2) brought from apparatus arrangement 8 is in general chosen such that the ratio of the amounts of substances between the methanol contained therein and the nitrogen monoxide contained in the gas stream (f6) is 1 to 10, preferably 1 to 5. The stream (b2) mentioned is separated into part streams (b4) and (b5), if appropriate, part stream (b4) in general comprising 50 to 100%, preferably 70 to 100%, of stream (b2).

In a specific embodiment of the process according to the invention, the amount of methanol fed in via feed (b5) in continuous operation is advantageously chosen such that the ratio of the amounts of substances between this methanol and the nitrogen monoxide contained in the gas stream (f6) fed in is 0.1 to 2.5, preferably 0.1 to 1.5.

In continuous operation, the amount of oxygen in general introduced at ambient temperature via feed (c2) is advantageously chosen such that the ratio of the amounts of substances between oxygen and the nitrogen monoxide contained in the gas stream (f6) fed in is 0.15 to 0.26, preferably 0.20 to 0.25.

The internal pressure of the apparatus 3 mentioned is in general 1 to 5 bar, preferably 1.5 to 4 bar, and its internal temperature can be varied within wide limits. The temperature profile over the entire length of the apparatus is established as a function of the amount, entry temperature and state of aggregation of the individual feeds, the overall pressure, the conversion of the reactants introduced, the reflux of the top condenser and the energy supplied to the bottom of the apparatus.

The liquid stream (g) which leaves apparatus 3 as the bottom product in continuous operation in general has a temperature of 10° to 150° C., preferably 20° to 140° C., and in general comprises 0 to 70 mol % of methanol, 10 to 99 mol % of water, 0 to 20 mol % of dimethyl carbonate and, where appropriate, small amounts of nitric acid and other dissolved components.

The stream (q) which is in general introduced at ambient temperature and comprises a base for the purpose of neutralization is in general chosen such that it is capable of neutralizing the acid contained in the stream (g) mentioned.

The stream (d) leaving apparatus 3 as the top product in continuous operation in general has a temperature of 0° to 60° C., preferably 10° to 50° C., and a pressure of 1 to 5 bar, preferably 1.5 to 4 bar, and in general comprises 0 to 20 mol % of carbon monoxide, 30 to 80 mol % of carbon dioxide, 5 to 40 mol % of methyl nitrite, 0 to 5 mol % of nitrogen, 1 to 12 mol % of methanol, 0 to 5 mol % of dimethyl carbonate, 0.1 to 5 mol % of nitrogen monoxide, 0 to 1 mol % of water and less than 15 mol % of various, usually highly volatile secondary components, preferably 5 to 15 mol % of carbon monoxide, 35 to 70 mol % of carbon dioxide, 10 to 35 mol % of methyl nitrite, 0 to 4 mol % of nitrogen, 2 to 9 mol % of methanol, 0 to 4 mol % of dimethyl carbonate, 0.5 to 5 mol % of nitrogen monoxide, 0 to 0.5 mol % of water and 1 to 12 mol % of various, usually highly volatile secondary components.

If appropriate, the stream (d) mentioned is brought to the temperature desired for feeding it into apparatus 1 with the aid of a heat exchanger. The carbon monoxide in general fed as stream (a) at ambient temperature to the stream (d1) obtained in this manner is in general employed in chemically pure form, but may comprise foreign gases, such as, for example, small amounts of hydrogen (<0.1 mol %) or methane (<0.1 mol %), depending on the method of preparation. In continuous operation, it is fed in such that the ratio of the amounts of substances between the carbon monoxide metered in and the dimethyl carbonate produced is 1 to 1.2 and a concentration of the carbon monoxide in gas stream (d2) which is constant with respect to time exists.

Apparatus 6 (waste water distillation) is in general operated under a pressure of 0.5 to 2 bar, preferably 0.5 to 1.5 bar. The liquid stream (m) removed in the upper region of this apparatus is obtained in continuous operation with a temperature of 25° to 80° C., preferably 40° to 75° C., and in general comprises 60 to 95 mol % of methanol, 1 to 35 mol % of dimethyl carbonate and 0 to 7 mol % of water, preferably 70 to 95 mol % of methanol, 2 to 30 mol % of dimethyl carbonate and 0 to 5 mol % of water.

The amount of liquid mixture recycled as part stream (m3) of the stream (m) mentioned can be chosen within wide limits, depending on the content of dimethyl carbonate, such that it comprises 0 to 100%, preferably 30 to 100%, of the total stream (m).

The amount of liquid mixture passed as part streams (m1) and (m5) into the upper and/or the lower region of apparatus 3 can be chosen within wide limits, depending on the content of dimethyl carbonate, such that it comprises 0 to 90%, preferably 0 to 30%, of the total stream (m). The same applies to the amount of liquid mixture recycled as part stream (m6).

The gaseous stream (v) leaving apparatus 6 in general comprises carbon dioxide and small amounts of methanol, dimethyl carbonate, methyl nitrite and various low-boiling constituents. If appropriate, it can be subjected to a further working up operation with the aim of recovering the useful substances still contained therein.

The liquid stream (w) removed in the upper region of the apparatus 6 mentioned in continuous operation has a temperature of 10° to 80° C., preferably 20° to 70° C., and, in addition to methanol and small amounts of dimethyl carbonate and water, comprises above all low-boiling constituents such as, for example, formaldehyde dimethyl acetal and methyl formate. Where appropriate, like the stream (z) brought from the storage vessel apparatus 10, it is subjected to further a working up operation with the aim of recovering the useful substances still contained therein, which can then be recycled again into the process at another suitable point.

The stream (u) introduced into the upper region of the apparatus 6 mentioned and brought from apparatus arrangement 8 in general has a temperature of −15° to 30° C., preferably −10° to 15° C., and comprises 60 to 99 mol % of methanol, 0 to 10 mol % of dimethyl carbonate, 0 to 10 mol % of methyl nitrite and 0 to 5 mol % of water, and if appropriate small amounts of other low-boiling components in an order of magnitude of 0 to 10 mol %, preferably 70 to 98 mol % of methanol, 0 to 5 mol % of dimethyl carbonate, 1 to 7 mol % of methyl nitrite and 0 to 3 mol % of water and, if appropriate, small amounts of other low-boiling components in an order of magnitude of 0 to 6 mol %.

The stream (p) leaving apparatus 6 as the bottom product essentially comprises the process waste water and small amounts of salts dissolved therein which originate from neutralization of the bottom stream (g) of apparatus 3.

The stream (h) leaving apparatus 2 as the bottom product is combined with the stream (m6) brought from apparatus 6 to give stream (h1) and passed into apparatus 4. The apparatus 4 mentioned is in general operated in a temperature range of 90° to 240° C., depending on the internal pressure chosen.

The liquid stream (l1) fed into apparatus 4 and brought from apparatus 10 has a temperature of 40° to 100° C., preferably 50° to 80° C., and comprises 15 to 45 mol % of methanol, 40 to 75% of dimethyl carbonate and small amounts of low-boiling components in an order of magnitude of in general less than 10 mol %.

The stream (i) leaving apparatus 4 as the bottom product in general has a temperature of 90° to 240° C., preferably 90° to 140° C., and in general comprises less than 0.1 mol % of methanol, preferably less than 0.05 mol % of methanol, more than 90 mol % of dimethyl carbonate, preferably more than 95 mol % of dimethyl carbonate, and if appropriate small amounts of high-boiling constituents, such as, for example, dimethyl oxalate and other components in an order of magnitude in total of less than 10 mol %, preferably less than 5 mol %.

If the vapour permeation technique is used, the distillation in apparatus 4 (pressure distillation) is preferably carried out under a pressure such that the vapours obtained as stream (k) have the optimum temperature for their further separation. The pressures are then in general 1 to 4 bar. If the pervaporation technique is used, vapour stream (k) is condensed and fed to the membrane at optimal temperature. In this case also, the column pressure is regulated accordingly.

The stream (k) leaving apparatus 4 is passed into the storage tank apparatus 9. In general, it comprises 55 to 97 mol % of methanol, 2 to 35 mol % of dimethyl carbonate, 0 to 15 mol % of water and, where appropriate, small amounts of low-boiling constituents.

Streams (m3) and (k) are preferably collected in the apparatus 9 mentioned. The contents of this apparatus are stirred, if appropriate, and kept, if appropriate by means of external regulation, in a temperature range of 20° to 150° C., preferably 50° to 90° C., and a pressure range of 1 to 5 bar, preferably 1.5 to 4 bar.

The gaseous stream (z) leaving apparatus 10 in general comprises methanol and small amounts of carbon dioxide, dimethyl carbonate and various low-boiling constituents, such as, for example, methyl formate and formaldehyde dimethyl acetal. If appropriate, like the stream (w) removed from apparatus 6, it is subjected to further a working up operation with the aim of recovering the useful substances still contained therein, which can then be recycled into the process again at another suitable point.

The apparatus 7 mentioned (pervaporation or vapour permeation) is operated in a pressure range of 0.5 to 10 bar, preferably 1 to 5 bar, on the retained material side and 0.5 to 500 mbar, preferably 1 to 100 mbar, on the permeate side. The operating temperature is 20° to 150° C., preferably 50° to 90° C., on the retained material side and −30° to +30° C., preferably −15° to +10° C., on the permeate side.

The stream (n) leaving apparatus 7 as the permeate is in the range from −30° to +30° C., preferably −15° to +10° C., in respect of its temperature and in general comprises more than 70 mol % of methanol, preferably more than 90 mol % of methanol, and small amounts of dimethyl carbonate and water. If appropriate, the stream (n) mentioned is divided into two part streams (n1) and (n2), (n1) being about 0 to 30%, preferably 0 to 20%, of the total stream (n).

The stream (i) leaving apparatus 4 is brought to the temperature desired for charging apparatus 5 (dimethyl carbonate distillation) with the aid of a heat exchanger. The stream (i1) thus obtained has a temperature of 20° to 180° C., preferably 40° to 170° C. The apparatus 5 mentioned is in general operated in the pressure range of 0.75 to 1.25 bar, preferably under about 1 bar.

The dimethyl carbonate (o) distilled in apparatus 5 has a purity of 99.0 to 99.9%, depending on the reflux/withdrawal ratio.

The bottom product obtained in apparatus 5 essentially comprises high-boiling constituents, which are discarded or fed to a further working up operation.

The fresh methanol (b) fed to the overall process in general at ambient temperature is divided into the liquid part streams (x1) and (x2), the proportion of part stream (x1) comprising 50 to 100% of the total stream (b). Part stream (x2) is introduced into the upper region of apparatus 8c (low-boiling constituents scrubber), which is operated in the temperature range of −15° to 30° C., preferably −10° to 15° C., and in the pressure range of 1 to 5 bar, preferably 1.5 to 4 bar.

The stream (x5) leaving the apparatus 8c mentioned in general has a temperature of −15° to 30° C., preferably −10° to 15° C., and comprises 0 to 15 mol % of carbon monoxide, 30 to 80 mol % of carbon dioxide, 0 to 20 mol % of methyl nitrite, 0 to 5 mol % of nitrogen, 0 to 12 mol % of methanol, 0 to 3 mol % of dimethyl carbonate, 5 to 45 mol % of nitrogen monoxide, 0 to 0.5 mol % of water and less than 15 mol % of various, usually highly volatile secondary components, preferably 1 to 12 mol % of carbon monoxide, 35 to 70 mol % of carbon dioxide, 0 to 7 mol % of methyl nitrite, 0 to 5 mol % of nitrogen, 0 to 7 mol % of methanol, 0 to 1 mol % of dimethyl carbonate, 5 to 40 mol % of nitrogen monoxide, 0 to 0.5 mol % of water and less than 10 mol % of various, usually highly volatile secondary components.

The abovementioned part stream (x1) of the fresh methanol fed to the overall process is fed into the upper region of apparatus 8b (methyl nitrite after-reactor/methanol waste gas scrubber), which is operated in the temperature range of −10° to 60° C., preferably 0° to 40° C., and in the pressure range of 1 to 5 bar, preferably 1.5 to 4 bar.

In continuous operation, the portion (c1) of the oxygen introduced into the overall process in general at ambient temperature via feed (c) is advantageously chosen such that the ratio of the amounts of substances between oxygen and the nitrogen monoxide contained in the gas stream (x5) fed in is 0.20 to 0.30, preferably 0.23 to 0.28.

The stream (b1) leaving the apparatus 8b mentioned as the bottom product is in the range from 0° to 60° C., preferably 0° to 40° C., in respect of its temperature and in general comprises more than 70 mol % of methanol, preferably more than 80 mol % of methanol, and small amounts of dimethyl carbonate, water, methyl nitrite and various low-boiling constituents. Where appropriate, the stream (b1) mentioned is divided into two part streams (b2) and (b3), (b2) comprising about 70 to 100%, preferably 80 to 100%, of the total stream (b1).

The stream (t) leaving apparatus 8b as gaseous top product is waste gas, which is fed to an additional after-treatment, where appropriate. It essentially comprises carbon dioxide and small amounts of carbon monoxide, methanol and, where appropriate, inert gases and gaseous low-boiling constituents.

The liquid stream (x9) removed laterally from apparatus 8b in general comprises more than 70 mol % of methanol, preferably more than 80% of methanol, and small amounts of dimethyl carbonate, water, methyl nitrite and various low-boiling constituents. It is fed to apparatus 8a.

Apparatus 8a (methyl nitrite desorber) is operated in a temperature range from 0° to 70° C., preferably 20° to 60° C., and in a pressure range from 1 to 5 bar, preferably 1.5 to 4 bar.

The stream (x6) leaving apparatus 8a as the bottom product is in the range from 0° to 70° C., preferably 20° to 60° C., in respect of its temperature and in general Comprises more than 70 mol % of methanol, preferably more than 80 mol % of methanol, and small amounts of dimethyl carbonate, water, methyl nitrite and various low-boiling constituents. Where appropriate, stream (x6) is divided into two part streams (x7) and (x8), (x7) comprising about 70 to 100%, preferably 80 to 100%, of the total stream (x6).

Part stream (x8) is combined with the stream (n2) brought from apparatus 7 to give stream (x3) and is brought to the temperature desired for feeding into the upper region of the apparatus 8b mentioned with the aid of a heat exchanger. The stream (x4) which results in this way is in the working range of apparatus 8b in respect of its temperature.

Part stream (x7) is combined with the stream (f7) brought from apparatus 2 to give stream (x10) and is likewise fed into apparatus 8b.

EXAMPLE 1

Preparation of the Catalyst 0.835 g of $PdCl_2$ was dissolved in 4 ml of water, with addition of 2 g of sodium chloride. 25 ml of a 25% strength ammonia solution were added at room temperature, while stirring. 100 ml of active charcoal Norit ROX 0.8 were impregnated with this solution and then dried in a stream of nitrogen.

Preparation of Dimethyl Carbonate 960 ml of the above catalyst were introduced into a tube-bundle reactor about 900 mm long made of material 1.4571 and comprising 4 reaction tubes (dimensions of the tubes: 25.0×800 mm, wall thickness 2.0 mm), the catalyst filling height being about 700 mm.

Figure 4:
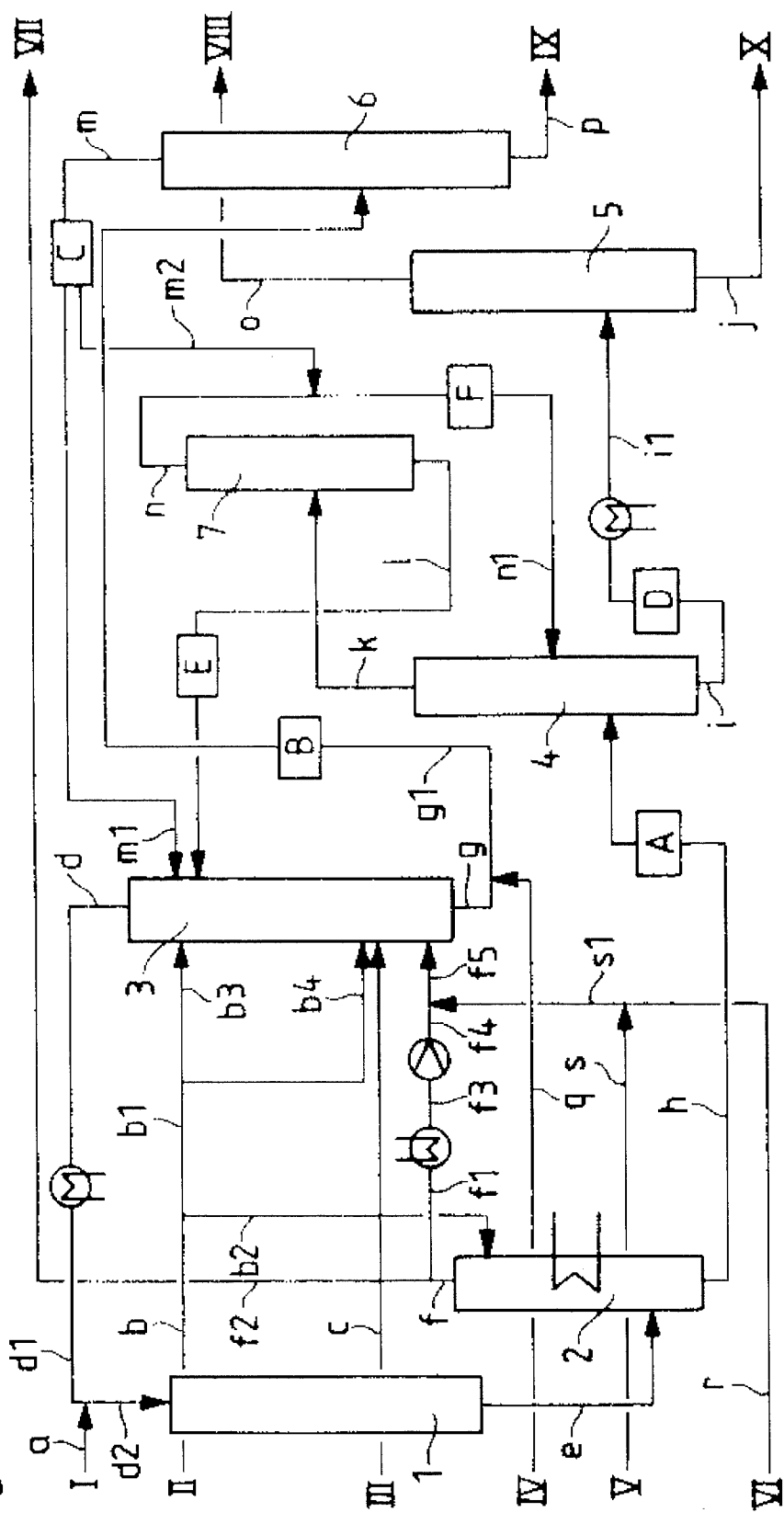

On average, 4927 g/hour of a mixture, heated to about 80° C. by means of a prior tube-bundle heat exchanger, which comprised 13.2 mol % of carbon monoxide, 2.2 mol % of carbon dioxide, 15.1 mol % of methyl nitrite, 60.2 mol % of nitrogen, 5.1 mol % of methanol, 0.7 mol % of dimethyl carbonate, 3.3 mol % of nitrogen monoxide and 0.2 mol % of water (compare stream (d2) in FIG. 4) were allowed to flow in under 3130 mbar. In continuous operation, this gas mixture was composed of the gas flowing out at the top of the methyl nitrite reactor (compare stream (d) in FIG. 4) and about 128 g/hour of carbon monoxide freshly metered in (compare stream (a) in FIG. 4). The cooling (water) applied to the reactor was automatically regulated such that the gas stream leaving the reactor (compare stream (e) in FIG. 4) had a temperature of about 120° C. This gas stream was passed into the side of a scrubber/condenser (dimensions: 600×48.3 mm, wall thickness 2.6 mm) filled with glass Raschig rings (4×4 mm), in which partial condensation took place. At the top of this apparatus was attached a tube-bundle heat exchanger condensing on the jacket side, which comprised 7 tubes of dimensions 2000×10 mm (wall thickness 1 mm) and was regulated by cooling with cold water (temperature <10° C.) such that the gas emerging downstream of this condenser (compare stream (f) in FIG. 4) had a temperature of about 15° C. Under a pressure of 3020 mbar, which was thereby established, this gas comprised on average 10.7 mol % of carbon monoxide, 2.4 mol % of carbon dioxide, 9.6 mol % of methyl nitrite, 63.9 mol % of nitrogen, 2.6 mol % of methanol, 0.8 mol % of dimethyl carbonate and 10 mol % of nitrogen monoxide. The bottom stream (compare stream (h) in FIG. 4), of on average 527 g/hour, was discharged at a temperature of about 47° C., comprised 46.3 mol % of methanol, 49.1 mol % of dimethyl carbonate, 2.2 mol % of dimethyl oxalate and 2.2 mol % of water and was passed into buffer vessel A (compare FIG. 4).

About 0.2% by weight of the gas stream obtained at the top of the scrubber/condenser was removed continuously from the circulation in order to prevent concentration of gaseous by-products within the circulatory process (compare stream (f2) in FIG. 4). The gas which remained was brought to a pressure of about 3250 mbar and a temperature of about 28° C. via a heat exchanger and a piston compressor, combined with on average an additional 2.4 g/hour of nitrogen monoxide and 4.9 g/hour of nitrogen and fed with about 56 g/hour of fresh methanol and about 71 g/hour of oxygen into the lower part of the methyl nitrite reactor (compare apparatus 3 in FIG. 4) such that mixing of all the reactants was as sudden and complete as possible, without safety-critical concentration ranges of flammable mixtures being thereby entered.

This was effected such that the circulating gas was mixed with the freshly metered-in gases nitrogen monoxide (compare stream (r) in FIG. 4) and nitrogen (compare stream (s) in FIG. 4) within a first static mixer element, the methanol was sprayed in directly afterwards via a one-component nozzle and, immediately after the addition of methanol and still before the subsequent static mixer element in which all the reaction components then present are mixed intensively, oxygen was fed in.

On average, 226 g/hour of fresh methanol (compare stream (b3) in FIG. 4), 80 g/hour of the recycled methanol (compare stream (m1) in FIG. 4), which was removed from buffer vessel C (compare FIG. 4), and 155 g/hour of the mixture essentially comprising methanol (compare stream (l) in FIG. 4), which was removed from buffer vessel E (compare FIG. 4), were thereby pumped into the upper part of the reactor. The methyl nitrite reactor (dimensions: 2200× 48.3 mm, wall thickness 2.6 mm) was a reaction vessel which contained packing (glass rings of dimensions 4×4 mm) and had an internal free volume of about 2.25 l.

At the top of this apparatus was attached a tube-bundle heat exchanger condensing on the jacket side, which comprised 7 tubes of dimensions 10×1000 mm (wall thickness 1 mm) and the cooling capacity of which, by cooling with cold water (temperature <15° C.) was regulated such that the gas emerging downstream of this condenser (compare stream (d) in FIG. 4) had a temperature of about 28° C. It was on average under a pressure of about 3140 mbar and was recycled continuously into the dimethyl carbonate reactor (see above).

The liquid bottom stream (compare stream (g) in FIG. 4) of on average 219 g/hour was discharged at a temperature of about 28° C., contained 38.9 mol % of methanol, 5.1 mol % of dimethyl carbonate and 55.6 mol % of water and, after neutralization of the small amounts of nitric acid contained therein, was passed into buffer vessel B (compare FIG. 4).

The hot mixture at about 45° C. contained in buffer vessel A (compare FIG. 4) was fed into the side of a continuously operating pressure column (apparatus 4 in FIG. 4) which was operated in a pressure range of 9085 (bottom) to 9050 mbar (top). This pressure column was a distillation column (dimensions 33.7×2500 mm, wall thickness 2.6 mm) filled with packing (glass rings of dimensions 4×4 mm), in which about 15 theoretical separation stages were realized and which operated at a reflux ratio of 1.1:1. This pressure column furthermore was also charged from buffer vessel F (compare FIG. 4) with return stream (n1) (compare FIG. 4) (see below). A column unit with jacket heating formed the lower end of this pressure column. At the upper end of the pressure column was a horizontal double-tube condenser operated with cooling water.

The liquid mixture discharged at the bottom (compare stream (i) in FIG. 4) of on average 398 g/hour had a temperature of on average about 180° C. and was transferred to buffer vessel D (compare FIG. 4). The condensate obtained at the top (compare stream (k) in FIG. 4) of on average 744 g/hour had a temperature of about 125° C. and comprised on average about 86 mol % of methanol, about 11 mol % of dimethyl carbonate, about 1 to 1.5 mol of water and small amounts of low-boiling constituents. It was fed into the side of a continuously operating distillation column operated under normal pressure (compare apparatus 7 in FIG. 4), in which separation into a bottom discharge, which comprised chiefly methanol and water and which was transferred to buffer vessel E, and into a top product (compare stream (n) in FIG. 4) of on average 589 g/hour, which comprised about 83 mol % of methanol, about 14 mol % of dimethyl carbonate and small amounts of low-boiling constituents and which was passed as condensate at a temperature of about 60° C. into buffer vessel F (compare FIG. 4) took place. On average 28 g/hour of the mixture from buffer vessel C (compare FIG. 4), which originated from the waste water distillation (compare apparatus 6 in FIG. 4) furthermore were passed into this buffer vessel E, the contents of which were stirred magnetically. On average 615 g/hour of the mixture from buffer vessel F (compare FIG. 4) were pumped into the side of the pressure distillation (compare apparatus 4 in FIG. 4), that is to say thus represented the second feed stream from which the distillated separation proceeding in this apparatus was fed. This column was a distillation column (dimensions 42.4×3200 mm, wall thickness 2.0 mm) filled with packing (glass rings of dimensions 4×4 mm), in which about 25 theoretical separation stages were realized and which operated at a reflux ratio of 1.7:1. A column unit with jacket heating formed the lower end of the column mentioned. At the upper end of the said column was a horizontal double-tube condenser operated with cooling water.

The substance mixture in buffer vessel D (compare FIG. 4), after being cooled to about 95° C. by means of an interpolated simple tube-bundle heat exchanger, the cooling capacity of which was regulated automatically such that the emerging liquid had the desired temperature, was fed into the side of a continuously operating column operated under normal pressure (compare stream (i1) in FIG. 4). This column was a distillation column (dimensions 33.7×2200 mm, wall thickness 2.6 mm) filled with packing (glass rings of dimensions 4×4 mm), in which about 15 theoretical separation stages were realized and which operated at a reflux ratio of 1:1. A column unit with jacket heating formed the lower end of the column mentioned. At the upper end of this column was a horizontal double-tube condenser operated with cooling water.

On average, 375 g/hour of dimethyl carbonate with a purity of >99.7% (gas chromatography) were obtained as the top product of the distillation (compare stream (o) in FIG. 4). The bottom discharge of on average 23 g/hour contained high-boiling constituents, essentially, to the extent of more than 90%, dimethyl oxalate.

The neutralized bottom discharge of the methyl nitrite reactor (compare apparatus 3 in FIG. 4) in buffer vessel B (compare FIG. 4) was fed into the side of a column operated under normal pressure (compare stream (g1) in FIG. 4). This column was a distillation column (dimensions 33.7×3200 mm, wall thickness 2.6 mm) filled with packing (glass rings of dimensions 4×4 mm), in which about 22 theoretical separation stages were realized and which operated at a reflux ratio of 1:1. A column unit with jacket heating formed the lower end of the column mentioned. At the upper end of this column was a horizontal double-tube condenser operated with cooling water.

On average, 139 g/hour of a mixture which comprised on average 86 mol % of methanol, 11% of dimethyl carbonate and water and was passed into buffer vessel C (compare FIG. 4) were obtained as the top product of the distillation (compare stream (m) in FIG. 4). The bottom discharge of on average 82 g/hour (compare stream (p) in FIG. 4) contained water and, in particular, water-soluble salts.

EXAMPLE 2

The catalyst employed was that described in Example 1.

Preparation of Dimethyl Carbonate 960 ml of the catalyst were introduced into a tube-bundle reactor about 900 mm long made of material 1.4571 and comprising 4 reaction tubes (dimensions of the tubes: 25.0× 800 mm, wall thickness 2.0 mm), the catalyst filling height being about 700 mm.

Figure 6:
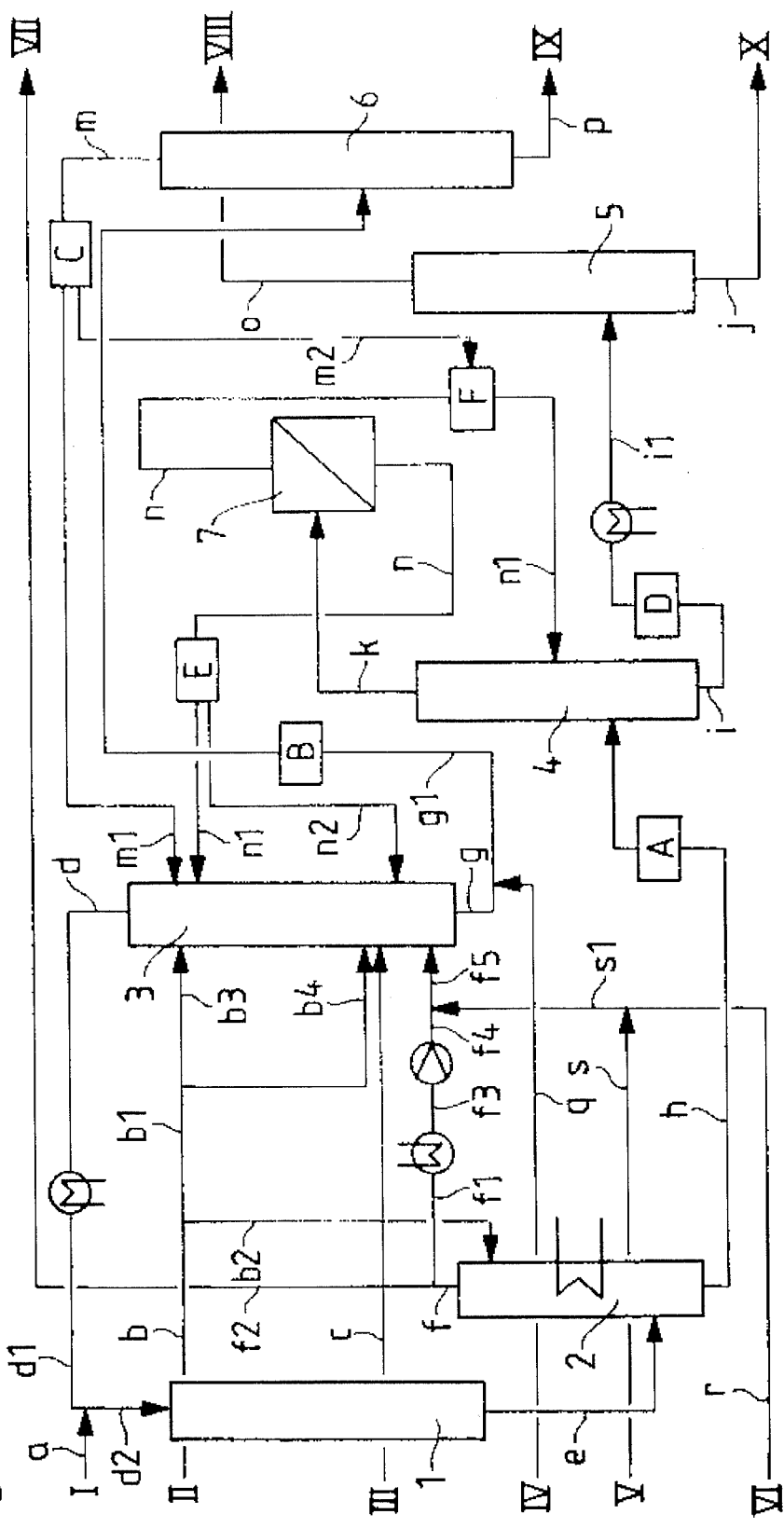

On average 4923 g/hour of a mixture, heated to about 90° C. by means of a prior tube-bundle heat exchanger, which comprised 13.2 mol % of carbon monoxide, 2.2 mol % of carbon dioxide, 15.1 mol % of methyl nitrite, 60.0 mol % of nitrogen, 5.1 mol % of methanol, 0.7 mol % of dimethyl carbonate, 3.3 mol % of nitrogen monoxide and 0.2 mol % of water (compare stream (d2) in FIG. 6) were allowed to flow in under 3130 mbar. In continuous operation, this gas mixture was composed of the gas flowing out at the top of the methyl nitrite reactor (compare stream (d) in FIG. 6) and about 128 g/hour of carbon monoxide freshly metered in (compare stream (a) in FIG. 6). The cooling (water) applied to the reactor was automatically regulated such that the gas stream leaving the reactor (compare stream (e) in FIG. 6) had a temperature of about 120° C. This gas stream was passed into the side of a scrubber/condenser (dimensions: 600×48.3 mm, wall thickness 2.6 mm) filled with glass Raschig rings (4×4 mm), in which partial condensation took place. At the top of this apparatus was attached a tube-bundle heat exchanger condensing on the jacket side, which comprised 7 tubes of dimensions 2000×10 mm (wall thickness 1 mm) and was regulated by cooling with cold water (temperature <10° C.) such that the gas emerging downstream of this condenser (compare stream (f) in FIG. 6) had a temperature of about 15° C. Under a pressure of 3020 mbar, which was thereby established, this gas comprised on average 10.7 mol % of carbon monoxide, 2.4 mol % of carbon dioxide, 9.6 mol % of methyl nitrite, 63.8 mol % of nitrogen, 2.6 mol % of methanol, 0.8 mol % of dimethyl carbonate and 10.0 mol % of nitrogen monoxide. The bottom stream (compare stream (h) in FIG. 6), of on average 526 g/hour, was discharged at a temperature of about 47° C., comprised 46.3 mol % of methanol, 49.2 mol % of dimethyl carbonate, 2.2 mol % of dimethyl oxalate and 2.3 mol % of water and was passed into buffer vessel A (compare FIG. 6).

About 0.2% by weight of the gas stream obtained at the top of the scrubber/condenser was removed continuously from the circulation in order to prevent concentration of gaseous by-products within the circulatory process (compare stream (f2) in FIG. 6). The gas which reined was brought to a pressure of about 3250 mbar and a temperature of about 28° C. via a heat exchanger and a piston compressor, combined with on average an additional 2.4 g/hour of nitrogen monoxide (compare stream (3) in FIG. 6) and 4.9 g/hour of nitrogen (compare stream (s) in FIG. 6) and fed with about 56 g/hour of fresh methanol (compare stream (b4) in FIG. 6) and about 71 g/hour of oxygen (compare stream c) in FIG. 6) into the lower part of the methyl nitrite reactor (compare apparatus 3 in FIG. 6) such that mixing of all the reactants was as sudden and complete as possible, without safety-critical concentration ranges of flammable mixtures being thereby entered.

This was effected such that the circulating gas was mixed with the freshly metered-in gases nitrogen monoxide (compare stream (r) in FIG. 6) and nitrogen (compare stream (s) in FIG. 6) within a first static mixer element, the methanol was sprayed in directly afterwards via a one-component nozzle and, immediately after the addition of methanol and still before the subsequent static mixer element in which all the reaction components then present are mixed intensively, oxygen was fed in. On average 225 g/hour of fresh methanol (compare stream (b3) in FIG. 6), 111 g/hour of the mixture comprising chiefly methanol (compare stream (m1) in FIG. 6), which was removed from buffer vessel C (compare FIG. 6) and comprised on average about 11 g/hour of dimethyl carbonate and about 3 g/hour of water, and 155 g/hour of the mixture essentially comprising methanol (compare stream (n1) in FIG. 6), which was removed from buffer vessel E (compare FIG. 6) were thereby pumped into the upper part of the reactor. The methyl nitrite reactor (dimensions: 2200× 48.3 mm, wall thickness 2.6 mm) was a reaction vessel containing packing (glass rings of dimensions 4×4 mm), which had an internal free volume of about 2.25 l.

At the top of this apparatus was attached a tube-bundle heat exchanger condensing on the jacket side, which comprised 7 tubes of dimensions 10×1000 mm (wall thickness 1 mm) and the cooling capacity of which, by cooling with cold water (temperature <15° C.) was regulated such that the gas emerging downstream of this condenser (compare stream (d) in FIG. 6) had a temperature of about 28° C. It was on average under a pressure of about 3140 mbar and was recycled continuously into the dimethyl carbonate reactor (see above).

The liquid bottom stream (compare stream (g) in FIG. 6) of on average 220 g/hour was discharged at a temperature of about 28° C., contained 39 mol % of methanol, about 5 mol % of dimethyl carbonate and 56 mol % of water and, after neutralization of the small amounts of nitric acid contained therein, was passed into buffer vessel B (compare FIG. 6).

The hot mixture at about 45° C. contained in buffer vessel A was fed into the side of a continuously operating pressure column (apparatus 4 in FIG. 6) which was operated under a pressure of about 3000 mbar. A column unit with jacket heating formed the lower end of this column. At the upper end of the column was a horizontal double-tube condenser operated with cooling water.

The pressure column was a distillation column (dimensions 33.7×2500 mm, wall thickness 2.6 mm) filled with packing (glass rings of dimensions 4×4 mm), in which about 15 theoretical separation stages were realized and which operated at a reflux ratio of 1.5:1. The pressure column furthermore was also charged continuously with the contents of buffer vessel F, which was fed from the retained material of the pervaporation (compare stream (l), FIG. 6) and a part stream of on average about 28 g/hour of the top product of the waste water column removed from buffer vessel C (stream (m2), compare FIG. 6) (see below). A column unit with jacket heating formed the lower end of the pressure column. At the upper end of the pressure column was a horizontal double-tube condenser operated with cooling water.

The liquid mixture discharged at the bottom of the pressure column (compare stream (i) in FIG. 6) had a temperature of on average about 130° C. and was transferred to buffer vessel D (compare FIG. 6). The condensate obtained at the top (compare stream (k) in FIG. 6) had, after condensation, a temperature of 80° to 90° C. and comprised on average about 77 mol % of methanol, about 17 mol % of dimethyl carbonate, about 3 to 3.5 mol % of water and small amounts of low-boiling constituents.

It was fed into a pervaporation plant which was operated with a pressure of about 1.4 bar and a temperature of about 80° C. on the retained material side and with a pressure of 30 to 50 mbar and a temperature of about 0° to 3° C. on the permeate side. This apparatus was three plate modules, connected in series, which had areas of in each case 200 cm$^2$ and contained membranes of the type AERK 300.

The permeate comprised on average about 94 mol % of methanol, 1.5 to 2 mol % of dimethyl carbonate and 4 to 5 mol % of water and was passed into buffer vessel E, while the retained material of on average 127 g/hour was fed to buffer vessel F.

The substance mixture in buffer vessel D (compare FIG. 6), after being cooled to about 60° C. by means of an interpolated simple tube-bundle heat exchanger, the cooling capacity of which was regulated automatically such that the emerging liquid had the desired temperature, was fed into the side of a continuously operating column operated under normal pressure (compare stream (i1) in FIG. 6).

This column was a distillation column (dimensions 33.7× 2200 mm, wall thickness 2.6 mm) filled with packing (glass rings of dimensions 4×4 mm), in which about 15 theoretical separation stages were realized and which operated at a reflux ratio of 1:1. A column unit with jacket heating formed the lower end of the column mentioned. At the upper end of this column was a horizontal double-tube condenser operated with cooling water.

On average, 375 g/hour of dimethyl carbonate with a purity of >99.7% (gas chromatography) were obtained as the top product of the distillation (compare stream (o) in FIG. 6). The bottom discharge contained high-boiling constituents, essentially, to the extent of more than 90%, dimethyl oxalate.

The neutralized bottom discharge of the methyl nitrite reactor (compare apparatus 3 in FIG. 6) in buffer vessel B (compare FIG. 6) was fed into the side of a column operated under normal pressure (compare stream (g1) in FIG. 6). This column was a distillation column (dimensions 33.7×3200 mm, wall thickness 2.6 mm) filled with packing (glass rings of dimensions 4×4 mm), in which about 22 theoretical separation stages were realized and which operated at a reflux ratio of 1:1. A column unit with jacket heating formed the lower end of the column mentioned. At the upper end of the column was a horizontal double-tube condenser operated with cooling water.

On average, 139 g/hour of a mixture which comprised on average 86 mol % of methanol, 11% of dimethyl carbonate and water and was passed into buffer vessel C (compare FIG. 6) were obtained as the top product of the waste water distillation (compare stream (m) in FIG. 6). The bottom discharge (compare stream (p) in FIG. 6) contained water and, in particular, water-soluble salts.

EXAMPLE 3

Preparation of the Catalyst 13.33 g of $PdCl_2$ were dissolved in 64 ml of water with the addition of 6.37 g of lithium chloride. 1000 ml of $\gamma$-$Al_2O_3$ (SPH 535 from RHONE POULENC) were impregnated with this solution and then dried in a stream of nitrogen. The resulting catalyst was diluted with the same volume of inert glass bodies of the same dimensions (diameter about 2 mm).

Preparation of Dimethyl Carbonate 970 ml of the catalyst diluted as described above were introduced into a tube reactor made of material 1.4571 and about 3m in length (dimensions of the reaction tube: 21×2900 mm, wall thickness 2 mm), the filling height of the catalyst being about 2800 mm. The reactor was provided with a jacket through which a cooling liquid flowed. The average temperature of the cooling medium was 70° C.

Figure 10:
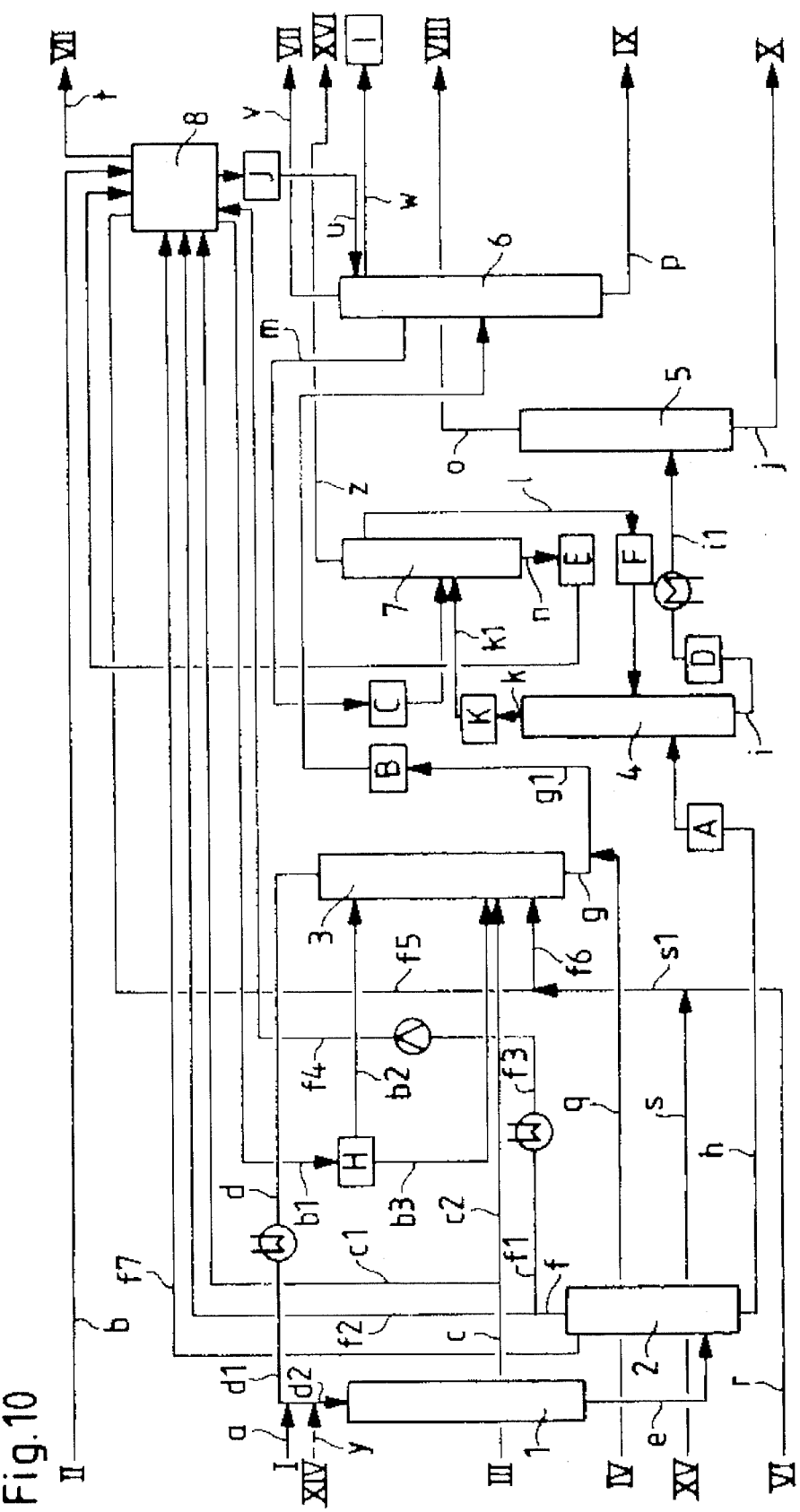

On average, 1874.2 g/hour of a mixture, heated to about 62° C. by means of a prior tube-bundle heat exchanger, which comprised on average 13.2 mol % of carbon monoxide, 43.2 mol % of carbon dioxide, 25.8 mol % of methyl nitrite, 6.6 mol % of methanol, 0.9 mol % of dimethyl carbonate, 0.4 mol % of nitrogen monoxide, 0.1 mol % of water, 1000 ppm of hydrogen chloride and 9.7 mol % of low-boiling constituents (methyl formate, formaldehyde dimethyl acetal, methyl chloride, nitrogen, methane and hydrogen) (compare stream (d2) in FIG. 10) were allowed to flow in under 3130 mbar. In continuous operation, this gas mixture was composed of the gas flowing out at the top of the methyl nitrite reactor (compare stream (d) in FIG. 10), about 125.3 g/hour of freshly metered-in carbon monoxide (compare stream (a) in FIG. 10) and about 1.2 g/hour of freshly metered-in hydrogen chloride (compare stream (y) in FIG. 10). The gas stream leaving the reactor (compare stream (e) in FIG. 10) had a temperature of about 70° C. This gas stream was passed into the side of a scrubber/condenser (dimensions: 2000×33.7 mm, wall thickness 1.6 mm) filled with glass Raschig rings (4×4 mm), in which partial condensation took place. At the top of this apparatus was attached a tube-bundle heat exchanger condensing on the jacket side, which comprised 7 tubes of dimensions 1000×10 mm (wall thickness 1 mm) and was regulated by cooling with cold water (temperature <15° C.) such that the gas emerging downstream of this condenser (compare stream (f) in FIG. 10) had a temperature of about 30° C. Under a pressure of 3010 mbar thereby established, this gas comprised on average 3.0 mol % of carbon monoxide, 48.9 mol % of carbon dioxide, 5.8 mol % of methyl nitrite, 5.4 mol % of methanol, 1.9 mol % of dimethyl carbonate, 23.7 mol % of nitrogen monoxide, 0.1 mol % of $H_2O$ and 11.2 mol % of the abovementioned low-boiling constituents. The bottom stream (compare stream (h) in FIG. 10) of on average 366.8 g/hour was discharged at a temperature of about 63° C., comprised 13.2 mol % of methanol, 85.7 mol % of dimethyl carbonate, 0.7 mol % of dimethyl oxalate and 0.2 mol % of water and was passed to buffer vessel A (compare FIG. 10).

A liquid stream of on average 16.7 g/hour (compare stream (f7) in FIG. 10) was removed from the reflux of the condenser and fed to buffer vessel G (compare FIG. 11), the contents of which were stirred magnetically. It had a temperature of about 30° C. and comprised on average 60.6 mol % of methanol, 37.4 mol % of dimethyl carbonate, 1.3 mol % of water and 0.7 mol % of the low-boiling constituents mentioned.

About 3.5% by weight of the gas stream obtained at the top of the scrubber/condenser (compare stream (f) in FIG. 10) were removed continuously from the circulation and fed to the lower region of the low-boiling constituents scrubber (compare apparatus 8c in FIG. 11) to prevent concentration of gaseous by-products in the circulatory process (compare stream (f2) in FIG. 10). The gas which reined was brought to a pressure of about 3250 mbar and a temperature of about 42° C. via a heat exchanger and a piston compressor (compare streams (f3), (f4) in FIG. 10) and passed into the lower region of the methyl nitrite desorber (compare apparatus 8a in FIG. 11). The gas stream obtained at the top of this methyl nitrite desorber (compare stream (f5) in FIG. 10) had a temperature of about 26° C. and comprised on average 3.0 mol % of carbon monoxide, 49.9 mol % of carbon dioxide, 6.4 mol % of methyl nitrite, 5.1 mol % of methanol, 0.4 mol % of dimethyl carbonate, 24.0 mol % of nitrogen monoxide and 11.2 mol % of the abovementioned low-boiling constituents.

This stream was combined with on average an additional 6.2 g/hour of nitrogen monoxide (compare stream (r) in FIG. 10) and 12.3 g/hour of carbon dioxide (compare streams (s), (s1) in FIG. 10) (compare stream (f6) in FIG. 10) and fed with a stream of about 96.5 g/hour (compare stream (b3) in FIG. 10) from buffer vessel H (compare FIG. 10) and about 69.3 g/hour of oxygen (compare stream (c2) in FIG. 10) into the lower section of the methyl nitrite reactor (compare apparatus 3 in FIG. 10) such that all the reactants were mixed as suddenly and completely as possible, without safety-critical concentration ranges of flammable components thereby being entered.

In the case of the example described here, this was effected in a manner such that the circulating gas was mixed with the freshly metered-in gases carbon monoxide (compare stream (r) in FIG. 10) and carbon dioxide (compare stream (r), (s1) in FIG. 10) within a first static mixer element, the stream from buffer vessel H (compare FIG. 10) comprising essentially methanol was sprayed in directly afterwards via a one-component nozzle and, immediately after the addition of methanol and still before the subsequent static mixer element, in which all the reaction components then present were mixed intensively, oxygen (compare stream (c2) in FIG. 10) was fed in.

A stream of on average 386.2 g/hour (compare stream (b2) in FIG. 10) was thereby pumped from buffer vessel H (compare FIG. 6) into the upper part of the reactor.

The methyl nitrite reactor (dimensions: 7000×51 mm, wall thickness 1.6 mm) was a reaction vessel which contained a packing (glass rings of dimensions 4×4 mm) and had an internal free volume of about 12.6 l.

To the top of this apparatus was attached a tube-bundle heat exchanger condensing on the jacket side, which comprised 7 tubes of dimensions 10×1000 mm (wall thickness 1 mm) and the cooling capacity of which was regulated by cooling with cold water (temperature <15° C.) such that the gas emerging downstream of this condenser (compare stream (d) in FIG. 10) had a temperature of about 34° C. It was on average under a pressure of about 3140 mbar and was recycled continuously into the dimethyl carbonate reactor (see above).

The liquid bottom stream (compare stream (g) in FIG. 10) of on average 224.8 g/hour was discharged at a temperature of about 51° C., comprised 39.1 mol % of methanol, 5.4 mol % of dimethyl carbonate, 54.4 mol % of water and 1.1 mol % of nitric acid and, after neutralization of the nitric acid contained therein with about 6.6 g/hour of 50% strength sodium hydroxide solution (compare stream (q) in FIG. 10), was passed (compare stream (g1) in FIG. 10) into buffer vessel B (compare FIG. 10).

About 366.8 g/hour of the mixture in buffer vessel A and 397.0 g/hour of the mixture in buffer vessel F (compare FIG. 10) were fed into the side of a continuously operating pressure column (apparatus 4 in FIG. 10) which was operated in a pressure range from 10072 (bottom) to 10030 mbar (top). This pressure column was a distillation column (dimensions 51×3000 mm, wall thickness 1.6 mm) filled with packing (glass rings of dimensions 4×4 mm), in which about 16 theoretical separation stages were realized and which operated at a reflux ratio of 1.44:1. A column unit with jacket heating formed the lower end of the pressure column. At the upper end of the pressure column was a horizontal double-tube condenser operated with cooling water.

The liquid mixture discharged at the bottom (compare stream (i) in FIG. 10) of on average 380.0 g/hour had a temperature of about 185° C. It comprised 99.1 mol % of dimethyl carbonate and 0.8 mol % of dimethyl oxalate and was passed into buffer vessel D (compare FIG. 10).

The condensate obtained at the top (compare stream (k) in FIG. 10) of on average 383.8 g/hour had a temperature of about 120° C. and comprised on average about 88.1 mol % of methanol, 8.7 mol % of dimethyl carbonate, 0.1 mol % of water and 3.1 mol % of low-boiling constituents. It was fed to buffer vessel C (compare FIG. 10), the contents of which were stirred magnetically and into which stream (m) (compare FIG. 10) of on average 179.5 g/hour, which originated from the waste water distillation (compare apparatus 6 in FIG. 10) furthermore was passed.

A stream of about 563.3 g/hour (compare stream (k1) in FIG. 10) was fed from this buffer vessel into the side of a continuously operating distillation column operated under normal pressure (compare apparatus 7 in FIG. 10), in which separation into a bottom discharge (compare stream (n) in FIG. 10) of on average 161.3 g/hour, the temperature of which was about 67° C. and which comprised about 99.0 mol % of methanol, 0.7 mol % of dimethyl carbonate and 0.3 mol % of water and which was transferred to buffer vessel E (compare FIG. 10), and into a top product (compare stream (l) in FIG. 10) of on average 397.0 g/hour, which comprised about 84.4 mol % of methanol, 12.6 mol % of dimethyl carbonate and 3.0 mol of low-boiling constituents and which was passed as condensate with a temperature of about 62° C. into buffer vessel F (compare FIG. 10) took place.

This column was a distillation column (dimensions: 51×5500 mm, wall thickness: 1.6 mm) filled with packing (glass rings of dimensions 4×4 mm), in which about 36 theoretical separation stages were realized and which operated at a reflux ratio of 1.5:1. A column unit with jacket heating formed the lower end of the column. At the upper end of the column was a horizontal double-tube condenser which was operated with cooling water and from which a gaseous stream of on average 4.9 g/hour, which comprised about 0.1 mol % of carbon dioxide, 75.8 mol % of methanol, 11.7 mol % of dimethyl carbonate and 12.3 mol % of low-boiling constituents (compare stream (z) in FIG. 10) was removed, this stream being further worked up, where appropriate, with the aim of recovering the useful substances contained therein (not described in the present example).

About 380.0 g/hour of the substance mixture in buffer vessel D (compare FIG. 10), after being cooled to about 51° C. by means of an interpolated simple tube-bundle heat exchanger, the cooling capacity of which was automatically regulated such that the emerging liquid had the desired temperature, were fed into the side of a continuously operating column operated under normal pressure (compare stream (i1) in FIG. 10). This column was a distillation column (dimensions 33.7×1500 mm, wall thickness 1.6 mm) filled with packing (glass rings of dimensions 4×4 mm), in which about 14 theoretical separation stages were realized and which operated at a reflux ratio of 0.2:1. A column unit with jacket heating formed the lower end of the column. At the upper end of the column was a horizontal double-tube condenser operated with cooling water.

On average, 372.2 g/hour of dimethyl carbonate with a purity of 99.9% (gas chromatography) were obtained as the top product of the distillation (compare stream (o) in FIG. 10). The bottom discharge of on average 7.6 g/hour contained 56.2 mol % of dimethyl carbonate and 43.8 mol % of dimethyl oxalate.

About 231.3 g/hour (compare stream (g1) in FIG. 10) of the neutralized bottom discharge of the methyl nitrite reactor (compare apparatus 3 in FIG. 10) in buffer vessel B (compare FIG. 10) and about 61.8 g/hour (compare stream (u) in FIG. 10) of the bottom discharge of the low-boiling constituents scrubber (compare apparatus 8c in FIG. 11) in buffer vessel J (compare FIG. 10) were in each case fed into the side of the column operated under normal pressure in the central and in the upper region. This column was a distillation column (dimensions 42×3000 mm, wall thickness 1.6 mm) filled with packing (glass rings of dimensions 4×4 mm), in which about 20 theoretical separation stages were realized and which operated at a reflux ratio of 49.8:1. A column unit with jacket heating formed the lower end of the column. At the upper end of the column was a horizontal double-tube condenser which was operated with cooling water and from which a waste gas stream of on average 10.1 g/hour was removed, the stream comprising about 18.1 mol % of carbon dioxide, 38.1 mol % of methyl nitrite, 17.9 mol % of methanol, 3.1 mol % of dimethyl carbonate and 22.3 mol % of low-boiling constituents.

On average, 13.5 g/hour of a gas mixture which comprised on average 0.5 mol % of methyl nitrite, 82.8 mol % of methanol, 13.4 mol % of dimethyl carbonate and 3.2 mol % of low-boiling constituents were obtained as the top product of the distillation (compare stream (w) in FIG. 10) and was passed (compare stream (w) in FIG. 10) to buffer vessel I (compare FIG. 10), the contents of which were subjected to continuous or discontinuous a working up operation, where appropriate, with the aim of recovering useful substances contained therein (not described in the present example). The bottom discharge (compare stream (p) in FIG. 10) of on average 90.0 g/hour contained 98.1 mol % of water and 1.9 mol % of sodium nitrate.

A liquid side stream of on average 179.5 g/hour, which had a temperature of about 66° C., comprised about 91.3 mol % of methanol, 8.5 mol % of dimethyl carbonate and 0.2 mol % of water and was fed to buffer vessel C (compare FIG. 6), was removed from the upper part of the column.

Figure 11:
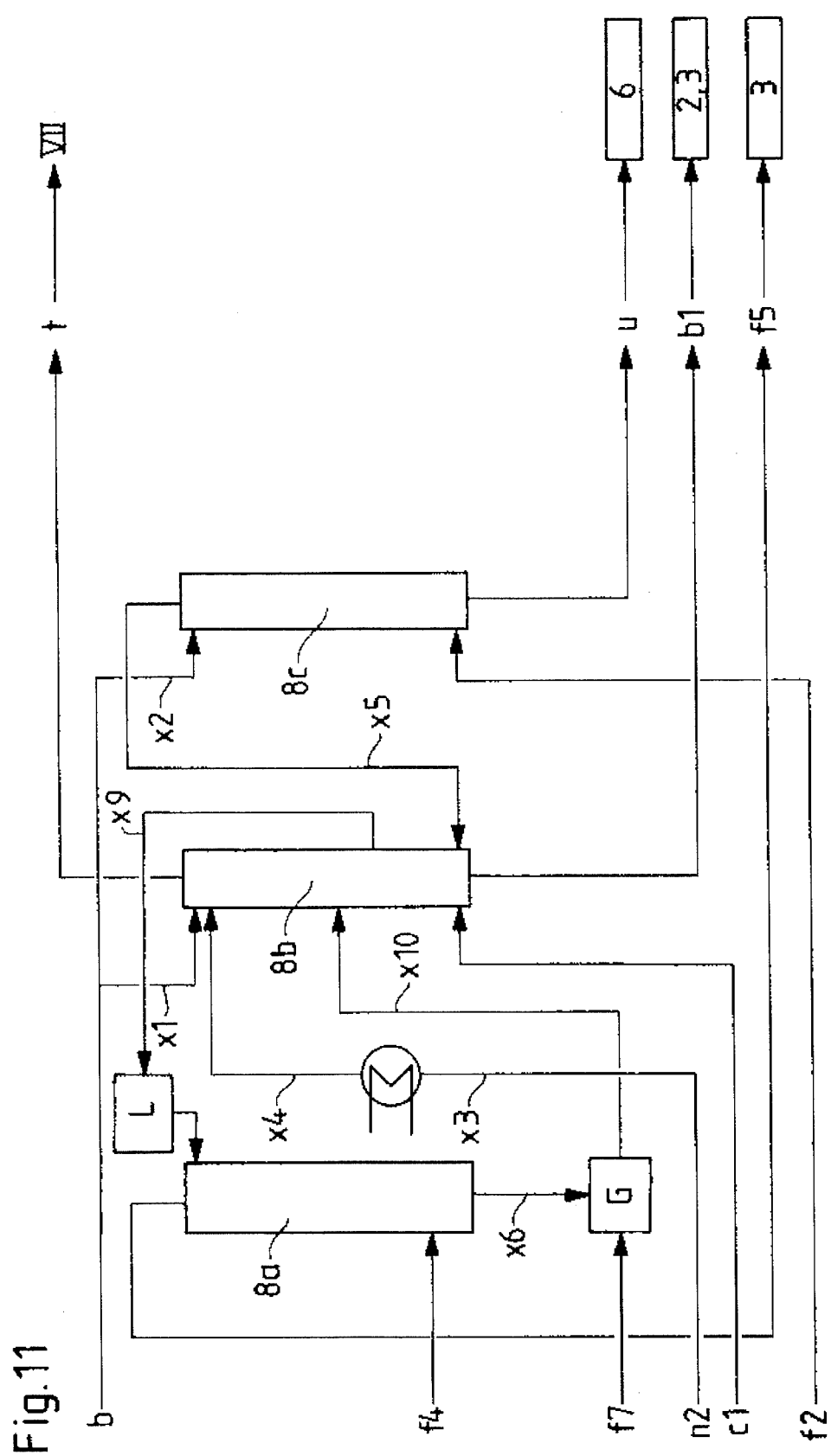

The low-boiling constituents scrubber (compare apparatus 8c in FIG. 11), into the lower part of which the gaseous stream (f2) described above (compare FIG. 7) was fed, was a column (dimensions: 33.7×2000 mm, wall thickness: 1.6 mm) filled with packing (glass rings of dimensions 4×4 mm), which was operated at a pressure of 3000 mbar and a temperature of 0° C. and into the upper part of which on average 50.0 g/hour of fresh methanol, which had a temperature of about 15° C., was fed (compare streams (b), (x2) in FIG. 11).

The streams removed from this column, which had a temperature of 0° C., comprised the bottom discharge of on average 61.8 g/hour (compare stream (u) in FIG. 11), which was passed into buffer vessel J (compare FIG. 10) and which comprised about 1.6 mol % of carbon dioxide, 4.2 mol % of methyl nitrite, 90.7 mol % of methanol, 1.4 mol % of dimethyl carbonate and 2.0 mol % of low-boiling constituents, and the gaseous top stream of on average 40.4 g/hour (compare stream (x5) in FIG. 11), which comprised about 3.6 mol % of carbon monoxide, 56.4 mol % of carbon dioxide, 1.3 mol % of methanol, 28.6 mol % of nitrogen monoxide and 10.1 mol % of low-boiling constituents and was passed, together with about 2.5 g/hour of oxygen (compare stream (c1) in FIG. 11) into the lower part of the methyl nitrite after-reactor (compare apparatus 8b in FIG. 11).

This methyl nitrite after-reactor was a column (dimensions: 33.7×3000 mm, wall thickness: 1.6 mm) filled with packing (glass rings of dimensions 4×4 mm), which was operated at a pressure of 3126 mbar and a temperature of about 22° C. and into the upper part of which were fed on average 241.9 g/hour of fresh methanol, which had a temperature of about 15° C. (compare streams (b), (x1) in FIG. 11) and 161.3 g/hour of the liquid mixture from buffer vessel E (compare FIG. 10), which was cooled to about 15° C. by means of a prior tube-bundle heat exchanger (compare streams (x3), (x4) in FIG. 11). On average, 1502.3 g/hour (compare stream (x10) in FIG. 11) were fed from buffer vessel G (compare FIG. 11), the contents of which were stirred magnetically, into the central region of the column.

The liquid stream (compare stream (x9) in FIG. 11) of on average 1448.2 g/hour which was removed from the central part of the column, had a temperature of 21.9° C. and comprised about 1.0 mol % of carbon dioxide, 0.9 mol % of methyl nitrite, 91.2 mol % of methanol, 4.9 mol % of dimethyl carbonate, 1.4 mol % of water and 0.6 mol % of low-boiling constituents, was passed into buffer vessel L (compare FIG. 11). The liquid bottom discharge (compare stream (b1) in FIG. 11) of on average 482.7 g/hour, which had a temperature of about 21.9° C. and comprised about 1.0 mol % of carbon dioxide, 0.9 mol % of methyl nitrite, 91.2 mol % of methanol, 4.9 mol % of dimethyl carbonate, 1.4 mol % of water and 0.6 mol % of low-boiling constituents, was passed into buffer vessel H (compare FIG. 10). The gaseous top stream (waste gas) (compare stream (t) in FIG. 11) of on average 17.5 g/hour had a temperature of 17.5° C. and comprised about 8.3 mol % of carbon monoxide, 73.5 mol % of carbon dioxide, 0.1 mol % of oxygen, 3.6 mol % of methanol, 4.8 mol % of nitrogen, 4.9 mol % of methane and 4.9 mol % of hydrogen.

About 1448.2 g/hour were fed from buffer vessel L into the upper region of the methyl nitrite desorber (compare apparatus 8a in FIG. 11), into the lower region of which the stream (f4) already described (compare FIG. 11) was fed. This methyl nitrite desorber is a column (dimensions 51×2000 mm, wall thickness 1.6 mm) filled with packing (glass rings of dimensions 4×4 mm), which was operated at a pressure of 3200 mbar and a temperature of about 26° C. The liquid bottom discharge (compare stream (x6) in FIG. 11) of on average 1485.6 g/hour, which had a temperature of about 15° C. and comprised about 0.7 mol % of carbon dioxide, 0.4 mol % of methyl nitrite, 90.6 mol % of methanol, 6.2 mol % of dimethyl carbonate, 14 mol % of water and 0.7 mol % of low-boiling constituents, was passed into buffer vessel G (compare FIG. 11). The gaseous top stream (compare stream (f5) in FIG. 11), which has already been described above, was fed to the methyl nitrite synthesis (compare apparatus 3 in FIG. 10).

EXAMPLE 4

Preparation of the Catalyst

The catalyst employed was that described in Example 3, diluted with glass bodies.

Preparation of Dimethyl Carbonate 970 ml of the catalyst diluted as described above were introduced into a tube reactor made of material 1.4571 and about 3m in length (dimensions of the reaction tube: 21×2900 mm, wall thickness 2 mm), the filling height of the catalyst being about 2800 mm. The reactor was provided with a jacket through which a cooling liquid flowed. The average temperature of the cooling medium was 70° C.

Figure 13:
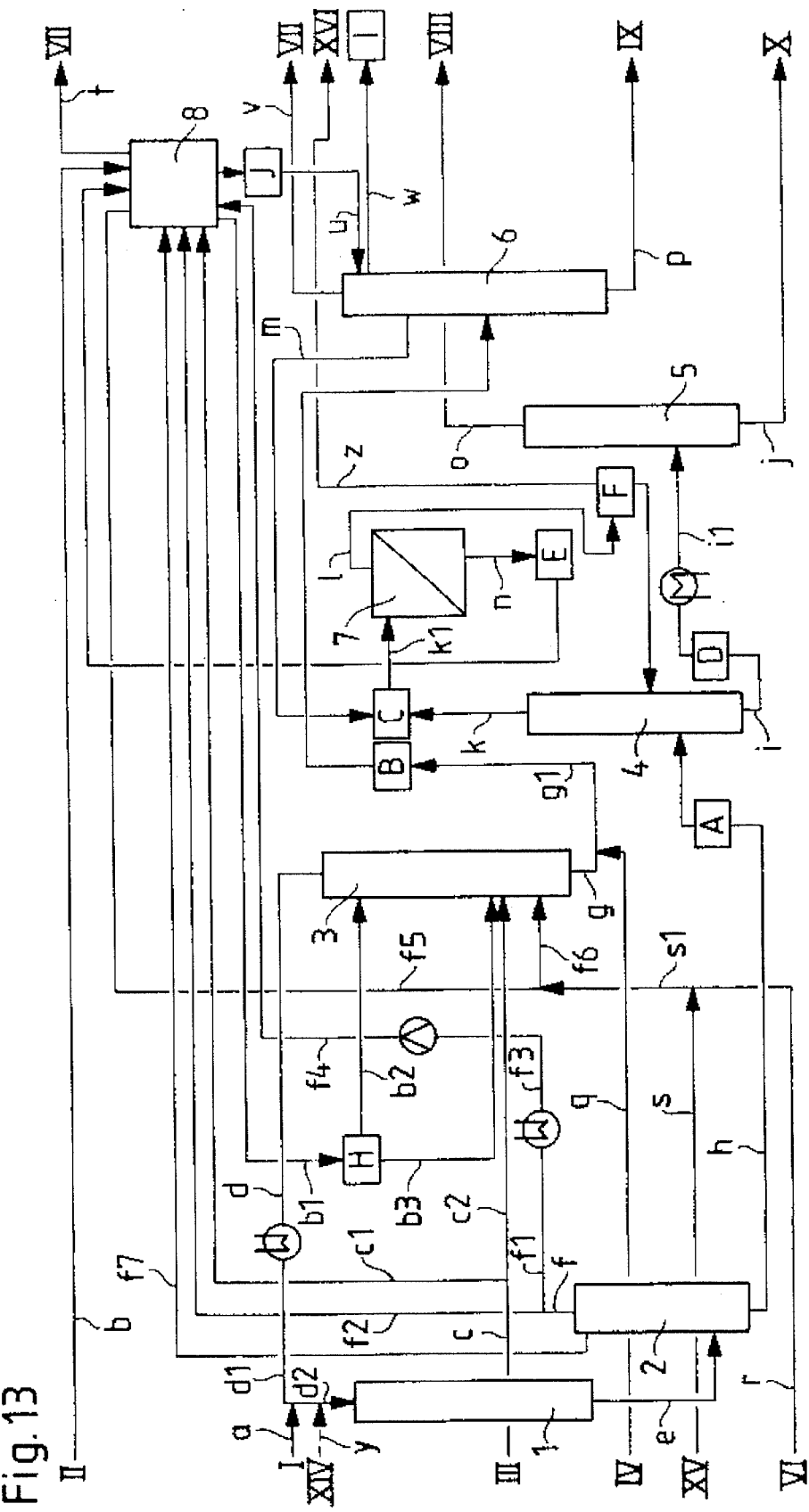

On average, 1878.8 g/hour of a mixture, heated to about 62° C. by means of a prior tube-bundle heat exchanger, which comprised on average 13.2 mol % of carbon monoxide, 43.1 mol % of carbon dioxide, 25.8 mol % of methyl nitrite, 6.6 mol % of methanol, 1.0 mol % of dimethyl carbonate, 0.4 mol % of nitrogen monoxide, 0.1 mol % of water, 1000 ppm of hydrogen chloride and 9.7 mol % of low-boiling constituents (methyl formate, formaldehyde dimethyl acetal, methyl chloride, nitrogen, methane and hydrogen) (compare stream (d2) in FIG. 13) were allowed to flow in under 3130 mbar. In continuous operation, this gas mixture was composed of the gas flowing out at the top of the methyl nitrite reactor (compare stream (d), (d1) in FIG. 13), about 125.5 g/hour of freshly metered-in carbon monoxide (compare stream (a) in FIG. 13) and about 1.2 g/hour of freshly metered-in hydrogen chloride (compare stream (y) in FIG. 13). The gas stream leaving the reactor (compare stream (e) in FIG. 13) had a temperature of about 70° C. This gas stream was passed into the side of a scrubber/condenser (dimensions: 2000×33.7 mm, wall thickness 1.6 mm) filled with glass Raschig rings (4×4 mm), in which partial condensation took place. At the top of this apparatus was attached a tube-bundle heat exchanger condensing on the jacket side, which comprised 7 tubes of dimensions 1000×10 mm (wall thickness 1 mm) and was regulated by cooling with cold water (temperature <15° C.) such that the gas emerging downstream of this condenser (compare stream (f) in FIG. 13) had a temperature of about 30° C. Under a pressure of 3010 mbar thereby established, this gas comprised on average 3.0 mol % of carbon monoxide, 48.9 mol % of carbon dioxide, 5.8 mol % of methyl nitrite, 5.4 mol % of methanol, 1.9 mol % of dimethyl carbonate, 23.7 mol % of nitrogen monoxide, 0.1 mol % of $H_2O$ and 11.2 mol % of the abovementioned low-boiling constituents. The bottom stream (compare stream (h) in FIG. 13) of on average 366.8 g/hour was discharged at a temperature of about 63° C., comprised 13.2 mol % of methanol 85.6 mol % of dimethyl carbonate, 0.7 mol % of dimethyl oxalate and 0.2 mol % of water and was passed to buffer vessel A (compare FIG. 13).

A liquid stream of on average 16.7 g/hour (compare stream (f7) in FIG. 13) was removed from the reflux of the condenser and fed to buffer vessel G (compare FIG. 11), the contents of which were stirred magnetically. It had a temperature of about 30° C. and comprised on average 60.4 mol % of methanol, 37.5 mol % of dimethyl carbonate, 1.3 mol % of water and 0.7 mol % of low-boiling constituents.

About 3.5% by weight of the gas stream obtained at the top of the scrubber/condenser (compare stream (f) in FIG. 13) were removed continuously from the circulation and fed to the lower region of the low-boiling constituents scrubber (compare apparatus 8c in FIG. 11) to prevent concentration of gaseous by-products in the circulatory process (compare stream (f2) in FIG. 13). The gas which reined was brought to a pressure of about 3250 mbar and a temperature of about 42° C. via a heat exchanger and a piston compressor (compare streams (f3), (f4) in FIG. 13) and passed into the lower region of the methyl nitrite desorber (compare apparatus 8a in FIG. 11). The gas stream obtained at the top of this methyl nitrite desorber (compare stream (f5) in FIG. 13) had a temperature of about 26° C. and comprised on average 3.0 mol % of carbon monoxide, 49.8 mol % of carbon dioxide, 6.4 mol % of methyl nitrite, 5.0 mol % of methanol, 0.5 mol % of dimethyl carbonate, 24.0 mol % of nitrogen monoxide and 11.2 mol % of the abovementioned low-boiling constituents.

This stream was combined with on average an additional 6.2 g/hour of nitrogen monoxide (compare stream (r) in FIG. 13) and 12.7 g/hour of carbon dioxide (compare streams (s), (s1) in FIG. 13) (compare stream (f6) in FIG. 13) and fed with a stream of about 97.5 g/hour (compare stream (b3) in FIG. 13) from buffer vessel H (compare FIG. 13) and about 69.4 g/hour of oxygen (compare stream (c2) in FIG. 13) into the lower section of the methyl nitrite reactor (compare apparatus 3 in FIG. 13) such that all the reactants were mixed as suddenly and completely as possible, without safety-critical concentration ranges of flammable components thereby being entered.

In the case of the example described here, this was effected in a manner such that the circulating gas was mixed with the freshly metered-in gases carbon monoxide (compare stream (r), (s1) in FIG. 13) and carbon dioxide (compare stream (s) in FIG. 13) within a first static mixer element, the stream from buffer vessel H (compare FIG. 13) comprising essentially methanol was sprayed in directly afterwards via a one-component nozzle and, immediately after the addition of methanol and still before the subsequent static mixer element, in which all the reaction components then present were mixed intensively, oxygen (compare stream (c2) in FIG. 13) was fed in.

A stream of on average 390.1 g/hour (compare stream (b2) in FIG. 13) was thereby pumped from buffer vessel H (compare FIG. 13) into the upper part of the reactor.

The methyl nitrite reactor (dimensions: 7000×51 mm, wall thickness 1.6 mm) was a reaction vessel which contained a packing (glass rings of dimensions 4×4 mm) and had an internal free volume of about 12.6 l.

To the top of this apparatus was attached a tube-bundle heat exchanger condensing on the jacket side, which comprised 7 tubes of dimensions 10×1000 mm (wall thickness 1 mm) and the cooling capacity of which was regulated by cooling with cold water (temperature <15° C.) such that the gas emerging downstream of this condenser (compare stream (d) in FIG. 13) had a temperature of about 34° C. It was on average under a pressure of about 3140 mbar and was recycled continuously into the dimethyl carbonate reactor (see above).

The liquid bottom stream (compare stream (g) in FIG. 13) of on average 229.1 g/hour was discharged at a temperature of about 51° C., comprised about 38.7 mol % of methanol, 6.0 mol % of dimethyl carbonate, 53.9 mol % of water and 1.1 mol % of nitric acid and, after neutralization of the nitric acid contained therein with about 6.6 g/hour of 50% strength sodium hydroxide solution (compare stream (q) in FIG. 13), was passed (compare stream (g1) in FIG. 13) into buffer vessel B (compare FIG. 13).

About 367.9 g/hour of the mixture in buffer vessel A and about 78.0 g/hour of the mixture in buffer vessel F (compare FIG. 13) were fed into the side of a continuously operating pressure column (apparatus 4 in FIG. 13) which was operated in a pressure range from 10072 (bottom) to 10039 mbar (top). This pressure column was a distillation column (dimensions 33.7×3000 mm, wall thickness 1.6 mm) filled with packing (glass rings of dimensions 4×4 mm), in which about 10 theoretical separation stages were realized and which operated at a reflux ratio of 1.97:1. A column unit with jacket heating formed the lower end of the pressure column mentioned. At the upper end of the pressure column was a horizontal double-tube condenser operated with cooling water.

The liquid mixture discharged at the bottom (compare stream (i) in FIG. 13) of on average 379.9 g/hour had a temperature of about 185° C. It comprised 99.2 mol % of dimethyl carbonate and 0.8 mol % of dimethyl oxalate and was passed into buffer vessel D (compare FIG. 13).

The condensate obtained at the top (compare stream (k) in FIG. 13) of on average 66.0 g/hour had a temperature of about 120° C. and comprised on average about 69.1 mol % of methanol, 22.4 mol % of dimethyl carbonate, 0.5 mol % of water and 7.9 mol % of low-boiling constituents. It was fed to buffer vessel C (compare FIG. 13), the contents of which were stirred magnetically and in which stream (m) (compare FIG. 13) of on average 183.5 g/hour, which originated from the waste water distillation (compare apparatus 6 in FIG. 13) furthermore was passed. The contents of this buffer vessel were kept at 70° C. by temperature regulation and at 10 bar by pressure regulation.

From buffer vessel C (compare FIG. 13), a liquid stream of about 249.5 g/hour (compare stream (k1) in FIG. 13) on the retained material side was fed into the side of a continuously operating pervaporation plant (compare apparatus 7 in FIG. 13), in which separation into a liquid permeate (compare stream (n) in FIG. 13) of on average 167.4 g/hour, the temperature of which was about −7° C., which comprised about 98.0 mol % of methanol, 1.7 mol % of dimethyl carbonate and 0.3 mol % of water and which was transferred to buffer vessel E (compare FIG. 13) and liquid retained material (compare stream (l) in FIG. 13) of on average 82.1 g/hour, which comprised about 33.1 mol % of methanol, 58.4 mol % of dimethyl carbonate and 8.5 mol % of low-boiling constituents and was passed with a temperature of about 63° C. into buffer vessel F (compare FIG. 13) took place. The contents of this buffer vessel were kept at 70° C. by temperature regulation and at 1300 mbar by pressure regulation. The gaseous stream of on average 4.1 g/hour thereby obtained, which comprised about 0.2 mol % of carbon dioxide, 53.0 mol % of methanol, 26.1 mol % of dimethyl carbonate and 20.7 mol % of low-boiling constituents (compare stream (z) in FIG. 13) was worked up further, where appropriate, for example with the aim of recovering the useful substances contained therein (not described in the present example).

The pervaporation plant was three cells, connected in series, with membranes of the type AERK 300 from GFT, the membrane area of which was in each case 200 cm². The unit was operated with a pressure of 20 mbar and a temperature of −7° C. on the permeate side and with a pressure of 1300 mbar and a temperature of 70° C. on the retained material side.

About 379.9 g/hour of the substance mixture in buffer vessel D (compare FIG. 13), after being cooled to about 51° C. by means of an interpolated simple tube-bundle heat exchanger, the cooling capacity of which was automatically regulated such that the emerging liquid had the desired temperature, was fed into the side of a continuously operating column operated under normal pressure (compare stream (i1) in FIG. 13). This column was a distillation column (dimensions 33.7×1500 mm, wall thickness 1.6 mm) filled with packing (glass rings of dimensions 4×4 mm), in which about 14 theoretical separation stages were realized and which operated at a reflux ratio of 0.2:1. A column unit with jacket heating formed the lower end of the column. At the upper end of the column was a horizontal double-tube condenser operated with cooling water.

On average, 372.2 g/hour of dimethyl carbonate with a purity of more than 99.9% (gas chromatography) were obtained as the top product of the distillation (compare stream (o) in FIG. 13). The bottom discharge of on average 7.6 g/hour comprised 56.1 mol % of dimethyl carbonate and 43.9 mol % of dimethyl oxalate.

About 235.6 g/hour (compare stream (g1) in FIG. 13) of the neutralized bottom discharge of the methyl nitrite reactor (compare apparatus 3 in FIG. 13) in buffer vessel B (compare FIG. 13) and about 61.8 g/hour (compare stream (u) in FIG. 13) of the bottom discharge of the low-boiling constituents scrubber (compare apparatus 8c in FIG. 11) in buffer vessel J (compare FIG. 13) were in each case fed into the side of the column operated under normal pressure in the central and in the upper region. This column was a distillation column (dimensions 42×3000 mm, wall thickness 1.6 mm) filled with packing (glass rings of dimensions 4×4 mm), in which about 20 theoretical separation stages were realized and which operated at a reflux ratio of 49.8:1. A column unit with jacket heating formed the lower end of the column. At the upper end of the column was a horizontal double-tube condenser which was operated with cooling water and from which a waste gas stream of on average 10.1 g/hour was removed, the stream comprising about 18.5 mol % of carbon dioxide, 38.1 mol % of methyl nitrite, 17.9 mol % of methanol, 3.2 mol % of dimethyl carbonate and 22.2 mol % of low-boiling constituents.

On average, 13.6 g/hour of a mixture which comprised on average 0.5 mol % of methyl nitrite, 82.7 mol % of methanol, 13.5 mol % of dimethyl carbonate and 3.2 mol % of low-boiling constituents was obtained as the top product of the distillation (compare stream (w) in FIG. 13) and was passed (compare stream (w) in FIG. 13) into buffer vessel I (compare FIG. 13), the contents of which, if appropriate, were fed continuously or discontinuously to a further working up operation with the aim of recovering the useful substances contained therein. The bottom discharge (compare stream (p) in FIG. 13) of on average 90.2 g/hour contained 98.1 mol % of water and 1.9 mol % of sodium nitrate.

A liquid side stream of on average 183.5 g/hour, which had a temperature of about 66° C., comprised about 90.5 mol % of methanol, 9.3 mol % of dimethyl carbonate and 0.2 mol % of water and was fed to buffer vessel C (compare FIG. 13), was removed from the upper part of the column.

The low-boiling constituents scrubber (compare apparatus 8c in FIG. 11), into the lower part of which the stream (f2) described above (compare FIG. 11) was fed, was a column (dimensions: 33.7×2000 mm, wall thickness: 1.6 mm) filled with packing (glass rings of dimensions 4×4 mm), which was operated at a pressure of 3000 mbar and a temperature of 0° C. and into the upper part of which on average 50.0 g/hour of fresh methanol, which had a temperature of about 15° C., was fed (compare streams (b), (x2) in FIG. 11).

The streams removed from this column, which had a temperature of 0° C., comprised the bottom discharge of on average 61.8 g/hour (compare stream (u) in FIG. 11), which was passed into buffer vessel J (compare FIG. 13) and which comprised about 1.6 mol % of carbon dioxide, 4.2 mol % of methyl nitrite, 90.8 mol % of methanol, 1.4 mol % of dimethyl carbonate and 2.0 mol % of low-boiling constituents, and the gaseous top stream of on average 40.5 g/hour (compare stream (x5) in FIG. 11), which comprised about 3.6 mol % of carbon monoxide, 56.4 mol % of carbon dioxide, 1.3 mol % of methanol, 28.6 mol % of nitrogen monoxide and 10.1 mol % of low-boiling constituents and was passed, together with about 2.5 g/hour of oxygen (compare stream (c1) in FIG. 11) into the lower part of the methyl nitrite after-reactor (compare apparatus 8b in FIG. 11).

This methyl nitrite after-reactor was a column (dimensions: 33.7×3000 mm, wall thickness: 1.6 mm) filled with packing (glass rings of dimensions 4×4 mm), which was operated at a pressure of 3126 mbar and a temperature of about 22° C. and into the upper part of which were fed on average 240.9 g/hour of fresh methanol, which had a temperature of about 15° C. (compare streams (b), (x1) in FIG. 11) and 167.4 g/hour of the liquid mixture from buffer vessel E (compare FIG. 13), which was heated to about 15° C. by means of a prior tube-bundle heat exchanger (compare streams (x3), (x4) in FIG. 11). On average, 1516.9 g/hour (compare stream (x10) in FIG. 11) were fed from buffer vessel G (compare FIG. 11), the contents of which were stirred magnetically, into the central region of the column.

The liquid stream (compare stream (x9) in FIG. 11) of on average 1462.9 g/hour which was removed from the central part of the column, had a temperature of 21.9° C. and comprised about 1.0 mol % of carbon dioxide, 0.9 mol of methyl nitrite, 90.9 mol % of methanol, 5.3 mol % of dimethyl carbonate, 1.4 mol % of water and 0.6 mol % of low-boiling constituents, was passed into buffer vessel L (compare FIG. 11). The liquid bottom discharge (compare stream (b1) in FIG. 11) of on average 487.6 g/hour, which had a temperature of about 21.9° C. and comprised about 1.0 mol % of carbon dioxide, 0.9 mol % of methyl nitrite, 90.9 mol % of methanol, 5.3 mol % of dimethyl carbonate, 1.4 mol % of water and 0.6 mol % of low-boiling constituents, was passed into buffer vessel H (compare FIG. 13). The gaseous top stream (waste gas) (compare stream (t) in FIG. 11) of on average 17.8 g/hour had a temperature of 17.5° C. and comprised about 8.1 mol % of carbon monoxide, 73.9 mol % of carbon dioxide, 0.1 mol % of oxygen, 3.6 mol % of methanol, 4.7 mol % of nitrogen, 4.8 mol % of methane and 4.8 mol % of hydrogen.

About 1462.9 g/hour were fed from buffer vessel L to the upper region of the methyl nitrite desorber (compare apparatus 8a in FIG. 11), into the lower region of which the stream (f4) already described (compare FIG. 11) was fed. This methyl nitrite desorber is a column (dimensions 51×2000 mm, wall thickness 1.6 mm) filled with packing (glass rings of dimensions 4×4 mm), which was operated at a pressure of 3200 mbar and a temperature of about 26° C. The liquid bottom discharge (compare stream (x6) in FIG. 11) of on average 1500.2 g/hour, which had a temperature of about 15° C. and comprised about 0.7 mol % of carbon dioxide, 0.4 mol % of methyl nitrite, 90.4 mol % of methanol, 6.4 mol % of dimethyl carbonate, 1.4 mol % of water and 0.7 mol % of low-boiling constituents, was passed into buffer vessel G (compare FIG. 11). The gaseous top stream (compare stream (f5) in FIG. 11), which has already been described above, was fed to the methyl nitrite synthesis (compare apparatus 3 in FIG. 13).

What is claimed is:

1. A process for the continuous preparation of dimethyl carbonate from carbon monoxide and methyl nitrite and for recycling the nitrogen oxide thereby formed for renewed formation of methyl nitrite, wherein (a) carbon monoxide and methyl nitrite are reacted in the gas phase in the presence of a heterogeneous catalyst comprising a platinum metal, and an inert gas in the temperature range from 50° to 170° C., and in the pressure range from 1 to 5 bar, whereby, as an activator, hydrogen halide, halogen, methyl chloroformate or other substances which contain halogen acting activating under the reaction conditions in a concentration of 0 to 3,000 ppm is added to the gas mixture, (b) the mixture obtained in (a) is separated into gaseous and liquid reaction products, a part of the gaseous stream of 0 to 7% by weight is removed, the therein contained low-boiling constituents are separated off and directed to a further work-up, the therein contained nitrogen monoxide is converted with oxygen and methanol to yield methyl nitrite, which methyl nitrite is separated off and recycled to the process, and the remaining accumulated inert gases are excluded from the process, (c) the gaseous products are reacted with methanol, oxygen and with or without freshly added nitrogen oxide or nitrogen oxide equivalents for renewed formation of the methyl nitrite, the gas mixture which contains the newly formed methyl nitrite being led off and recycled again to the preparation of dimethyl carbonate, and water and any other liquid by-products formed also being led off and removed from the circulation, and (d) the liquid products from (b) are subjected to separation by distillation, in which the entire product mixture is initially subjected to a first distillation, which is carried out under a pressure of 1 to 25 bar, and then either (e1) the top product from the first distillation is fed to another distillation carried out under normal pressure or reduced pressure, in which a methanol-rich discharge is obtained as the bottom product, which is recycled to the preparation of dimethyl carbonate, and in which a top product is obtained which is recycled again to the first distillation, or (e2) the top product from the first distillation is fed to a pervaporation or a vapour permeation, which is operated on the retained material side at a temperature of 20° to 150° C. under a pressure of 0.5 to 10 bar and on the permeate side at a temperature of −30° to +30° C. under a pressure of 0.5 to 500 mbar, in which a methanol-rich outflow is obtained as the permeate, which is recycled to the preparation of dimethyl carbonate, and in which a retained material is obtained which is recycled to the first distillation, and (f) pure dimethyl carbonate is obtained by distillation of the mixture obtained as the bottom running of the first distillation.

2. The process of claim 1, wherein one or more palladium-containing compounds which have been applied to support substances, are used as the catalysts.

3. The process of claim 2, wherein the support substances comprise aluminium oxides, active charcoals, metal phosphates, zeolites, alumosilicates and hetero polyacids and to which further promoters can be added.

4. The process of claim 3, wherein the support substances comprise aluminium oxides and active charcoals.

5. The process of claim 1, which is carried out in step (a) at 70° to 150° C.

6. The process of claim 1, which is carried out in step (a) at 2–4 bar.

7. The process of claim 1, wherein the activator is added to the gas mixture in a concentration of 10 to 1,000 ppm.

8. The process of claim 1, wherein hydrogen chloride, chlorine or methyl chloroformate is employed as activators.

9. The process of claim 1, wherein carbon dioxide, nitrogen or argon is used as the inert gas.

10. The process of claim 9, wherein nitrogen or carbon dioxide is used as the inert gas.

11. The process of claim 1, wherein a scrubber/condenser is employed for separation of the mixture obtained in (a).

12. The process of claim 1, wherein the gaseous reaction products separated off at (b), the oxygen, the freshly added inert gas, the nitrogen oxide or nitrogen oxide equivalent and at least some of the methanol are fed into the apparatus intended for renewed formation of methyl nitrite using a static mixer and optionally one or more one-component or two component nozzles.

13. The method according to claim 12 wherein the nitrogen oxide equivalent is $NO_2$, $N_2O_3$, $N_2O_4$.

14. The process of claim 1, wherein the mixture obtained as the bottom discharge during renewed formation of methyl nitrite according to (c) is fed to a distillation in which aqueous waste products are obtained as a renewed bottom discharge and in which methanol are obtained as the top product and are recycled to the overall process.

15. The process of claim 14, wherein the top product is recycled into the reactor for renewed formation of methyl nitrite, into the pressure distillation according to (d), or into the pervaporation or the vapor permeation, respectively.

16. The process of claim 1, wherein a part of the gaseous stream according to (b) of 0.1 to 5% by weight is removed.

17. The process of claim 1, wherein the distillation according to (d) is carried out at 1 to 12 bar.

18. The process of claim 1, wherein the distillation according to (e1) is carried out at 200 to 1500 mbar.

19. The process of claim 1, wherein the bottom product according to (e1) is recycled to the renewed formation of the methyl nitrite.

20. The process of claim 1, wherein the permeate according to (e2) is recycled to the renewed formation of the methyl nitrite.

21. The method according to claim 1 wherein the nitrogen oxide equivalent is $NO_2$, $N_2O_3$, $N_2O_4$.

* * * * *